US011415575B2

(12) United States Patent
Nagai et al.

(10) Patent No.: US 11,415,575 B2
(45) Date of Patent: Aug. 16, 2022

(54) SAMPLE ANALYZER AND COMPUTER PROGRAM PRODUCT

(71) Applicant: SYSMEX CORPORATION, Kobe (JP)

(72) Inventors: Takaaki Nagai, Kobe (JP); Noriyuki Narisada, Kobe (JP); Daigo Fukuma, Kobe (JP); Masanori Imazu, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 248 days.

(21) Appl. No.: 16/180,590

(22) Filed: Nov. 5, 2018

(65) Prior Publication Data

US 2019/0170733 A1    Jun. 6, 2019

Related U.S. Application Data

(60) Division of application No. 15/908,339, filed on Feb. 28, 2018, now Pat. No. 10,151,746, which is a
(Continued)

(30) Foreign Application Priority Data

Feb. 1, 2007  (JP) ................................. 2007-022523
Mar. 30, 2007 (JP) ................................. 2007-095226

(51) Int. Cl.
*G01N 15/12* (2006.01)
*G01N 15/10* (2006.01)
(Continued)

(52) U.S. Cl.
CPC ......... *G01N 33/5091* (2013.01); *G01N 15/12* (2013.01); *G01N 15/1459* (2013.01);
(Continued)

(58) Field of Classification Search
CPC ...... G01N 15/12; G01N 33/721; G01N 15/10; G01N 33/80; G01N 1/00; G01N 33/5094;
(Continued)

(56) References Cited

U.S. PATENT DOCUMENTS 3,502,974 A   3/1970 Coulter et al.
3,960,497 A   6/1976 Acord
(Continued)

FOREIGN PATENT DOCUMENTS

CN   1591011 A    3/2005
CN   1281963 C   10/2006
(Continued)

OTHER PUBLICATIONS

Cerebrospinal Fluid Cell Fractionation Assay by Automated Blood Cell Measuring Apparatus—CSF Assay by ADVIA 120/120, Apr. 2005.
(Continued)

*Primary Examiner* — Brian J. Sines
(74) *Attorney, Agent, or Firm* — Crowell & Moring LLP

(57) ABSTRACT

A sample analyzer prepares a measurement sample from a blood sample or a body fluid sample which differs from the blood sample; measures the prepared measurement sample; obtains characteristic information representing characteristics of the components in the measurement sample; sets either a blood measurement mode for measuring the blood sample, or a body fluid measurement mode for measuring the body fluid sample as an operating mode; and measures the measurement sample prepared from the blood sample by executing operations in the blood measurement mode when the blood measurement mode has been set, and measuring the measurement sample prepared from the body fluid sample by executing operations in the body fluid measurement mode that differs from the operations in the blood
(Continued)

US 11,415,575 B2

Page 2 measurement mode when the body fluid measurement mode has been set, is disclosed. A computer program product is also disclosed.

8 Claims, 17 Drawing Sheets

Related U.S. Application Data continuation of application No. 14/595,319, filed on Jan. 13, 2015, now Pat. No. 9,933,414, which is a continuation of application No. 13/891,667, filed on May 10, 2013, now Pat. No. 8,968,661, which is a continuation of application No. 12/023,830, filed on Jan. 31, 2008, now Pat. No. 8,440,140.

(51) Int. Cl.
*G01N 1/00* (2006.01)
*G01N 33/50* (2006.01)
*G01N 15/14* (2006.01)
*G01N 33/72* (2006.01)
*G01N 15/00* (2006.01)

(52) U.S. Cl.
CPC ....... *G01N 33/5094* (2013.01); *G01N 33/721* (2013.01); *G01N 33/726* (2013.01); *G01N 2015/008* (2013.01); *G01N 2015/0073* (2013.01); *G01N 2015/0076* (2013.01); *G01N 2015/1486* (2013.01); *Y10T 436/11* (2015.01); *Y10T 436/113332* (2015.01)

(58) Field of Classification Search
CPC .......... G01N 2015/0073; Y10T 436/11; Y10T 436/106664
See application file for complete search history.

(56) References Cited

U.S. PATENT DOCUMENTS

| | | | |
|---|---|---|---|
| 4,001,584 A | 1/1977 | Mueller et al. |
| 4,303,337 A | 12/1981 | James et al. |
| 4,564,598 A | 1/1986 | Briggs |
| 5,122,453 A | 6/1992 | Martin et al. |
| 5,132,087 A | 7/1992 | Manion et al. |
| 5,138,181 A | 8/1992 | Lefevre et al. |
| 5,288,374 A | 2/1994 | Watanabe et al. |
| 5,378,633 A | 1/1995 | Von Behrens et al. |
| 5,555,196 A | 9/1996 | Asano |
| 5,555,198 A | 9/1996 | Asano |
| 5,693,484 A | 12/1997 | Nakamoto et al. |
| 5,812,419 A | 9/1998 | Chupp et al. |
| 5,888,752 A | 3/1999 | Malin et al. |
| 5,939,326 A | 8/1999 | Chupp et al. |
| 6,060,022 A | 5/2000 | Pang et al. |
| 6,106,778 A | 8/2000 | Oku et al. |
| 6,618,143 B2 | 9/2003 | Roche et al. |
| 6,784,981 B1 | 8/2004 | Roche et al. |
| 6,938,502 B2 | 9/2005 | Tanoshima et al. |
| 6,979,570 B2 | 12/2005 | Narisada |
| 7,064,823 B2 | 6/2006 | Roche et al. |
| 7,141,213 B1 | 11/2006 | Pang et al. |
| 7,324,194 B2 | 1/2008 | Roche et al. |
| 7,488,574 B2 | 2/2009 | Oguni |
| 7,618,587 B2 | 11/2009 | Kawate |
| RE42,143 E | 2/2011 | Roche et al. |
| 8,062,591 B2 | 11/2011 | Yamamoto |
| 8,158,439 B2 | 4/2012 | Shibata |
| 8,440,140 B2 | 5/2013 | Nagai et al. |
| 8,668,869 B2 | 3/2014 | Hirayama |
| 8,748,186 B2 | 6/2014 | Kendall et al. |
| 8,797,527 B2 | 8/2014 | Hukari et al. |
| 8,841,117 B2 | 9/2014 | Nagai et al. |
| 8,968,661 B2 | 3/2015 | Nagai et al. |
| 9,243,993 B2 | 1/2016 | Nagai et al. |
| 9,274,054 B2 | 3/2016 | Kendall et al. |
| 9,933,414 B2 | 4/2018 | Nagai et al. |
| 9,976,945 B2 | 5/2018 | Kendall et al. |
| 10,151,746 B2 | 12/2018 | Nagai et al. |
| 10,401,350 B2 | 9/2019 | Nagai et al. |
| 10,401,351 B2 | 9/2019 | Nagai et al. |
| 10,429,292 B2 | 10/2019 | Adams et al. |
| 10,508,983 B2 | 12/2019 | Kendall et al. |
| 10,509,024 B2 | 12/2019 | Zelmanovic et al. |
| 2003/0030783 A1 | 2/2003 | Roche et al. |
| 2003/0143117 A1 | 7/2003 | Nagai et al. |
| 2003/0215890 A1 | 11/2003 | Ornstein et al. |
| 2003/0219850 A1 | 11/2003 | Tsuji et al. |
| 2004/0101440 A1 | 5/2004 | Ishizawa et al. |
| 2004/0156755 A1 | 8/2004 | Wardlaw |
| 2004/0186359 A1 | 9/2004 | Beaudoin et al. |
| 2005/0002552 A1 | 1/2005 | Dunn et al. |
| 2005/0013737 A1 | 1/2005 | Chow et al. |
| 2005/0053521 A1 | 3/2005 | Hirayama |
| 2005/0176152 A1 | 8/2005 | Lopez et al. |
| 2005/0196821 A1 | 9/2005 | Monfre et al. |
| 2005/0219527 A1 | 10/2005 | Ikeuchi et al. |
| 2005/0222504 A1 | 10/2005 | Otvos et al. |
| 2005/0267346 A1 | 12/2005 | Faber et al. |
| 2006/0004541 A1 | 1/2006 | Miyamoto |
| 2006/0029520 A1 | 2/2006 | Tanoshima et al. |
| 2006/0105462 A1 | 5/2006 | Sellek-Prince |
| 2006/0160229 A1 | 7/2006 | Lopez et al. |
| 2006/0189858 A1 | 8/2006 | Sterling et al. |
| 2006/0194325 A1 | 8/2006 | Gable et al. |
| 2006/0195046 A1 | 8/2006 | Sterling |
| 2006/0210438 A1 | 9/2006 | Nagai et al. |
| 2007/0078631 A1 | 4/2007 | Ariyoshi et al. |
| 2007/0105231 A1 | 5/2007 | Riley et al. |
| 2007/0110617 A1 | 5/2007 | Nagai et al. |
| 2008/0056944 A1 | 3/2008 | Nakamura et al. |
| 2008/0187951 A1 | 8/2008 | Nagai et al. |
| 2008/0187990 A1 | 8/2008 | Nagai |
| 2008/0206098 A1 | 8/2008 | Tsutsumida et al. |
| 2008/0241911 A1 | 10/2008 | Ueno et al. |
| 2008/0255705 A1 | 10/2008 | Degeal et al. |
| 2008/0281471 A1 | 11/2008 | Smith et al. |
| 2009/0006003 A1 | 1/2009 | Hirayama |
| 2009/0035873 A1 | 2/2009 | Shibata |
| 2009/0050821 A1 | 2/2009 | Tanaka et al. |
| 2010/0021878 A1 | 1/2010 | Kim |
| 2010/0234703 A1 | 9/2010 | Sterling et al. |
| 2011/0118572 A1 | 5/2011 | Bechtel et al. |
| 2012/0171714 A1 | 7/2012 | Guo |
| 2012/0232362 A1 | 9/2012 | Gable et al. |
| 2019/0339258 A1 | 11/2019 | Nagai et al. |

FOREIGN PATENT DOCUMENTS

| | | |
|---|---|---|
| CN | 2837846 Y | 11/2006 |
| EP | 0 679 889 A2 | 11/1995 |
| EP | 0679889 A2 | 11/1995 |
| EP | 0 679 889 A3 | 3/1996 |
| EP | 0679889 A3 | 3/1996 |
| EP | 1 033 573 A2 | 9/2000 |
| EP | 1033573 A2 | 9/2000 |
| EP | 1 033 573 A3 | 5/2003 |
| EP | 1033573 A3 | 5/2003 |
| EP | 1 376 135 A2 | 1/2004 |
| JP | S58-114754 U | 8/1983 |
| JP | S60-73360 A | 4/1985 |
| JP | 62-150164 A | 7/1987 |
| JP | 02-287260 A | 11/1990 |
| JP | 05-018979 A | 1/1993 |
| JP | 5-133959 | 5/1993 |
| JP | 05-180831 A | 7/1993 |
| JP | H05-256852 A | 10/1993 |
| JP | H06-94676 | 4/1994 |
| JP | H06-207944 A | 7/1994 |
| JP | H07-003360 A | 1/1995 |
| JP | 10-221337 A | 8/1998 |

(56) References Cited

FOREIGN PATENT DOCUMENTS

| JP | 2004-251802 A | 9/2004 |
|---|---|---|
| JP | 2006-292738 A | 10/2006 |
| WO | WO 2019/236682 A1 | 12/2019 |

OTHER PUBLICATIONS

"Coulter® LH 700 Series System", *Beckman Coulter*, Oct. 2003, 114 pages.
"Coulter® LH Series Workstation Body Fluid Application-Operator's Guide", *Beckman Coulter*, Sep. 2004, 48 pages.
510(k) Summary of the XE-5000, *Sysmex America, Inc.*, 2007, 20 pages.
Aulesa, C. et al., "Use of the Advia 120 Hematology Analyzer in the Differential Cytologic Analysis of Biological Fluids (Cerebrospinal, Peritoneal, Pleural, Pericardial, Synovial, and Others)", *Laboratory Hematology*, vol. 9, 2003, pp. 214-224.
Kresie, L. et al., "Performance Evaluation of the Application of Body Fluids on the Sysmex XE-2100 Series Automated Hematology Analyzer", *Laboratory Hematology*, vol. 11, 2005, pp. 24-30.
Harris, N. et al., "Perfomance Evaluation of the ADVIA 2120 Hematology Analyzer: An International Multicenter Clinical Trial", *Laboratory Hematology*, vol. 11, 2005, pp. 62-70.
Andrews, J. et al., "An Evaluation of the Cell-Dyn 3200 for Counting Cells in Cerebrospinal and Other Bodily Fluids", *Laboratory Hematology*, vol. 11, 2005, pp. 98-106.
Brown, W., "Validation of Body Fluid Analysis on the Coulter LH750", *Laboratory Hematology*, vol. 9, 2003, pp. 155-159.
"Declaration of Douglas Drew Dunbabin, In the matter of European Patent No. EP 1 953 527", Oct. 10, 2017, 22 pages
"Declaration of Jonna Scott, In the matter of European Patent No. EP 1 953 527", Oct. 10, 2017, 2 pages.
Harris, N. et al., "Performance Evaluation of the ADVIA 2120 Hematology Analyzer: An International Multicenter Clinical Trial", *Laboratory Hematology*, vol. 11, 2005, pp. 62-70.
Technical Update, "LH 750 Body Fluids Application, Software Revisions 2B3 and 2C2", *Beckman Coulter*, Jan. 31, 2005, 1 page.
Curriculum Vitae of Douglas Drew Dunbabin, 2 pages.
Technical Update, "LH 750 Body Fluids Application, Software Revisions 2B3 and 2C2", *Beckman Coulter*, Jan. 31, 2005, 14 pages.
"Change Notice Regarding Coulter LH700 Series System Reference Manual", *Beckman Coulter*, Nov. 5, 2003, 2 pages.
"Change Notice Regardnig Coulter LH700 Series Body Fluids Application Operator's Guide", *Beckman Coulter*, Dec. 13, 2004, 2 pages.
Hoffman et al., "Automated Counting of Cells in Cerebrospinal Fluid Using the CellDyn-4000 Haematology Analyser" Clin. Chem. Lab Med 2002, vol. 40, No. 11, pp. 1168-1173, Berlin, New York.
Anonymous, "Reference manual 4277248C—Coulter LH700 Series System" Oct. 1, 2003, US, XP055695871, pp. 1-114.
Anonymous, "Operator's Guide" In: "Coulter LH700 Series Body Fluids Application", Sep. 1, 2004, XP055695864, pp. 1-48.
Extended European Search Report in Europe Application No. 20159741.6, dated May 27, 2020, 10 pages.
ES1 Feb. 23, 2018 Response to notice of opposition—for EP Patent No. 1953527, dated Feb. 23, 2018, 26 pages.
ES2 First auxiliary request (marked up)—for EP Application No. 08001713.0, dated Feb. 23, 2018, 7 pages.
ES3 Second auxiliary request (marked up)—for EP Application No. 08001713.0, dated Feb. 23, 2018, 16 pages.
ES4 Third auxiliary request (marked up)—for EP Application No. 08001713.0, dated Feb. 23, 2018, 8 pages.
ES5 Fourth auxiliary request (marked up)—for EP Application No. 08001713.0, dated Feb. 23, 2018, 8 pages.
ES6 Fifth auxiliary request (marked up)—for EP Application No. 08001713.0, dated Feb. 23, 2018, 9 pages.
ES7 Sixth auxiliary request (marked up)—for EP Application No. 08001713.0, dated Feb. 23, 2018, 8 pages.
ES8 Seventh auxiliary request (marked up)—for EP Application No. 08001713.0, dated Feb. 23, 2018.
ES9 Jun. 14, 2018—Letter to EPO for EP Patent No. 1953527, dated Jun. 14, 2018, 2 pages.
ES10 Jun. 26, 2018—Letter to EPO for EP Patent No. 1953527, dated Jun. 26, 2018, 2 pages.
ES11 Sep. 11, 2018—Letter to EPO for EP Patent No. 1953527, dated Sep. 11, 2018, 30 pages.
ES12 Amended claims (mark-up)—auxiliary request 8—for EP Application No. 08001713.0 dated Sep. 11, 2018.
ES13 Nov. 7, 2018—Letter to EPO for EP Patent No. 1953527, dated Nov. 7, 2018, 6 pages.
ES14 Jan. 2, 2019 Submission in opposition proceedings—for EP Patent No. 1953527, dated Jan. 2, 2019, 49 pages.
ES15 auxiliary request 0A—for EP Application No. 08001713.0 dated Jan. 2, 2019, 7 pages.
ES16 auxiliary request 0B—for EP Application No. 08001713.0 dated Jan. 2, 2019, 7 pages.
ES17 auxiliary request 0C—for EP Application No. 08001713.0 dated Jan. 2, 2019, 7 pages.
ES18 auxiliary request 0D—for EP Application No. 08001713.0 dated Jan. 2, 2019, 7 pages.
ES19 auxiliary request 1A—for EP Application No. 08001713.0 dated Jan. 2, 2019, 7 pages.
ES20 auxiliary request 1B—for EP Application No. 08001713.0 dated Jan. 2, 2019, 7 pages.
ES21 auxiliary request 1C—for EP Application No. 08001713.0 dated Jan. 2, 2019, 7 pages.
ES22 auxiliary request 1D—for EP Application No. 08001713.0 dated Jan. 2, 2019, 7 pages.
ES23 auxiliary request 2A—for EP Application No. 08001713.0 dated Jan. 2, 2019, 16 pages.
ES24 auxiliary request 2B—for EP Application No. 08001713.0 dated Jan. 2, 2019, 16 pages.
ES25 auxiliary request 2C—for EP Application No. 08001713.0 dated Jan. 2, 2019, 16 pages.
ES26 auxiliary request 2D—for EP Application No. 08001713.0 dated Jan. 2, 2019, 16 pages.
ES27 auxiliary request 3A—for EP Application No. 08001713.0 dated Jan. 2, 2019, 7 pages.
ES28 auxiliary request 3B—for EP Application No. 08001713.0 dated Jan. 2, 2019, 16 pages.
ES29 auxiliary request 3C—for EP Application No. 08001713.0 dated Jan. 2, 2019, 16 pages.
ES30 auxiliary request 3D—for EP Application No. 08001713.0 dated Jan. 2, 2019, 16 pages.
ES31 auxiliary request 4A—for EP Application No. 08001713.0 dated Jan. 2, 2019, 7 pages.
ES32 auxiliary request 4B—for EP Application No. 08001713.0 dated Jan. 2, 2019, 7 pages.
ES33 auxiliary request 4C—for EP Application No. 08001713.0 dated Jan. 2, 2019, 7 pages.
ES34 auxiliary request 4D—for EP Application No. 08001713.0 dated Jan. 2, 2019, 7 pages.
ES35 auxiliary request 4E—for EP Application No. 08001713.0 dated Jan. 2, 2019, 7 pages.
ES36 auxiliary request 4F—for EP Application No. 08001713.0 dated Jan. 2, 2019, 7 pages.
ES37 auxiliary request 4G—for EP Application No. 08001713.0 dated Jan. 2, 2019, 7 pages.
ES38 auxiliary request 4H—for EP Application No. 08001713.0 dated Jan. 2, 2019, 7 pages.
ES39 auxiliary request 4I—for EP Application No. 08001713.0 dated Jan. 2, 2019, 7 pages.
ES40 auxiliary request 5A—for EP Application No. 08001713.0 dated Jan. 2, 2019, 8 pages.
ES41 auxiliary request 5B—for EP Application No. 08001713.0 dated Jan. 2, 2019, 8 pages.
ES42 auxiliary request 5C—for EP Application No. 08001713.0 dated Jan. 2, 2019, 8 pages.
ES43 auxiliary request 5D—for EP Application No. 08001713.0 dated Jan. 2, 2019, 8 pages.

(56) References Cited

OTHER PUBLICATIONS

ES44 auxiliary request 6A—for EP Application No. 08001713.0 dated Jan. 2, 2019, 7 pages.
ES45 auxiliary request 6B—for EP Application No. 08001713.0 dated Jan. 2, 2019, 7 pages.
ES46 auxiliary request 6C—for EP Application No. 08001713.0 dated Jan. 2, 2019, 7 pages.
ES47 auxiliary request 6D—for EP Application No. 08001713.0 dated Jan. 2, 2019, 7 pages.
ES48 auxiliary request 7A—for EP Application No. 08001713.0 dated Jan. 2, 2019, 7 pages.
ES49 auxiliary request 7B—for EP Application No. 08001713.0 dated Jan. 2, 2019, 7 pages.
ES50 auxiliary request 7C—for EP Application No. 08001713.0 dated Jan. 2, 2019, 7 pages.—for EP Application No. 08001713.0 dated Jan. 2, 2019, 7 pages.
ES51 auxiliary request 7D—for EP Application No. 08001713.0 dated Jan. 2, 2019, 7 pages.
ES52 auxiliary request 8A—for EP Application No. 08001713.0 dated Jan. 2, 2019, 7 pages.
ES53 auxiliary request 8B—for EP Application No. 08001713.0 dated Jan. 2, 2019, 7 pages.
ES54 auxiliary request 8C—for EP Application No. 08001713.0 dated Jan. 2, 2019, 7 pages.
ES55 auxiliary request 8D—for EP Application No. 08001713.0 dated Jan. 2, 2019, 7 pages.
ES56 D34 declaration by Alberto Bonacini—in Opposition against EP Patent No. 1953527, dated Nov. 28, 2018, 3 pages.
ES57 D35 Technical testing of a Beckman Coulter LH750, dated Oct. 18, 2018, 13 pages.
ES58 Feb. 8, 2019—Letter to EPO for EP Patent No. 1953527, dated Feb. 8, 2019, 28 pages.
ES59 amended claims—auxiliary request 4D1 mark-up—for EP Patent No. 1953527, dated Feb. 8, 2019, 8 pages.
ES60 amended claims—auxiliary request 4I1 mark-up—for EP Patent No. 1953527, dated Feb. 8, 2019, 8 pages.
ES61 amended claims—auxiliary request 5D1 mark-up—for EP Patent No. 1953527, dated Feb. 8, 2019, 8 pages.
ES62 amended claims—auxiliary request 8D1 mark-up—for EP Patent No. 1953527, dated Feb. 8, 2019, 8 pages.
ES63 D38 with sticker—Webster's New Encyclopedic Dictionary cited in Opposition against EP Patent No. 1953527, 1996, 3 pages.
ES64 D39 with sticker—Confirm—Wiktionary—dated Jan. 24, 2007, 2 pages.
ES65 D40 with sticker—The American Heritage dictionary, 2019, 3 pages.
EB1 Oct. 11, 2017 Notice of opposition—dated Oct. 11, 2017, 38 pages.
EB2 D1 The European Application as filed—dated Jan. 30, 2008, EP Application No. 08001713.0, 70 pages.
EB3 D2 Coulter® LH700 Series Body Fluids Application Operator's Guide 731113A (Sep. 2004), 48 pages.
EB4 D3 Coulter® LH700 Series System Reference manual 4277248C (Oct. 1, 2003), 114 pages.
EB10 D8 English translation of priority document JP2007022523, date of application Feb. 1, 2007, 35 pages.
EB11 D9 English translation of priority document JP2007095226, date of application Mar. 30, 2007, 35 pages.
EB21 D16c Change Notice regarding D3 release dated Nov. 5, 2003, 2 page.
EB22 D16d Change Notice regarding D2 release dated Dec. 13, 2004, 2 pages.
EB24 Jun. 4, 2018 additional submission—EP Patent No. 1953527, dated Jun. 4, 2018, 2 pages.
EB25 Notice of intervention to a European patent—EP Patent No. 1953527, dated Jun. 1, 2018, 8 pages.
EB26-1 Arguments against patent EP1953527B1 dated Jun. 1, 2018, 66 pages.
EB27 D18 Complaint of Sysmex Corporation filed to Mannheim, dated Feb. 23, 2018, 68 pages.
EB28 D18a Confirmation of the receipt of D18 by the opponent, dated Mar. 2, 2018, 1 page.
EB29 D18b the register of DPMA, dated Jan. 27, 2018, 2 pages.
EB30 D19a JP6-94676, dated Apr. 8, 1994.
EB31 D19b certified English translation of JP6-, dated Apr. 8, 1994.
EB32 D19c Translation certificate, dated Apr. 8, 1994.
EB33 D20 DE4330741 (familiy of JP6-94676), dated Mar. 17, 1994, including English Abstract.
EB38 D25 2nd Declaration of Douglas Drew Dunbabin, dated May 24, 2018, 2 pages.
EB39 D26 2nd Declaration Jonna Scott, dated May 30, 2018, 1 page.
EB40 D29 Declaration of Eric Grace, dated May 23, 2018, 3 pages.
EB41 D30 Annex 1 of Declaration of Eric Grace (list of LH750 customers), dated May 23, 2018, 3 pages.
EB43 Jun. 21, 2018—Response to Official Communication in EP 08001713.0, dated Jun. 21, 2018, 5 pages.
EB44 Jul. 11, 2018—Response to Official Communication in EP 08001713.0, dated Jul. 11, 2018, 4 pages.
EB45 D27 Declaration of Beverly Colbert, dated Jul. 7, 2018, 9 pages.
EB46 D28 "Body fluid cell count, automated coulter LH750" referred to by Beverly Colbert, Revised date Dec. 6, 2006 and Feb. 8, 2008, 7 pages.
EB47 Sep. 12, 2018—Response to Patentee's Submission, dated Sep. 12, 2018, 32 pages.
EB48-1 D32 XE-2100, Copyright 2001-2004, 125 pages.
EB49 D33 XE-5000, date revised Dec. 2006, 265 pages.
EB50 Jan. 4, 2019—Response to 2nd Summons, in EP 08001713.0, dated Jan. 4, 2018, 51 pages.
EB51 D34 Body Fluids 3rd edition, Kjeldsberg, et al., date copyright 1993, 23 pages.
EB52 D35 Declaration of Eric Grace, dated Dec. 21, 2018, 4 pages.
EB53 D36 Service report, dated Jan. 2006, 6 pages.
EB54 D37 Examination decision CN Appln. 200810005238.8 dated Dec. 14, 2018, 37 pages.
EP1 May 8, 2018 preliminary opinion (1st), in EP 08001713.0 dated May 8, 2018, 18 pages.
EP2 Oct. 8, 2018 preliminary opinion (2nd), in EP 08001713.0 dated Oct. 8, 2018, 27 pages.
CSI-2 Jun. 5, 2018—Patentee's Response to Request for Invalidity Trial, including English Translation, dated Jun. 5, 2018, 58 pages.
CS3-2 Sep. 28, 2018 Opinions Statement by Patentee in Trial for Invalidation Procedures, English Translation thereof—dated Sep. 28, 2018, 17 pages.
CS4-2 Jan. 3, 2019 Administrative complaint, English Translation thereof—dated Jan. 3, 2019, 7 pages.
CB1 Apr. 20, 2018—Request for Invalidity Trial for CN Patent No. 200810005238.8, including English Translation, dated Apr. 20, 2018, 30 pages.
CB3 May 21, 2018—Supplementary Opinion in CN 200810005238. 8, including English Translation, dated May 21, 2018, 106 pages.
CP1 Dec. 14, 2018 Examination Decision for Invalidation Announcement Request in CN 200810005238.8, English Translation, dated Dec. 14, 2018, 34 pages.
ES66 Feb. 26, 2019 submission, in EP Patent No. 1953527, 2 pages, dated Feb. 26, 2019.
ES67 Feb. 28, 2019 submission, in EP Patent No. 1953527, 4 pages, dated Feb. 28, 2019.
ES68 Aug. 3, 2019 submission EPO, In EP Patent No. 1953527, 3 pages, dated Mar. 8, 2019.
ES69 Mar. 14, 2019 Submissions as filed, in EP Patent No. 1953527, 6 pages, dated Mar. 14, 2019.
ES70 Mar. 15, 2019_Submissions as filed, in EP Patent No. 1953527, 4 pages, dated Mar. 15, 2019.
ES71 Mar. 18, 2019_Submissions as filed, in EP 1953527, 4 pages, dated Mar. 18, 2019.
EB26-2 Arguments against patent EP1953527B1 dated Jun. 1, 2018, 71 pages.
EB42 D31 Feature analysis of claims 1 and 20, dated Jun. 1, 2018, 2 pages.
EB48-2 D32 XE-2100, Copyright 2001-2004, 130 pages.

(56) References Cited

OTHER PUBLICATIONS

EB55 Feb. 21, 2019 Submission, in EP Patent No. 1953527, 7 pages, dated Feb. 21, 2019.
EB56 EP1953527 D41, including English Translation, 62 pages, dated Oct. 22, 2018.
EB57 Mar. 12, 2019 first letter BC Inc, in EP Patent No. 1953527, 3 pages, dated Mar. 12, 2019.
EB58 Mar. 12, 2019 second letter BC Inc, in EP Patent No. 1953527, 1 page, dated Mar. 12, 2019.
EB59 Mar. 12, 2019 first letter BC GmbH, in EP Patent No. 1953527, 3 pages, dated Mar. 12, 2019.
EB60 Mar. 12, 2019 second letter BC GmbH, in EP Patent No. 1953527, 1 page, dated Mar. 12, 2019.
EP3 Mar. 7, 2019 Information about the result of oral proceedings, in EP Appl. No. 08001713.0, 9 pages, dated Mar. 7, 2019.
EP4 Consolidated list of filed evidence, 4 pages, dated Mar. 7, 2019.
CS2-2 Jul. 19, 2018, Observations of Patentee in the Invalidation Proceeding, including English Translation, 182 pages, dated Jul. 19, 2018.
CB12 Aug. 3, 2018, Observation, including English Translation, in CN Patent No. 200810005238.8, 25 pages, dated Aug. 3, 2018.
ES72 Mar. 20, 2019 submission, 1 page, dated Mar. 20, 2019.
ES73 Mar. 27, 2019 submission, 6 pages, dated Mar. 27, 2019.
ES74 Apr. 18, 2019 submission as filed, 4 pages, dated Apr. 18, 2019.
ES75 Apr. 24, 2019 request for correction of the minutes (as filed), 4 pages, dated Apr. 24, 2019.
EB61 Mar. 19, 2019 Letter from BC GmbH, 5 pages, dated Mar. 19, 2019.
EB62 Mar. 19, 2019 Letter from BC Inc, 5 pages, dated Mar. 19, 2019.
EB63 Teschemacher—list of publications, 4 pages, dated Mar. 19, 2019.
EB64 CV Teschemacher, 1 page, dated Mar. 19, 2019.
EB65 D44, 9 pages, dated Mar. 19, 2019.
EP5 Apr. 17, 2019 minutes, 14 pages, dated Apr. 17, 2019.
EP6 Apr. 17, 2019 Annex to the minutes—AR44 which became AR2, 8 pages, dated Apr. 17, 2019.
EP7 Apr. 17, 2019 Annex to the minutes—consolidated list of filed evidence, 4 pages, dated Apr. 17, 2019.
ES76 May 8, 2019 submission EPO, 4 pages, dated May 8, 2019.
EB66 Apr. 18, 2019 submission by BC, 4 pages, dated Apr. 18, 2019.
EP8 May 14, 2019 communication pursuant to Article 101(1) and Rule 81(2) to (3) EPC, 4 pages, dated May 14, 2019.
EB63 Teschemacher—list of publications, 4 pages, dated Mar. 19, 2019, including partial English translation.
EB64 CV Teschemacher, 3 pages, dated Mar. 19, 2019, including English translation.
EB65 D44, 15 pages, dated Mar. 19, 2019, including English translation.
ES77 May 24, 2019 submission (Rule 82(1) EPC in EP 1953527, dated May 24, 2019, 2 pages.
EB67 Jun. 26, 2019 Letter regarding the opposition procedure from BC GmbH, in EP 1953527, dated Jun. 26, 2019, 5 pages.
EB68 Jun. 26, 2019 Letter regarding the opposition procedure from BC Inc., in EP 1953527, dated Jun. 26, 2019, 5 pages.
ES78 Jul. 11, 2019 submission, in EP 1953527, dated Jul. 11, 2019, 3 pages.
EP9 Provision of corrected minutes, in EP 08001713.0, dated Jul. 19, 2019, 1 page.
EP10 Auxiliary request 2, , in EP 08001713.0, dated Mar. 4, 2019, 8 pages.
EP11 Conclusion of the proceedings and signatures, in EP 08001713. 0, dated Mar. 4, 2019, 1 page.
EP12 Consolidated list of filed evidence, in EP 08001713.0, dated Jul. 19, 2019, 4 pages.
EP13 Corrected minutes, in EP 08001713.0, dated Jul. 19, 2019, 10 pages.
EP14 Reasons for correction of the minutes, in EP 08001713.0, dated Jul. 19, 2019, 3 pages.
EB69 Letter BC GmbH Jul. 23, 2019, in EP Application No. 08001713.0, dated Jul. 23, 2019, 6 pages.
EB70 Letter BC Inc Jul. 23, 2019, in EP Application No. 08001713. 0, dated Jul. 23, 2019, 6 pages.
ES79 Jul. 25, 2019 submission, in EP Application No. 08001713.0, dated Jul. 25, 2019, 11 pages.
EP15 Jul. 31, 2019 Summons, in Europe Application No. 08001713. 0, dated Jul. 31, 2019, 6 pages.
EB71 Aug. 1, 2019 letter BC Inc, in Europe Application No. 08001713.0, dated Aug. 1, 2019, 7 pages.
EB72 Aug. 1, 2019 letter BC GmbH, in Europe Application No. 08001713.0, dated Aug. 1, 2019, 7 pages.
EB73 D44, in Europe Application No. 12815727.8, dated Nov. 16, 2018, 7 pages.
EB74 Letter dated Aug. 6, 2019, in Europe Application No. 08001713. 0, dated Aug. 6, 2019, 1 page.
ES80 Oct. 4, 2019 response, in Europe Patent No. 1953527, dated Oct. 4, 2019, 16 pages.
ES81 Oct. 4, 2019 auxiliary request 1 for the description fair, in Europe Application No. 08001713.0, dated Oct. 4, 2019, 2 pages.
ES82 Oct. 4, 2019 auxiliary request 1 for the description mark-up, in Europe Application No. 08001713.0, dated Oct. 4, 2019, 2 pages.
ES83 Oct. 4, 2019 auxiliary request 2 for the description fair, in Europe Application No. 08001713.0, dated Oct. 4, 2019, 3 pages.
ES84 Oct. 4, 2019 auxiliary request 2 for the description mark-up, in Europe Application No. 08001713.0, dated Oct. 4, 2019, 3 pages.
ES85 Oct. 4, 2019 auxiliary request 3 for the description fair, in Europe Application No. 08001713.0, dated Oct. 4, 2019, 2 pages.
ES86 Oct. 4, 2019 auxiliary request 3 for the description mark-up, in Europe Application No. 08001713.0, dated Oct. 4, 2019, 2 pages.
ES87 Oct. 4, 2019 auxiliary request 4 for the description fair, in Europe Application No. 08001713.0, dated Oct. 4, 2019, 3 pages.
ES88 Oct. 4, 2019 auxiliary request 4 for the description mark-up, in Europe Application No. 08001713.0, dated Oct. 4, 2019, 3 pages.
ES89 Oct. 4, 2019 auxiliary request 5 for the description fair, in Europe Application No. 08001713.0, dated Oct. 4, 2019, 2 pages.
ES90 Oct. 4, 2019 auxiliary request 5 for the description mark-up, in Europe Application No. 08001713.0, dated Oct. 4, 2019, 2 pages.
ES91 Oct. 4, 2019 auxiliary request 6 for the description fair, in Europe Application No. 08001713.0, dated Oct. 4, 2019, 3 pages.
ES92 Oct. 4, 2019 auxiliary request 6 for the description mark-up, in Europe Application No. 08001713.0, dated Oct. 4, 2019, 3 pages.
ES93 Oct. 4, 2019 auxiliary request 7 for the description fair, in Europe Application No. 08001713.0, dated Oct. 4, 2019, 3 pages.
ES94 Oct. 4, 2019 auxiliary request 7 for the description mark-up, in Europe Application No. 08001713.0, dated Oct. 4, 2019, 4 pages.
ES95 submission in opposition proceedings, in Europe Application No. 08001713.0, dated Oct. 4, 2019, 2 pages.
ES96 submission in opposition proceedings(1), in Europe Application No. 08001713.0, dated Oct. 4, 2019, 1 page.
ES97 Acknowledgement of receipt, in Europe Application No. 08001713.0, dated Oct. 4, 2019, 2 pages.
ES98 Acknowledgement of receipt(1), in Europe Application No. 08001713.0, dated Oct. 4, 2019, 1 page.
ES99 Oct. 4, 2019 submission re language, in Europe Patent No. 1953527, dated Oct. 4, 2019, 1 pages.
EB75 Sep. 24, 2019 Brief communication—Opposition proceedings, in Europe Patent No. 1953527, dated Oct. Sep. 24, 2019, 5 pages.
European Patent Office, Extract from the Register of European Patents, listing All Documents: EP1953527, download dated Jan. 20, 2021, 15 pages.
Documents in Appeal Procedure, in Europe Patent No. 1953527 File History, dated Apr. 20, 2020, 3 pages.
Documents in Appeal Procedure, in Europe Patent No. 1953527 File History, dated Apr. 23, 2020, 121 pages.
Documents in Appeal Procedure, in Europe Patent No. 1953527 File History, dated Apr. 29, 2020, 1 page.
Documents in Appeal Procedure, in Europe Patent No. 1953527 File History, dated May 6, 2020, 2 pages.

(56) References Cited

OTHER PUBLICATIONS

Documents in Appeal Procedure, in Europe Patent No. 1953527 File History, dated Jun. 12, 2020, 895 pages.
Documents in Appeal Procedure, in Europe Patent No. 1953527 File History, dated Jun. 16, 2020, 4 pages.
Documents in Appeal Procedure, in Europe Patent No. 1953527 File History, dated Jun. 18, 2020, 3 pages.
Documents in Appeal Procedure, in Europe Patent No. 1953527 File History, dated Jun. 23, 2020, 3 pages.
Documents in Appeal Procedure, in Europe Patent No. 1953527 File History, dated Jun. 26, 2020, 21 pages.
Documents in Appeal Procedure, in Europe Patent No. 1953527 File History, dated Jun. 29, 2020, 2 pages.
Documents in Appeal Procedure, in Europe Patent No. 1953527 File History, dated Jun. 30, 2020, 1 page.
Documents in Appeal Procedure, in Europe Patent No. 1953527 File History, dated Oct. 28, 2020, 545 pages.
Documents in Appeal Procedure, in Europe Patent No. 1953527 File History, dated Nov. 2, 2020, 92 pages.
Documents in Appeal Procedure, in Europe Patent No. 1953527 File History, dated Nov. 4, 2020, 4 pages.
Documents in Appeal Procedure, in Europe Patent No. 1953527 File History, dated Nov. 9, 2020, 2 pages.
Documents in Appeal Procedure, in Europe Patent No. 1953527 File History, dated Nov. 24, 2020, 23 pages.
Documents in Appeal Procedure, in Europe Patent No. 1953527 File History, dated Nov. 30, 2020, 2 pages.
Documents in Appeal Procedure, in Europe Patent No. 1953527 File History, dated Dec. 15, 2020, 20 pages.
Documents in Appeal Procedure, in Europe Patent No. 1953527 File History, dated Dec. 18, 2020, 2 pages.
Documents in Appeal Procedure, in Europe Patent No. 1953527 File History, dated Dec. 28, 2020, 37 pages.
Documents in Appeal Procedure, in Europe Patent No. 1953527 File History, dated Jan. 14, 2021, 2 pages.
ES253 Submission as filed, in EP 08001713.0, dated Jul. 2, 2021, 5 pages.
EB108 dated Jun. 7, 2021 Letter from BCI, in EP 08001713.0, dated Jul. 6, 2021, 1 page.
EB109 dated Aug. 7, 2021 Letter from BCI, in EP 08001713.0, dated Jul. 8, 2021, 16 pages.
EB110 Submission, in EP 08001713.0, dated Jul. 12, 2021, 35 pages.
EB111 D65, in EP 08001713.0, dated May 7, 2021, 61 pages.
EB112 D66, in EP 08001713.0, dated Jun. 1, 2021, 122 pages.
EP47 Official minutes of the oral proceedings—EPO form 3013, in EP 08001713.0, dated Jul. 28, 2021, 17 pages.
Communication pursuant to Article 94(3) EPC, in EP 20159741.6, dated Mar. 19, 2021, 7 pages.
Response as filed, in EP 20159741.6, dated Jul. 29, 2021, 19 pages.
Claim Chart Initial Invalidity Contentions of U.S. Pat. No. 10,401,350, date indicated as May 4, 2020, 38 pages.
Claim Chart Initial Invalidity Contentions of U.S. Pat. No. 10,401,351, date indicated as May 4, 2020, 53 pages.
Defendant Beckman Coulter Inc.'s Initial Invalidity Contentions, date indicated as May 4, 2020, 50 pages.
Beckman Coulter Inc.'s Invalidity Contentions References, Appendix A List of Prior Art References, date indicated as May 4, 2020, 4 pages.
de Jonge, "Automated Counting of White Blood Cells in Synovial Fluid", Rheumatology (Oxford) 43(2):170-73 (date indicated as advance access publication Oct. 1, 2003, date indicated as 2004), 4 pages.
Sugiuchi, "Measurement of Total and Differential White Blood Cell Counts in Synovial Fluid by Means of an Automated Hematology Analyzer", Journal of Laboratory Clinical Medicine 146(1):36-42 (date indicated as Jul. 2005), 7 pages.
Schroeder, "Performance Evaluation of Automated leukocyte Counting in Cerebrospinal Fluid (CSF) by the XE-2100 Compared to Manual Counting", Sysmex Journal International, vol. 14, No. 1 (dated indicated as 2004), 5 pages.
Barnes, "An Evaluation of the Utility of Performing Body Fluid Counts on the Coulter LH 750", Laboratory Hematology 10(3):127-31 (2004), 5 pages.
Aune, "Automated Flow Cytometric Analysis of Blood Cells in Cerebrospinal Fluid: Analytic Performance", American Journal of Clinical Pathology 121(5):690-700 (date indicated as 2004), 11 pages.
Soogarun, "Leukocyte Counts in Cerebrospinal Fluid with the Automated Hematology Analyzer, Technicon H*3", Clinical Laboratory 48(11-12):623-29 (dated indicated as 2002), 7 pages.
Shen, "Cholesterol Crystals Causing Falsely Elevated Automated Cell Count", American Journal of Clinical Pathology 125:358-363 (date indicated as 2006), 6 pages.
Operator's Manual—Automated Hematology Analyzer—XE-2100 Main Unit, Sysmex Corp., dated indicated as 2005, 273 pages.
XE-Series Body Fluid Application, Sysmex Corp., dated indicated as 2004, 2 pages.
Premarket Notification, 510(k) No. K040073, Sysmex Corp., dated indicated as Mar. 18, 2004, 107 pages.
Burgess, et al., Rule based processing of the CD4000, CD3200 and CD Sapphire analyzer output using the Cerner Discern Expert Module, International J of Laboratory Hematology, date indicated as Received Mar. 19, 2008, and date indicated as accepted for publication May 29, 2008, 12 pages.
Grimaldi, et al., Evaluation of the Abbott Cell-DYN 4000 Hematology Analyzer, Hematopathology, Am J Clin Pathol, date indicated as 2000, 113: 497-505, 9 pages.
Body Fluid Analysis for Cellular Composition, Approved Guideline, Clinical and Taboratory standards institute, IFCC, H56-A, vol. 26, No. 26, Replaces H56-P, vol. 25, No. 20, date indicated as proposed guideline Aug. 2005, date indicated as approved guideline Jun. 2006, 112 pages.
Van Acker et al., "Automated Flow Cytometric Analysis of Cerebrospinal Fluid", Clinical Chemistry 47:3, pp. 556-560, date indicated as 2001, 5 pages.
Ziebig et al., "Leukocyte Counts in Cerebrospinal Fluid with the Automated Hematology Analyzer CellDyn 3500 and the Urine Flow Cytometer UF-100", Clinical Chemistry, 46:2, pp. 242-247, date indicated as 2000, 6 pages.
Boer K et al. (date indicated as 2009): Evaluation of the XE-5000 for the automated analysis of blood cells in cerebrospinal fluid. Clin Biochem 42: 684-691, 8 pages.
Cho J et al. (date indicated as 2019): Performance Evaluation of Body Fluid Cellular Analysis Using the Beckman Coulter UniCel DxH 800, Sysmex XN-350, and UF-5000 Automated Cellular Analyzers. Ann Lab Med. date indicated as Mar. 2020;40(2):122-130. English, date indicated as Published online Oct. 23, 2019, 10 pages.
DxH800 Body Fluids, Performance Evaluation of Body Fluids on the UniCel DxH 800 Coulter Cellular Analysis System, date indicated as published 2009, 8 pages.
Fleming C et al. (date indicated as 2012): Validation of the body fluid module on the new Sysmex XN-1000 for counting blood cells in cerebrospinal fluid and other body fluids. Clin Chem Lab Med. Date indicated as Oct. 1, 2012 ;50(10):1791-1798, 8 pages.
Fleming C et al. (date indicated as 2013): Improved software on the Sysmex XE-5000 Bf mode for counting leukocytes in cerebrospinal fluid. Clin Chem Lab Med date indicated as 2013; 51(4): e61-e63, 4 pages.
Genc S et al. (date indicated as 2016): Evaluation of Cell Counting in Body Fluids Comparison of Two Automated Hematology Analyzers with Manual Microscopy. Clin Lab. Date indicated as Dec. 1, 2016 ;62(12):2449-2453, 5 pages.
Jonge R et al. (date indicated as 2006): Automated analysis of pleural fluid total and differential leukocyte counts with the Sysmex XE-2100. Clin Chem Med Lab 44: 1367-1371,5 pages.
Jonge R, et al. (date indicated as 2010): Evaluation of the new body fluid mode on the Sysmex XE-5000 for counting leukocytes and erythrocytes in cerebrospinal fluid and other body fluids. Clin Chem Lab Med. Date indicated as May 2010;48(5):665-75, 12 pages.

(56) References Cited

OTHER PUBLICATIONS

Li, A et al. (date indicated as 2014): Automated white blood cell counts in cerebrospinal fluid using the body fluid mode on the platform Sysmex XE-5000. Scandinavian Journal of Clinical and Laboratory Investigation, 74:8, 673-680, 9 pages.
Paris A, et al. (date indicated as 2010): Performance evaluation of the body fluid mode on the platform Sysmex XE-5000 series automated hematology analyzer. Int J Lab Hematol. Date indicated as Oct. 2010;32(5):539-47 / pp. 1-9, 9 pages.
Perne' et al., (date indicated as 2012): Performance Evaluation of the Sysmex XE-5000 Hematology Analyzer for White Blood Cell Analysis in Cerebrospinal Fluid. Arch Pathol Lab Med—vol. 136, date indicated as Feb. 2012, 5 pages.
Riedl JA et al. (date indicated as 2010): Automated morphological analysis of cells in body fluids by the digital microscopy system DM96. J Clin Pathol 63: 538-43, 6 pages.
Sandhaus, LM et al. (date indicated as 2010): Automated Cerebrospinal Fluid Cell Counts Using the Sysmex XE-5000. Am J Clin Pathol, date indicated as 2010;134:734-738, 5 pages.
Zimmermann M et al. (date indicated as 2011): Automated vs. manual cerebrospinal fluid cell counts: a work and cost analysis comparing the Sysmex XE-5000 and the Fuchs-Rosenthal manual counting chamber. Int J Lab Hematol 33: 629-637, 9 pages.
Zur B et al. (date indicated as 2011): Evaluation of 2 Hematology Analyzers in Body Fluid Mode versus Flow Cytometry Immunophenotyping of Mainly Neurosurgical Cerebrospinal Fluid Samples. Cen Eur Neurosurg 73: 93-98, 6 pages.
IPR2020-01500 (U.S. Pat. No. 10,401,350), Petition for Inter Partes Review, Petition 1 of 2, date indicated as Aug. 20, 2020, 99 pages.
IPR2020-01500 (U.S. Pat. No. 10,401,350), Petitioner's Power of Attorney, date indicated as Aug. 20, 2020, 2 pages.
IPR2020-01500 (U.S. Pat. No. 10,401,350), Petitioner's Notice Regarding Multiple Petitions, date indicated as Aug. 20, 2020, 7 pages.
IPR2020-01500 (U.S. Pat. No. 10,401,350), Notice of Filing Date Accorded to Petition and Time for Filing Patent Owner Preliminary Response, date indicated as Aug. 24, 2020, 5 pages.
IPR2020-01500 (U.S. Pat. No. 10,401,350), Patent Owners' Mandatory Disclosures, date indicated as Sep. 8, 2020, 5 pages.
IPR2020-01500 (U.S. Pat. No. 10,401,350), Patent Owner Sysmex Corporation and Sysmex America, Inc's (Sysmex) Preliminary Response to Petition for Inter Partes Review of U.S. Pat. No. 10,401,350, date indicated as Nov. 24, 2020, 72 pages.
IPR2020-01500 (U.S. Pat. No. 10,401,350), Patent Owner Sysmex Corporation and Sysmex America, Inc's Response to Petitioner's Notice Regarding Multiple Petitions, date indicated as Nov. 24, 2020, 7 pages.
IPR2020-01500 (U.S. Pat. No. 10,401,350), Order Grant Withdrawal Shoffstall (Circ), date indicated as Feb. 22, 2021, 3 pages.
IPR2020-01500 (U.S. Pat. No. 10,401,350), DDI Final (Circ), date indicated as Feb. 22, 2021, 23 pages.
IPR2020-01500 (U.S. Pat. No. 10,401,350), Granting Patent Owners Motion to Withdraw Counsel, date indicated as Feb. 22, 2021, 3 pages.
IPR2020-01500 (U.S. Pat. No. 10,401,350), Patent Owner Exhibit, Williams et al., "Gaining Efficiency in the Laboratory—Automated Body Fluid Cell Counts Evaluation of the Body Fluid Application on the Sysmex XE-5000 Hematology Analyzer", vol. 42, No. 7, Lab Medicine, date indicated as Jul. 2011, 7 pages.
IPR2020-01500 (U.S. Pat. No. 10,401,350), Patent Owner Exhibit 2005, Hearing Transcript, date indicated Jan. 7, 2020, 20 pages.
IPR2020-01500 (U.S. Pat. No. 10,401,350), Patent Owner Exhibit 2006, Nicole Kopinski Email with BCI Letter to Court, date indicated as Dec. 20, 2019, 13 pages.
IPR2020-01500 (U.S. Pat. No. 10,401,350), Patent Owner Exhibit 2007, Joint Letter on Narrowing, date indicated as Jan. 22, 2020, 5 pages.
IPR2020-01500 (U.S. Pat. No. 10,401,350), Patent Owner Exhibit 2020, D.l. 143 Markman Order, date indicated as Oct. 27, 2020, 2 pages.
IPR2020-01500 (U.S. Pat. No. 10,401,350), Patent Owner Exhibit 2008, Mallin Declaration, date indicated as Nov. 23, 2020, 12 pages.
IPR2020-01500 (U.S. Pat. No. 10,401,350), Patent Owner Exhibit 2009, Sysmex US and SAI Document Production Index, date indicated as Nov. 16, 2020, 1 page.
IPR2020-01500 (U.S. Pat. No. 10,401,350), Patent Owner Exhibit 2010, Scorp Document Production Index, date indicated as Nov. 16, 2020, 1 page.
IPR2020-01500 (U.S. Pat. No. 10,401,350), Patent Owner Exhibit 2011, Docket Sheet, date indicated as date filed Sep. 3, 2019, 28 pages.
IPR2020-01500 (U.S. Pat. No. 10,401,350), Patent Owner Exhibit 2012, Scheduling Order, date indicated as Jan. 16, 2020, 17 pages.
IPR2020-01500 (U.S. Pat. No. 10,401,350), Patent Owner Exhibit 2013 Stipulation and [Proposed] Order Extending Deadline, date indicated as Oct. 27, 2020, 2 pages.
IPR2020-01500 (U.S. Pat. No. 10,401,350), Patent Owner Exhibit 2014, Email regarding MTD Extension, date indicated as Oct. 27, 2020, 4 pages.
IPR2020-01500 (U.S. Pat. No. 10,401,350), Patent Owner Exhibit 2015, Defendant Beckman Coulter Inc.'s Initial Invalidity Contentions, date indicated as May 4, 2020, 148 pages.
IPR2020-01500 (U.S. Pat. No. 10,401,350), Patent Owner Exhibit 2016, Plantiffs' Disclosure of Asserted Patents, Accused Products, and Damages Model, date indicated as Dec. 30, 2019, 3 pages.
IPR2020-01500 (U.S. Pat. No. 10,401,350), Patent Owner Exhibit 2017, Sysmex Corporation's Initial Disclosures Pursuant to Fed. R. Civ. P. 26(a)(1) and Paragraph 3 of the Default Standard, date indicated as Feb. 13, 2020, 13 pages.
IPR2020-01500 (U.S. Pat. No. 10,401,350), Patent Owner Exhibit 2018, XE Pro Series User's Guide, date indicated as Copyright 2002-2004, date indicated as date of Tast revision Jan. 2004, 69 pages.
IPR2020-01500 (U.S. Pat. No. 10,401,350), Patent Owner Exhibit 2019, Stipulation and [Proposed] Order Regarding Case Deadlines, date indicated as Aug. 4, 2020, 2 pages.
IPR2020-01500 (U.S. Pat. No. 10,401,350), Patent Owner Exhibit 2021, DocketNavigator Stats and Declaration, Documents Search, date indicated as Oct. 30, 2020, 15 pages.
IPR2020-01500 (U.S. Pat. No. 10,401,350), Patent Owner Exhibit 2022, Joint Letter, Doc. 123, date indicated as Oct. 9, 2020, 2 pages.
IPR2020-01500 (U.S. Pat. No. 10,401,350), Patent Owner Exhibit 2025, First Amended Answer and Counterclaims of Defendant Beckman Coulter, Inc., date indicated as Oct. 2, 2020, 317 pages.
IPR2020-01500 (U.S. Pat. No. 10,401,350), Patent Owner Exhibit 2026, (K992875), 510(k) Summary of Safety and Effectiveness Information Sysmex Automated Hematology Analyzer XE-2100, date indicated as Aug. 25, 1999, 6 pages.
IPR2020-01500 (U.S. Pat. No. 10,401,350), Patent Owner Exhibit 2027, Markman Hearing Mini, date indicated as Oct. 28, 2020, 55 pages.
IPR2020-01500 (U.S. Pat. No. 10,401,350), Patent Owner Exhibit 2029, Joint CC Brief, UniCel DxH 800 Coulter Cellular Analysis System, Hematology Specimen Processing Module with System Manager, date indicated as Oct. 14, 2020, 3 pages.
IPR2020-01500 (U.S. Pat. No. 10,401,350), Patent Owner Exhibit 2030 Beckman Coulter, Inc. EPO Submission (EP 08001713.0 / 1953527), date indicated as Sep. 12, 2018, 32 pages.
IPR2020-01500 (U.S. Pat. No. 10,401,350), Patent Owner Exhibit 2031, Plaintiff Sysmex Corporation's Responses to Beckman Coulter Inc.'s Second Set of Interrogatories (Nos. 9-13), date indicated as Jun. 12, 2020, 7 pages.
IPR2020-01500 (U.S. Pat. No. 10,401,350), Patent Owner Exhibit 2032, Amendment, date indicated as Oct. 22, 2018, 12 pages.
IPR2020-01500 (U.S. Pat. No. 10,401,350), Patent Owner Exhibit 2033, Notice of Allowance for U.S. Appl. No. 15/908,339, date indicated as Oct. 30, 2018, 16 pages.
IPR2020-01500 (U.S. Pat. No. 10,401,350), Patent Owner Exhibit 2035, Joint Claim Construction Brief, date indicated as Oct. 14, 2020, 89 pages.
IPR2020-01500 (U.S. Pat. No. 10,401,350), Patent Owner Exhibit 2039, Response and Amendment, date indicated as Jun. 5, 2017, 10 pages.

(56) References Cited

OTHER PUBLICATIONS

IPR2020-01500 (U.S. Pat. No. 10,401,350), Patent Owner Exhibit 2040, Final Office Action in U.S. Appl. No. 14/595,341, date indicated as Sep. 12, 2017, 5 pages.
IPR2020-01500 (U.S. Pat. No. 10,401,350), Patent Owner Exhibit 2041, Notice of Allowance in U.S. Appl. No. 14/595,341, date indicated as Nov. 5, 2018, 8 pages.
IPR2020-01500 (U.S. Pat. No. 10,401,350), Patent Owner Exhibit 2042, (K040073), XE-2100 510k Submission, 510(k) Premarket Notification-Traditional System XE-Series, Automated Hematology Analyzer, Body Fluid Application, date indicated as Jan. 13, 2004, 3 pages.
IPR2020-01500 (U.S. Pat. No. 10,401,350), Patent Owner Exhibit 2043, (K032039), Xe Pro IG Software, 510(k) Summary of Safety and Effectiveness, date indicated as Sep. 8, 2003, 5 pages.
IPR2020-01500 (U.S. Pat. No. 10,401,350), Patent Owner Exhibit 2044, (K040073), Decision Summary, 510(k) Summary of Safety and Effectiveness, date indicated as Mar. 18, 2004, 10 pages.
IPR2020-01500 (U.S. Pat. No. 10,401,350), Petitioner Exhibit 1002, File History of U.S. Appl. No. 16/214,417, USPN 10401350, date indicated as Apr. 2020, 242 pages.
IPR2020-01500 (U.S. Pat. No. 10,401,350), Petitioner Exhibit 1003, Declaration of John W. Roche, date indicated as Aug. 17, 2020, 358 pages.
IPR2020-01500 (U.S. Pat. No. 10,401,350), Petitioner Exhibit 1015, Declaration of Eric M. Grace, date indicated as Aug. 12, 2020, 16 pages.
IPR2020-01500 (U.S. Pat. No. 10,401,350), Petitioner Exhibit 1021, Affidavit of Christopher Butler, date indicated as May 12, 2020, 4 pages.
IPR2020-01500 (U.S. Pat. No. 10,401,350), Petitioner Exhibit 1024, Coulter LH 750 Body Fluid Application, date indicated as Oct. 22, 2019, 3 pages.
IPR2020-01500 (U.S. Pat. No. 10,401,350), Petitioner Exhibit 1029, Information Disclosure Statement, date indicated as Mar. 14, 2006, 3 pages.
IPR2020-01500 (U.S. Pat. No. 10,401,350), Petitioner Exhibit 1030, Operator's Manual Automated Hematology Analyzer, XE-2100 Main Unit, date indicated as Revised Mar. 2005, 20 pages.
IPR2020-01500 (U.S. Pat. No. 10,401,350), Petitioner Exhibit 1033, LH750 Installed Information, date indicated as installed through Feb. 2006, Feb. 2007, 2 pages.
IPR2020-01500 (U.S. Pat. No. 10,401,350), Petitioner Exhibit 1034, (K030606), 510(K) Summary of Safety and Effectiveness of Coulter LH 750 Body Fluids Application, date indicated as Apr. 21, 2003, 5 pages.
IPR2020-01500 (U.S. Pat. No. 10,401,350), Petitioner Exhibit 1035, (K040073), 510(k) Summary of Safety and Effectiveness, date indicated as Mar. 18, 2004, 5 pages.
IPR2020-01500 (U.S. Pat. No. 10,401,350), Petitioner Exhibit 1036, Affidavit of Christopher Butler, date indicated as Apr. 20, 2020, 5 pages.
IPR2020-01500 (U.S. Pat. No. 10,401,350), Petitioner Exhibit 1040, Operator's Manual Automated Hematology Analyzer, XE-2100, IPU (Information Processing Unit), date indicated as Date of last revision Feb. 1999, 200 pages.
IPR2020-01500 (U.S. Pat. No. 10,401,350), Petitioner Exhibit 1042, Complaint for Patent Infringement, date indicated as Sep. 3, 2019, 13 pages.
IPR2020-01500 (U.S. Pat. No. 10,401,350), Petitioner Exhibit 1043, Joint Claim Construction Chart, date indicated as Jul. 6, 2020, 27 pages.
IPR2020-01501 (U.S. Pat. No. 10,401,350), Patent Owner Exhibit 2048, Document 20, date indicated as Dec. 23, 2019, 30 pages.
IPR2020-01501 (U.S. Pat. No. 10,401,350), Patent Owner Exhibit 2047, Petitioner's EPO Submission, EP 08001713.0 / 1953527, date indicated as Jun. 1, 2018, 137 pages.
IPR2020-01501 (U.S. Pat. No. 10,401,350), Patent Owner Exhibit 2008, Mallin Declaration, date indicated as Nov. 23, 2020, 13 pages.
IPR2020-01501 (U.S. Pat. No. 10,401,350), Petition for Inter Partes Review, Petition 2 of 2, date indicated as Aug. 20, 2020, 103 pages.
IPR2020-01501 (U.S. Pat. No. 10,401,350), Petitioner's Power of Attorney, date indicated as Aug. 20, 2020, 2 pages.
IPR2020-01501 (U.S. Pat. No. 10,401,350), Petitioner's Notice Regarding Multiple Petitions, date indicated as Aug. 20, 2020, 7 pages.
IPR2020-01501 (U.S. Pat. No. 10,401,350), Notice of Filing Date Accorded to Petition and Time for Filing Patent Owner Preliminary Response, date indicated as Aug. 24, 2020, 5 pages.
IPR2020-01501 (U.S. Pat. No. 10,401,350), Patent Owner's Mandatory Disclosures, date indicated as Sep. 8, 2020, 5 pages.
IPR2020-01501 (U.S. Pat. No. 10,401,350), Patent Owner Sysmex Corporation and Sysmex America, Inc's (Sysmex) Preliminary Response to Petition for Inter Partes Review of U.S. Pat. No. 10,401,350, date indicated as Nov. 24, 2020, 74 pages.
IPR2020-01501 (U.S. Pat. No. 10,401,350), Patent Owner Sysmex Corporation and Sysmex America, Inc's Response to Petitioner's Notice Regarding Multiple Petitions, date indicated as Nov. 24, 2020, 7 pages.
IPR2020-01501 (U.S. Pat. No. 10,401,350), Patent Owners' Updated Mandatory Disclosures, date indicated as Dec. 14, 2020, 5 pages.
IPR2020-01501 (U.S. Pat. No. 10,401,350), Patent Owners' Motion to Withdraw Counsel, date indicated as Dec. 14, 2020, 4 pages.
IPR2020-01501 (U.S. Pat. No. 10,401,350), Decision Denying Institution of Inter Partes Review, date indicated as Feb. 22, 2021, 26 pages.
IPR2020-01501 (U.S. Pat. No. 10,401,350), Order Granting Patent Owner's Motion to Withdraw Counsel, date indicated as Feb. 22, 2021, 3 pages.
IPR2020-01501 (U.S. Pat. No. 10,401,350), Patent Owner Exhibit 2031, Plaintiff Sysmex Corporation's Responses to Beckman Coulter Inc.'s Second Set of Interrogatories (Nos. 9-13), date indicated as Jun. 12, 2020, 7 pages.
IPR2020-01502 (U.S. Pat. No. 10,401,351), Petition for Inter Partes Review, date indicated as Aug. 20, 2020, 107 pages.
IPR2020-01502 (U.S. Pat. No. 10,401,351), Petitioner's Power of Attorney, date indicated as Aug. 20, 2020, 2 pages.
IPR2020-01502 (U.S. Pat. No. 10,401,351), Petitioner's Notice Regarding Multiple Petitions, date indicated as Aug. 20, 2020, 7 pages.
IPR2020-01502 (U.S. Pat. No. 10,401,351), Notice of Filing Date Accorded to Petition and Time for Filing Patent Owner Preliminary Response, date indicated as Aug. 24, 2020, 5 pages.
IPR2020-01502 (U.S. Pat. No. 10,401,351), Patent Owners' Mandatory Disclosures, date indicated as Sep. 8, 2020, 5 pages.
IPR2020-01502 (U.S. Pat. No. 10,401,351), Patent Owner Sysmex Corporation and Sysmex America, Inc's (Sysmex) Preliminary Response to Petition for Inter Partes Review of U.S. Pat. No. 10,401,351, Response 1 of 2, date indicated as Nov. 24, 2020, 78 pages.
IPR2020-01502 (U.S. Pat. No. 10,401,351), Patent Owner's Updated Mandatory Disclosures, date indicated as Dec. 14, 2020, 5 pages.
IPR2020-01502 (U.S. Pat. No. 10,401,351), Patent Owners' Motion to Withdraw Counsel, date indicated as Dec. 14, 2020, 4 pages.
IPR2020-01502 (U.S. Pat. No. 10,401,351), Decision, Denying Institution of Inter Partes Review, date indicated as Feb. 22, 2021, 23 pages.
IPR2020-01500 (U.S. Pat. No. 10,401,350), Decision, Denying Institution of Inter Partes Review, date indicated as Feb. 22, 2021, 23 pages.
IPR2020-01502 (U.S. Pat. No. 10,401,351), Petitioner Exhibit 1002, Request for Certificate of Correction, date indicated as 2019, 227 pages.
IPR2020-01502 (U.S. Pat. No. 10,401,351), Petitioner Exhibit 1003, Declaration of John W. Roche in Support of Petition for Inter Partes Review, date indicated as Aug. 17, 2020, 244 pages.
IPR2020-01502 (U.S. Pat. No. 10,401,351), Petitioner Exhibit 1015, Declaration of Eric M. Grace, date indicated as Aug. 12, 2020, 16 pages.
IPR2020-01503 (U.S. Pat. No. 10,401,351), Patent Owner Exhibit 2008, Mallin Declaration, date indicated as Nov. 23, 2020, 10 pages.

(56) References Cited

OTHER PUBLICATIONS

IPR2020-01503 (U.S. Pat. No. 10,401,351), Patent Owner Exhibit 2011, Docket Sheet, date indicated as date filed Sep. 3, 2019, 28 pages.
IPR2020-01503 (U.S. Pat. No. 10,401,351), Patent Owner Exhibit 2015, Defendant Beckman Coulter Inc.'s Initial Invalidity Contentions, date indicated as May 4, 2020, 148 pages.
IPR2020-01503 (U.S. Pat. No. 10,401,351), Patent Owner Exhibit 2016, Plaintiffs' Disclosure of Asserted Patents, Accused Products, and Damages Model, date indicated as Dec. 30, 2019, 3 pages.
IPR2020-01503 (U.S. Pat. No. 10,401,3501, Patent Owner Exhibit 2017, Sysmex Corporation's Initial Disclosures Pursuant to Fed. R. Civ. P. 26(a)(1) and Paragraph 3 of the Default Standard, date indicated as Feb. 13, 2020, 13 pages.
IPR2020-01503 (U.S. Pat. No. 10,401,351), Patent Owner Exhibit 2019, Stipulation and [Proposed] Order Regarding Case Deadlines, date indicated as Aug. 4, 2020, 2 pages.
IPR2020-01503 (U.S. Pat. No. 10,401,351), Patent Owner Exhibit 2021, DocketNavigator Stats and Declaration, Documents Search, date indicated as Oct. 30, 2020, 15 pages.
IPR2020-01503 (U.S. Pat. No. 10,401,351), Patent Owner Exhibit 2035, Joint Claim Construction Brief, date indicated as Oct. 14, 2020, 89 pages.
IPR2020-01503 (U.S. Pat. No. 10,401,351), Patent Owner Exhibit 2039, Response and Amendment, date indicated as Jun. 5, 2017, 10 pages.
IPR2020-01503 (U.S. Pat. No. 10,401,351), Patent Owner Exhibit 2052, Declaration of J. Paul Robinson, Ph.D. in Support of Patent Owners' Preliminary Response to Petition for Inter Partes Review of U.S. Pat. No. 10,401,351, Response 2 of 2 date indicated as Nov. 24, 2020, 136 pages.
IPR2020-01503 (U.S. Pat. No. 10,401,351), Patent Owner Exhibit 2053, Excerpts from the '140 (U.S. Appl. No. 12/023,830) prosecution history, date indicated as Sep. 29, 2010, 16 pages.
IPR2020-01503 (U.S. Pat. No. 10,401,351), Patent Owner Exhibit 2054, Excerpts from the '746 (U.S. Appl. No. 15/908,339), prosecution history, date indicated as Oct. 22, 2018, 28 pages.
IPR2020-01503 (U.S. Pat. No. 10,401,351), Patent Owner Exhibit 2057, Akeroyd et al., On Counting Leukocytes by Electronic Means, Amer. J of Clin. Pathology, vol. 31, No. 2, date indicated as Feb. 1959, p. 188-192; 5 pages.
IPR2020-01503 (U.S. Pat. No. 10,401,351), Patent Owner Exhibit 2058, Science Coulter ad, date indicated as Mar. 18, 1960, 1 page.
IPR2020-01503 (U.S. Pat. No. 10,401,351), Patent Owner Exhibit 2059, Rowan et al., The Coulter Counter Model S Plus-the shape of things to come, Clin. Lab. Haemat., date indicated as 1979, p. 29-40, 12 pages.
IPR2020-01503 (U.S. Pat. No. 10,401,351), Patent Owner Exhibit 2060, Saleh et al., Direct detection of antibody-antigen binding using an on-chip artificial pore, date indicated as Feb. 4, 2003, vol. 100, No. 3, p. 820-824, 5 pages.
IPR2020-01503 (U.S. Pat. No. 10,401,351), Patent Owner Exhibit 2061, Jagtiani et al., Detection and Counting of micro-scale particles and pollen using a multi-aperture Coulter counter, date indicated as 2006, Meas. Sci. Technol. 17, 1706, 10 pages.
IPR2020-01503 (U.S. Pat. No. 10,401,351), Patent Owner Exhibit 2062, Excerpt from the '661 (U.S. Appl. No. 13/891,667) prosecution history, 1 page, date indicated as Jul. 28, 2014.
IPR2020-01503 (U.S. Pat. No. 10,401,351), Petition for Inter Partes Review, date indicated as Aug. 20, 2020, 83 pages.
IPR2020-01503 (U.S. Pat. No. 10,401,351), Petitioner's Power of Attorney, date indicated as Aug. 20, 2020, 2 pages.
IPR2020-01503 (U.S. Pat. No. 10,401,351), Petioner's Notice Regarding Multiple Petitions, date indicated as Aug. 20, 2020, 7 pages.
IPR2020-01503 (U.S. Pat. No. 10,401,351), Notice of Filing Date Accorded to Petition and Time for Filing Patent Owner Preliminary Response, date indicated as Aug. 24, 2020, 5 pages.
IPR2020-01503 (U.S. Pat. No. 10,401,351), Patent Owners' Mandatory Disclosures, date indicated as Sep. 8, 2020, 5 pages.

IPR2020-01503 (U.S. Pat. No. 10,401,351), Patent Owner Sysmex Corporation and Sysmex America, Inc's Preliminary Response to Petition For Inter Partes Review of U.S. Pat. No. 10,401,351, Response 2 of 2, date indicated as Nov. 24, 2020, 63 pages.
IPR2020-01503 (U.S. Pat. No. 10,401,351), Patent Owners' Mandatory Disclosures, date indicated as Dec. 14, 2020, 5 pages.
IPR2020-01503 (U.S. Pat. No. 10,401,351), Patent Owners' Motion to Withdraw Counsel, date indicated as Dec. 14, 2020, 4 pages.
IPR2020-01503 (U.S. Pat. No. 10,401,351), Decision Denying Institution of Inter Partes Review, date indicated as Feb. 22, 2021, 23 pages.
IPR2020-01503 (U.S. Pat. No. 10,401,351), Decision Granting Institution of Inter Partes Review, date indicated as Feb. 23, 2021, 31 pages.
IPR2020-01503 (U.S. Pat. No. 10,401,351), Scheduling Order, date indicated as Feb. 23, 2021, 13 pages.
IPR2020-01503 (U.S. Pat. No. 10,401,351), Patent Owner Sysmex Corporation and Sysmex America, Inc's Objections to Petitioner's Evidence, date indicated as Mar. 9, 2021, 10 pages.
IPR2020-01503 (U.S. Pat. No. 10,401,351), Patent Owners' Notice of Deposition of John W. Roche, date indicated as Apr. 14, 2021, 4 pages.
IPR2020-01503 (U.S. Pat. No. 10,401,351), Patent Owner's Updated Mandatory Disclosures, date indicated as Apr. 14, 2021, 5 pages.
IPR2020-01503 (U.S. Pat. No. 10,401,351), Exhibit 3001, Plaintiffs' Proposed Stipulation and Order Regarding Case Deadlines, date indicated as Feb. 11, 2021, 2 pages.
IPR2020-01503 (U.S. Pat. No. 10,401,351), Petitioner Exhibit 1046, Excerpts from 746 (U.S. Appl. No. 15/908,339) prosecution history, date indicated as Oct. 22, 2018, 26 pages.
IPR2020-01503 (U.S. Pat. No. 10,401,351), Petitioner Exhibit 1048, Declaration of John W. Roche in Support of Petition for Inter Partes Review of U.S. Pat. No. 10,401,351, date indicated as Aug. 18, 2020, 91 pages.
Exhibit DX-006, XE-2100D Automated Haematology Analyser Instructions for use, date indicated as date of last revision, Nov. 2006, date exhibit indicated as Jan. 2021, 257 pages.
Exhibit DX-007, Operator's Manual Automated Hematology Analyzer XE-2100 IPU (Information Processing Unit)(North American Edition), date indicated as date of last revision Apr. 2004, Exhibit date indicated as Jan. 2021, 293 pages.
Exhibit DX-008, Operator's Manual Automated Hematology Analyzer XE-2100 (IPU (Information Processing Unit), date indicated as date of last revision Nov. 2006, exhibit date indicated as Jan. 2021, 263 pages.
Exhibit DDX-0034, Operator's Manual Automated Hematology Analyzer XE-2100 Main Unit, date indicated as date of last revision, Mar. 2005, exhibit date indicated as Jan. 2021, 273 pages.
Exhibit DDX-0093, Sysmex, Automated Hematology Analyzer XT-2000i/XT-1800i, Instructions for Use (North American Edition, date indicated as date of last revision Jul. 2006, exhibit date indicated as Feb. 2021, 431 pages.
Exhibit DDX-106, Body Fluid Analysis Made Simple—and Automated, Coulter LH 750 Body Fluid Application, date indicated as Feb. 4, 2021, 2 pages.
Exhibit DDX-107, Coulter LH 750 Body Fluid Application, date indicated as Oct. 22, 2019, 3 pages.
Exhibit DDX-116, University of Texas Medical Branch Partners with Sysmex America, Inc., date indicated as Jul. 20, 2006, 3 pages.
Exhibit DDX-117, Sysmex America, Inc., and Bio-Rad Laboratories, Inc. Announce the Availability of Bio-Rad Diabetes Testing on the Sysmex HST-N Automation Line, date indicated as Aug. 16, 2007, 3 pages.
Exhibit DDX-118, Sysmex, Welcome to Sysmex, Our Company, Press Center, date indicated as Mar. 2, 2004, 2 pages.
Exhibit DDX-119, Sysmex, Untitled Document, Our Company, Press Center, date indicated as Nov. 18, 2006, 1 page.
Exhibit DDX-124, FDA Clears Body Fluids Analysis Application for Sysmex America, Inc. XT-Series, date indicated as Jul. 25, 2006, 4 pages.
Exhibit DDX-40, XT-Series Body Fluid Application, date indicated as 2006, Exhibit date indicated as Jan. 15, 2021, 2 pages.

(56) References Cited

OTHER PUBLICATIONS

Exhibit DDX-75, Department of Health & Human Services, date indicated as Mar. 18, 2004, Exhibit date indicated as Jan. 28, 2021, 66 pages.
Exhibit DDX-83, 510(k) Summary of Safety and Effectiveness, (K061150), date indicated as Jul. 6, 2006, Exhibit date indicated as Jan. 28, 2021, 5 pages.
Walters, Hematology and the Analysis of Body Fluids, Elite Learning, date indicated as Apr. 29, 2021, 17 pages.
Customer Information, Literature List—Body Fluids, (No. 140110d) date indicated as Jan. 2014, 5 pages.
CSR1 20190222, document dated Feb. 22, 2019, including English translation, 14 pages.
CSR2-1 20201028 and CSR2-2 20201028, documents dated Oct. 28, 2020, including English translations, 109 pages.
CSR3-1 20210225 and CSR3-2 202102251 documents dated Feb. 25, 2021, including English translations, 20 pages.
CBR1 20190521, documents dated May 21, 2019, including English translation, 4 pages.
CCR1-1 (2019) 73 72 and CCR1-2 (2019) 73 72, documents dated Jan. 28, 2021, including English translations, 33 pages.
CPR1 20190201 response from PRB, documents dated Feb. 1, 2019, including English translation, 9 pages.
ES100 20191126 short submission with EPO—document in EP proceeding for EP 1953527, date indicated as Nov. 26, 2019, 3 pages.
ES101 dated Dec. 5, 2019 submission—document in EP proceeding for EP 1953527, date indicated as Dec. 5, 2019, 6 pages.
ES102 dated Dec. 17, 2019 submission—document in EP proceeding for EP 1953527, date indicated as Dec. 17, 2019, 2 pages.
ES103 t020042eu1—document in EP proceeding for EP 0294397, date indicated as Feb. 28, 2003, 13 pages.
ES104 t990699eu1—document in EP proceeding for EP 0394326 date indicated as Jan. 19, 2005, 35 pages.
ES105 dated Jan. 1, 2020 request for correction of the minutes, in EP Patent No. 1953527, dated Jan. 10, 2020, 6 pages.
ES106 annex—dated Dec. 6, 2019—Consolidated list of filed evidence, in EP Patent No. 1953527, dated Dec. 6, 2019, 4 pages.
ES107 dated Jan. 22, 2020 submission, in EP Patent No. 1953527, dated Jan. 22, 2020, 5 pages.
ES108 Formal appeal in EP proceeding EP 1953527 date indicated as Apr. 14, 2020, 2 pages.
ES109 dated Jun. 12, 2020 statement of grounds of appeal—in EP proceeding EP 1953527, date indicated as Jun. 12, 2020, 113 pages.
ES110 Acknowledgement of receipt—in EP proceeding EP 08001713.0, date indicated as Jun. 12, 2020, 5 pages.
ES111 amended claims—auxiliary request 0A fair—in EP proceeding EP 08001713.0, date indicated as Jun. 12, 2020, 7 pages.
ES112 amended claims—auxiliary request 0A mark-up—in EP proceeding EP 08001713.0, date indicated as Jun. 12, 2020, 7 pages.
ES113 amended claims—auxiliary request 0B fair—in EP proceeding EP 08001713.0, date indicated as Jun. 12, 2020, 7 pages.
ES114 amended claims—auxiliary request 0B mark-up—in EP proceeding EP 08001713.0, date indicated as Jun. 12, 2020, 7 pages.
ES115 amended claims—auxiliary request 0C fair—in EP proceeding EP 08001713.0, date indicated as Jun. 12, 2020, 7 pages.
ES116 amended claims—auxiliary request 0C mark-up—in EP proceeding EP 08001713.0, date indicated as Jun. 12, 2020, 7 pages.
ES117 amended claims—auxiliary request 0D fair—in EP proceeding EP 08001713.0, date indicated as Jun. 12, 2020, 7 pages.
ES118 amended claims—auxiliary request 0D mark-up—in EP proceeding EP 08001713.0, date indicated as Jun. 12, 2020, 7 pages.
ES119 amended claims—auxiliary request 1 fair—in EP proceeding EP 08001713.0, date indicated as Jun. 12, 2020, 8 pages.
ES120 amended claims—auxiliary request 1 mark-up—in EP proceeding EP 08001713.0, date indicated as Jun. 12, 2020, 9 pages.
ES121 amended claims—auxiliary request 1A fair—in EP proceeding EP 08001713.0, date indicated as Jun. 12, 2020, 8 pages.
ES122 amended claims—auxiliary request 1A mark-up—in EP proceeding EP 08001713.0, date indicated as Jun. 12, 2020, 8 pages.
ES123 amended claims—auxiliary request 1B fair—in EP proceeding EP 08001713.0, date indicated as Jun. 12, 2020, 8 pages.
ES124 amended claims—auxiliary request 1B mark-up—in EP proceeding EP 08001713.0, date indicated as Jun. 12, 2020, 8 pages.
ES125 amended claims—auxiliary request 1C fair—in EP proceeding EP 08001713.0, date indicated as Jun. 12, 2020, 8 pages.
ES126 amended claims—auxiliary request 1C mark-up—in EP proceeding EP 08001713.0, date indicated as Jun. 12, 2020, 8 pages.
ES127 amended claims—auxiliary request 1D fair—in EP proceeding EP 08001713.0, date indicated as Jun. 12, 2020, 8 pages.
ES128 amended claims—auxiliary request 1D mark-up—in EP proceeding EP 08001713.0, date indicated as Jun. 12, 2020, 8 pages.
ES129 amended claims—auxiliary request 1E fair—in EP proceeding EP 08001713.0, date indicated as Jun. 12, 2020, 8 pages.
ES130 amended claims—auxiliary request 1E mark-up—in EP proceeding EP 08001713.0, date indicated as Jun. 12, 2020, 8 pages.
ES131 amended claims—auxiliary request 2 fair—in EP proceeding EP 08001713.0, date indicated as Jun. 12, 2020, 7 pages.
ES132 amended claims—auxiliary request 2 mark-up—in EP proceeding EP 08001713.0, date indicated as Jun. 12, 2020, 8 pages.
ES133 amended claims—auxiliary request 2A fair—in EP proceeding EP 08001713.0, date indicated as Jun. 12, 2020, 7 pages.
ES134 amended claims—auxiliary request 2A mark-up—in EP proceeding EP 08001713.0, date indicated as Jun. 12, 2020, 7 pages.
ES135 amended claims—auxiliary request 2B fair—in EP proceeding EP 08001713.0, date indicated as Jun. 12, 2020, 7 pages.
ES136 amended claims—auxiliary request 2B mark-up—in EP proceeding EP 08001713.0, date indicated as Jun. 12, 2020, 7 pages.
ES137 amended claims—auxiliary request 2C fair—in EP proceeding EP 08001713.0, date indicated as Jun. 12, 2020, 7 pages.
ES138 amended claims—auxiliary request 2C mark-up—in EP proceeding EP 08001713.0, date indicated as Jun. 12, 2020, 7 pages.
ES139 amended claims—auxiliary request 2D fair—in EP proceeding EP 08001713.0, date indicated as Jun. 12, 2020, 7 pages.
ES140 amended claims—auxiliary request 2D mark-up—in EP proceeding EP 08001713.0, date indicated as Jun. 12, 2020, 7 pages.
ES141 amended claims—auxiliary request 2F fair—in EP proceeding EP 08001713.0, date indicated as Jun. 12, 2020, 8 pages.
ES142 amended claims—auxiliary request 2F mark-up—in EP proceeding EP 08001713.0, date indicated as Jun. 12, 2020, 8 pages.
ES143 amended claims—auxiliary request 3 fair—in EP proceeding EP 08001713.0, date indicated as Jun. 12, 2020, 8 pages.
ES144 amended claims—auxiliary request 3 mark-up—in EP proceeding EP 08001713.0, date indicated as Jun. 12, 2020, 8 pages.
ES145 amended claims—auxiliary request 3A fair—in EP proceeding EP 08001713.0, date indicated as Jun. 12, 2020, 7 pages.
ES146 amended claims—auxiliary request 3A mark-up—in EP proceeding EP 08001713.0, date indicated as Jun. 12, 2020, 7 pages.
ES147 amended claims—auxiliary request 3B fair—in EP proceeding EP 08001713.0, date indicated as Jun. 12, 2020, 7 pages.
ES148 amended claims—auxiliary request 3B mark-up—in EP proceeding EP 08001713.0, date indicated as Jun. 12, 2020, 7 pages.
ES149 amended claims—auxiliary request 3C fair—in EP proceeding EP 08001713.0, date indicated as Jun. 12, 2020, 8 pages.
ES150 amended claims—auxiliary request 3C mark-up—in EP proceeding EP 08001713.0, date indicated as Jun. 12, 2020, 8 pages.
ES151 amended claims—auxiliary request 3D fair—in EP proceeding EP 08001713.0, date indicated as Jun. 12, 2020, 8 pages.
ES152 amended claims—auxiliary request 3D mark-up—in EP proceeding EP 08001713.0, date indicated as Jun. 12, 2020, 8 pages.
ES153 amended claims—auxiliary request 3F fair—in EP proceeding EP 08001713.0, date indicated as Jun. 12, 2020, 8 pages.
ES154 amended claims—auxiliary request 3F mark-up—in EP proceeding EP 08001713.0, date indicated as Jun. 12, 2020, 8 pages.
ES155 amended claims—auxiliary request 4 fair—in EP proceeding EP 08001713.0, date indicated as Jun. 12, 2020, 7 pages.
ES156 amended claims—auxiliary request 4 mark-up—in EP proceeding EP 08001713.0, date indicated as Jun. 12, 2020, 8 pages.
ES157 amended claims—auxiliary request 4A fair—in EP proceeding EP 08001713.0, date indicated as Jun. 12, 2020, 7 pages.
ES158 amended claims—auxiliary request 4A mark-up—in EP proceeding EP 08001713.0, date indicated as Jun. 12, 2020, 7 pages.

(56) References Cited

OTHER PUBLICATIONS

ES159 amended claims—auxiliary request 4B fair—in EP proceeding EP 08001713.0, date indicated as Jun. 12, 2020, 7 pages.
ES160 amended claims—auxiliary request 4B mark-up—in EP proceeding EP 08001713.0, date indicated as Jun. 12, 2020, 7 pages.
ES161 amended claims—auxiliary request 4C fair—in EP proceeding EP 08001713.0, date indicated as Jun. 12, 2020, 7 pages.
ES162 amended claims—auxiliary request 4C mark-up—in EP proceeding EP 08001713.0, date indicated as Jun. 12, 2020, 7 pages.
ES163 amended claims—auxiliary request 4D fair—in EP proceeding EP 08001713.0, date indicated as Jun. 12, 2020, 7 pages.
ES164 amended claims—auxiliary request 4D mark-up—in EP proceeding EP 08001713.0, date indicated as Jun. 12, 2020, 7 pages.
ES165 amended description paragraphs for AR0A fair—in EP proceeding EP 08001713.0, date indicated as Jun. 12, 2020, 1 pages.
ES166 amended description paragraphs for AR0A mark-up—in EP proceeding EP 08001713.0, date indicated as Jun. 12, 2020, 1 pages.
ES167 amended description paragraphs for AR0B fair—in EP proceeding EP 08001713.0, date indicated as Jun. 12, 2020, 2 pages.
ES168 amended description paragraphs for AR0B mark-up—in EP proceeding EP 08001713.0, date indicated as Jun. 12, 2020, 2 pages.
ES169 amended description paragraphs for AR0C—in EP proceeding EP 08001713.0, date indicated as Jun. 12, 2020, 1 pages.
ES170 amended description paragraphs for AR0C mark-up—in EP proceeding EP 08001713.0, date indicated as Jun. 12, 2020, 1 pages.
ES171 amended description paragraphs for AR0D fair—in EP proceeding EP 08001713.0, date indicated as Jun. 12, 2020, 2 pages.
ES172 amended description paragraphs for AR0D mark-up—in EP proceeding EP 08001713.0, date indicated as Jun. 12, 2020, 2 pages.
ES173 amended description paragraphs for AR1A fair—in EP proceeding EP 08001713.0, date indicated as Jun. 12, 2020, 3 pages.
ES174 amended description paragraphs for AR1A mark-up—in EP proceeding EP 08001713.0, date indicated as Jun. 12, 2020, 3 pages.
ES175 amended description paragraphs for AR1B fair—in EP proceeding EP 08001713.0, date indicated as Jun. 12, 2020, 4 pages.
ES176 amended description paragraphs for AR1B mark-up—in EP proceeding EP 08001713.0, date indicated as Jun. 12, 2020, 4 pages.
ES177 amended description paragraphs for AR1C fair—in EP proceeding EP 08001713.0, date indicated as Jun. 12, 2020, 3 pages.
ES178 amended description paragraphs for AR1C mark-up—in EP proceeding EP 08001713.0, date indicated as Jun. 12, 2020, 3 pages.
ES179 amended description paragraphs for AR1D fair—in EP proceeding EP 08001713.0, date indicated as Jun. 12, 2020, 4 pages.
ES180 amended description paragraphs for AR1D mark-up—in EP proceeding EP 08001713.0, date indicated as Jun. 12, 2020, 4 pages.
ES181 amended description paragraphs for AR1E fair—in EP proceeding EP 08001713.0, date indicated as Jun. 12, 2020, 4 pages.
ES182 amended description paragraphs for AR1E mark-up—in EP proceeding EP 08001713.0, date indicated as Jun. 12, 2020, 4 pages.
ES183 amended description paragraphs for AR2 fair—in EP proceeding EP 08001713.0, date indicated as Jun. 12, 2020, 2 pages.
ES184 amended description paragraphs for AR2 mark-up—in EP proceeding EP 08001713.0, date indicated as Jun. 12, 2020, 2 pages.
ES185 amended description paragraphs for AR2A fair—in EP proceeding EP 08001713.0, date indicated as Jun. 12, 2020, 2 pages.
ES186 amended description paragraphs for AR2A mark-up—in EP proceeding EP 08001713.0, date indicated as Jun. 12, 2020, 2 pages.
ES187 amended description paragraphs for AR2B fair—in EP proceeding EP 08001713.0, date indicated as Jun. 12, 2020, 3 pages.
ES188 amended description paragraphs for AR2B mark-up—in EP proceeding EP 08001713.0, date indicated as Jun. 12, 2020, 3 pages.
ES189 amended description paragraphs for AR2C fair—in EP proceeding EP 08001713.0, date indicated as Jun. 12, 2020, 2 pages.
ES190 amended description paragraphs for AR2C mark-up—in EP proceeding EP 08001713.0, date indicated as Jun. 12, 2020, 2 pages.
ES191 amended description paragraphs for AR2D fair—in EP proceeding EP 08001713.0, date indicated as Jun. 12, 2020, 3 pages.
ES192 amended description paragraphs for AR2D mark-up—in EP proceeding EP 08001713.0, date indicated as Jun. 12, 2020, 3 pages.
ES193 amended description paragraphs for AR2F fair—in EP proceeding EP 08001713.0, date indicated as Jun. 12, 2020, 3 pages.
ES194 amended description paragraphs for AR2F mark-up—in EP proceeding EP 08001713.0, date indicated as Jun. 12, 2020, 3 pages.
ES195 amended description paragraphs for AR3 fair—in EP proceeding EP 08001713.0, date indicated as Jun. 12, 2020, 2 pages.
ES196 amended description paragraphs for AR3 mark-up—in EP proceeding EP 08001713.0, date indicated as Jun. 12, 2020, 2 pages.
ES197 amended description paragraphs for AR3A fair—in EP proceeding EP 08001713.0, date indicated as Jun. 12, 2020, 3 pages.
ES198 amended description paragraphs for AR3A mark-up—in EP proceeding EP 08001713.0, date indicated as Jun. 12, 2020, 3 pages.
ES199 amended description paragraphs for AR3B fair—in EP proceeding EP 08001713.0, date indicated as Jun. 12, 2020, 3 pages.
ES200 amended description paragraphs for AR3B mark-up—in EP proceeding EP 08001713.0, date indicated as Jun. 12, 2020, 3 pages.
ES201 amended description paragraphs for AR3C fair—in EP proceeding EP 08001713.0, date indicated as Jun. 12, 2020, 2 pages.
ES202 amended description paragraphs for AR3C mark-up—in EP proceeding EP 08001713.0, date indicated as Jun. 12, 2020, 2 pages.
ES203 amended description paragraphs for AR3D fair—in EP proceeding EP 08001713.0, date indicated as Jun. 12, 2020, 3 pages.
ES204 amended description paragraphs for AR3D mark-up—in EP proceeding EP 08001713.0, date indicated as Jun. 12, 2020, 3 pages.
ES205 amended description paragraphs for AR3F fair—in EP proceeding EP 08001713.0, date indicated as Jun. 12, 2020, 3 pages.
ES206 amended description paragraphs for AR3F mark-up—in EP proceeding EP 08001713.0, date indicated as Jun. 12, 2020, 3 pages.
ES207 amended description paragraphs for AR4 fair—in EP proceeding EP 08001713.0, date indicated as Jun. 12, 2020, 3 pages.
ES208 amended description paragraphs for AR4 mark-up—in EP proceeding EP 08001713.0, date indicated as Jun. 12, 2020, 3 pages.
ES209 amended description paragraphs for AR4A fair—in EP proceeding EP 08001713.0, date indicated as Jun. 12, 2020, 3 pages.
ES210 amended description paragraphs for AR4A mark-up—in EP proceeding EP 08001713.0, date indicated as Jun. 12, 2020, 3 pages.
ES211 amended description paragraphs for AR4B fair—in EP proceeding EP 08001713.0, date indicated as Jun. 12, 2020, 3 pages.
ES212 amended description paragraphs for AR4B mark-up—in EP proceeding EP 08001713.0, date indicated as Jun. 12, 2020, 3 pages.
ES213 amended description paragraphs for AR4C fair—in EP proceeding EP 08001713.0, date indicated as Jun. 12, 2020, 3 pages.
ES214 amended description paragraphs for AR4C mark-up—in EP proceeding EP 08001713.0, date indicated as Jun. 12, 2020, 3 pages.
ES215 amended description paragraphs for AR4D fair—in EP proceeding EP 08001713.0, date indicated as Jun. 12, 2020, 3 pages.
ES216 amended description paragraphs for AR4D mark-up—in EP proceeding EP 08001713.0, date indicated as Jun. 12, 2020, 3 pages.
ES217 D46 with sticker—Robert Mallin, Enclosure D46 in Opposition EP 1953527, date indicated as Jul. 12, 2018, 22 pages.
ES218 Letter accompanying subsequently filed items—in EP proceeding 08001713.0, date indicated as Jun. 12, 2020, 6 pages.
ES219 Letter accompanying subsequently filed documents—in EP proceeding 08001713.0, date indicated as Jun. 16, 2020, 1 page.
ES220 Acknowledgement of receipt—in EP proceeding 08001713.0, date indicated as Jun. 16, 2020, 1 page.
ES221 response as filed—in EP proceeding 08001713.0, date indicated as Jun. 16, 2020, 2 pages.
ES222 dated Oct. 28, 2020 reply—in EP proceeding 08001713.0, date indicated as Oct. 28, 2020, 97 pages.
ES223 Acknowledgement of receipt—in EP proceeding 08001713.0, date indicated as Oct. 28, 2020, 1 page.
ES224 Letter accompanying subsequently filed items—in EP proceeding 08001713.0, date indicated as Oct. 28, 2020, 1 page.
ES225 D50—not for public inspection—Evaluation Agreement, date indicated as Jun. 14, 2006, 15 pages.
ES226 D51—not for public inspection—Patentee's further arguments pertaining to D50, date indicated as 2020, 3 pages.
ES227 Letter accompanying subsequently filed items(1)—in EP proceeding 08001713.0, date indicated as Oct. 28, 2020, 1 page.
ES228 Acknowledgement of receipt(1)—in EP proceeding 08001713.0, date indicated as Oct. 28, 2020, 1 page.

(56) References Cited

OTHER PUBLICATIONS

ES229 Letter accompanying subsequently filed items—in EP proceeding 08001713.0, date indicated as Nov. 24, 2020, 1 page.
ES230 dated Nov. 24, 2020 submission—in EP proceeding 08001713.0, date indicated as Nov. 24, 2020, 21 pages.
ES231 Acknowledgement of receipt—in EP proceeding 08001713.0, date indicated as Nov. 2, 2020, 1 page.
ES232 Letter accompanying subsequently filed items—in EP proceeding 08001713.0, date indicated as Dec. 16, 2020, 1 page.
ES233 Acknowledgement of receipt—in EP proceeding 08001713.0, date indicated as Dec. 15, 2020, 1 page.
ES234 dated Dec. 15, 2020 submission—in EP proceeding 08001713.0, date indicated as Dec. 15, 2020, 18 page.
ES235 Letter accompanying subsequently filed items—in EP proceeding 08001713.0, date indicated as Dec. 28, 2020, 1 page.
ES236 Acknowledgement of receipt—in EP proceeding 08001713.0, date indicated as Dec. 28, 2020, 1 page.
ES237 dated Dec. 28, 2020 submission—in EP proceeding 08001713.0, date indicated as Dec. 28. 28, 2020, 35 page.
ES238 Letter accompanying subsequently filed items—in EP proceeding 08001713.0, date indicated as Mar. 31, 2021, 1 page.
ES239 Acknowledgement of receipt—in EP proceeding 08001713.0, date indicated as Mar. 31, 2021, 1 page.
ES240 dated Mar. 31, 2021 submission—in EP proceeding 08001713.0, date indicated as Mar. 31, 2021, 1 page.
ES241 dated May 17, 2021 letter to director A. J. van Putten—in EP proceeding 08001713.0, date indicated as May 17, 2021, 3 pages.
ES242 dated May 17, 2021 request for correction of the minutes—in EP proceeding 08001713.0, date indicated as May 17, 2021, 7 pages.
ES243 dated May 17, 2021 request for correction under R140EPC—in EP proceeding 08001713.0, date indicated as May 17, 2021, 7 pages.
ES244 dated May 17, 2021 submission to the Board—in EP proceeding 08001713.0, date indicated as May 17, 2021, 3 pages.
ES245 Acknowledgement of receipt(1)—in EP proceeding 08001713.0, date indicated as May 17, 2021, 1 page.
ES246 Acknowledgement of receipt(2)—in EP proceeding 08001713.0, date indicated as May 17, 2021, 1 page.
ES247 Acknowledgement of receipt(3)—in EP proceeding 08001713.0, date indicated as May 17, 2021, 1 page.
ES248 Acknowledgement of receipt—in EP proceeding 08001713.0, date indicated as May 17, 2021, 1 page.
ES249 Letter accompanying subsequently filed items—in EP proceeding 08001713.0, date indicated as May 17, 2021, 1 pages.
ES250 submission in opposition proceedings(1)—in EP proceeding 08001713.0, date indicated as May 17, 2021, 2 pages.
ES251 submission in opposition proceedings(2)—in EP proceeding 08001713.0, date indicated as May 17, 2021, 2 pages.
ES252 submission in opposition proceedings—in EP proceeding 08001713.0, date indicated as May 17, 2021, 2 pages.
EB76 dated Mar. 12, 2019 BC submission.
EB77 ORALLETT 01+02 of Aug. 12, 2019(Partiality に関するBCレター).
EB78 Jun. 12, 2019—BC partiality objection.
EB79 dated Jan. 14, 2020 BC submission, in EP Patent No. 1953527, dated Jan. 14, 2020, 7 pages.
EB80 dated Feb. 24, 2020 BC GmbH notice of appeal—in EP proceeding 08001713.0, date indicated as Feb. 19, 2020, 2 pages.
EB81 dated Feb. 24, 2020 BC submission—in EP proceeding 08001713.0, date indicated as Feb. 24, 2020, 5 pages.
EB82 dated Feb. 24, 2020 BC form accompanying the submission—in EP proceeding 08001713.0, date indicated as Feb. 24, 2020, 1 pages.
EB83 dated Feb. 24, 2020 BC annex 1—in EP proceeding 08001713.0, date indicated as Feb. 24, 2020, 18 pages.
EB84 dated Feb. 24, 2020 BC annex 2—in EP proceeding 08001713.0, date indicated as Feb. 24, 2020, 16 pages.
EB85 BC's letter of Apr. 23, 2020—in EP proceeding 08001713.0, date indicated as Apr. 23, 2020, 2 pages.
EB86 Documents filed with LG Mannheim—in EP proceeding 08001713.0, date indicated as Mar. 18, 2019, including English translation, 236 pages.
EB87 Accompanying form—in EP proceeding 08001713.0, date indicated as Apr. 23, 2020, 1 pages.
EB88 Receipt—in EP proceeding 08001713.0, date indicated as Apr. 23, 2020, 1 pages.
EB89 Filing receipt—in EP proceeding 08001713.0, date indicated as Jun. 12, 2020, 2 pages.
EB90 Accompanying form—in EP proceeding 08001713.0, date indicated as Jun. 12, 2020, 1 pages.
EB91 BC's statement of grounds of appeal—in EP proceeding 08001713.0, date indicated as Jun. 12, 2020, 92 pages.
EB92 BC's D46—in EP proceeding 08001713.0, date indicated as Apr. 14, 2020, including English translation, 7 pages.
EB93 BC's D47, Fleming et al., "Improved software on the Sysmex XE-5000 Bf mode for counting leukocytes in cerebrospinal fluid" Clin. Chem. Lab. Med., 2013, 51(4), e61-e63, 3 pages.
EB94 BC's D48, Communication Links Between the Data Manager and a Host Computer, Advia 2120 Hematology System, date indicated as 2004, 88 pages.
EB95 BC's D49, Die Kunst der Hamatologie, Advia 120, including English translation, date indicated as 2002, 30 pages.
EB96 dated Nov. 2, 2020 BC's submission,—in EP proceeding 08001713.0, date indicated as Nov. 2, 2020, 3 pages.
EB97 Letter accompanying subsequently filed items—in EP proceeding 08001713.0, date indicated as Nov. 2, 2020, 1 pages.
EB98 D65—Case of *Zagrebacka Banka DD* v. *Croatia*, First Section, Judgment, date indicated as Mar. 12, 2014, 87 pages.
EB99 Electronic receipt—in EP proceeding 08001713.0, date indicated as Nov. 2, 2020, 1 pages.
EB100 Letter accompanying subsequently filed items—in EP proceeding 08001713.0, date indicated as Feb. 10, 2021, 1 pages.
EB101 (Electronic) Receipt—in EP proceeding 08001713.0, date indicated as Feb. 10, 2021, 1 pages.
EB102 dated Feb. 10, 2021 BC submission—in EP proceeding 08001713.0, date indicated as Feb. 10, 2021, 2 pages.
EB103 Letter BC GmbH—in EP proceeding 08001713.0, date indicated as Mar. 22, 2021, 3 pages.
EB104 Letter BCI—in EP proceeding 08001713.0, date indicated as Mar. 22, 2021, 3 pages.
EB105 dated May 12, 2021 BC submission—in EP proceeding 08001713.0, date indicated as May 12, 2021, 30 pages.
EB106 D66, Beschluss, date indicated as Apr. 21, 2021, including English translation, 52 pages.
EB107 D67, Verfugung, date indicated as May 4, 2021, including English translation, 3 pages.
EP16 dated Dec. 6, 2019 - Consolidated list of filed evidence date indicated as Dec.6, 2019, 4 pages.
EP17 Information about the result of oral proceedings date indicated as Dec. 6 and 9, 2019, 1 page.
EP18 dated Dec. 19, 2019 minutes in EP proceeding EP 08001713.0 date indicated as Dec. 19, 2019, 12 pages.
EP19 Annex 1 in EP proceeding EP 08001713.0 date indicated as Dec. 6, 2019, 6 pages.
EP20 Annex 2 in EP proceeding EP 08001713.0 date indicated as Dec. 6, 2019, 6 pages.
EP21 Annex 3 in EP proceeding EP 08001713.0 date indicated as Dec. 6, 2019, 1 page.
EP22 Annex 4 in EP proceeding EP 08001713.0 date indicated as Dec. 8, 2019, 15 pages.
EP23 Annex 5 in EP proceeding EP 08001713.0 date indicated as Dec. 9, 2019, 1 page.
EP24 Annex 6 in EP proceeding EP 08001713.0 date indicated as Dec. 9, 2019, 6 pages.
EP25 Decision, in EP Patent No. 1953527, dated Feb. 4, 2020, 57 pages.
EP26 Handwritten signatures, in EP Patent No. 1953527, dated Jan. 21, 2020, date filed Feb. 4, 2020, 1 page.
EP27 Annex A, in EP Patent No. 1953527, date filed Feb. 4, 2020, 4 pages.
EP28 Annex B, in EP Patent No. 1953527, dated Dec. 9, 2019, date filed Feb. 4, 2020, 9 pages.

(56) References Cited

OTHER PUBLICATIONS

EP29 Annex C, in EP Patent No. 1953527, dated Dec. 6, 2019, date filed Feb. 4, 2020, 1 page.
EP30 Annex D, in EP Patent No. 1953527, dated Dec. 8, 2019, date filed Feb. 4, 2020, 15 pages.
EP31 Annex E, in EP Patent No. 1953527, dated Dec. 9, 2019, date filed Feb. 4, 2020, 1 page.
EP32 Annex F, in EP Patent No. 1953527, date filed Feb. 4, 2020, 28 pages.
EP33 Annex G, in EP Patent No. 1953527, date filed Feb. 4, 2020, 2 pages.
EP34 Annex H, in EP Patent No. 1953527, date filed Feb. 4, 2020, 1 page.
EP35 Druckexemplar in opposition procedure.pdf, in EP Patent No. 1953527, date filed Feb. 4, 2020, 38 pages.
EP36 Brief communication—Opposition proceedings—in EP proceeding EP 08001713.0, date indicated as Mar. 18, 2020, 4 pages.
EP37 Annex to the communication—opposition—in EP proceeding EP 08001713.0, date indicated as Mar. 18, 2020, 3 pages.
EP38 dated Apr. 29, 2020 Board's composition—in EP proceeding EP 08001713.0, date indicated as Apr. 29, 2020, 1 page.
EP39 dated Jun. 18, 2020 Board's communication—in EP proceeding EP 08001713.0, date indicated as Jun. 18, 2020, 1 page.
EP40 dated Jun. 26, 2020 summons—in EP proceeding EP 08001713.0, date indicated as Jun. 26, 2020, 2 pages.
EP41 dated Jun. 26, 2020 communication—in EP proceeding EP 08001713.0, date indicated as Jun. 26, 2020, 2 pages.
EP42 F3303.16 Change of composition of the Board (T)—in EP proceeding EP 08001713.0, date indicated as Feb. 18, 2021, 1 page.
EP43 3326_2021-03-01_1—in EP proceeding EP 08001713.0, date indicated as Mar. 1, 2021, 7 pages.
EP44 F3305 Communication of the Board of Appeal (ex parte inter partes)—in EP proceeding EP 08001713.0, date indicated as Apr. 20, 2021, 37 pages.
EP45 complaint CRM 823119-2021 signed reply—in EP proceeding EP 08001713.0, date indicated as Jun. 10, 2021, 2 pages.
EP46 Communication including corrected minutes—in EP proceeding EP 08001713.0, date indicated as Jun. 29, 2021, 51 pages.
EP48 Communication of the Registry—EPO Form 3004, in EP Application No. 08001713.0, Patent No. 1953527, dated Oct. 15, 2021, 1 page.
EP49 Decision, Board of Appeal, in EP Application No. 08001713.0, Patent No. 1953527, dated Dec. 14, 2021, 75 pages.
Summons to Attend Oral Proceedings Pursuant to Rule 115(1) EPC, in EP Application No. 20159741.6, dated Oct. 19, 2021, 6 pages.
CSR4-1 and CSR4-2, Attorney's Opinion as filed Oct. 29, 2021, document(s) dated Oct. 29, 2021, including English translation, 38 pages.
CSR5-1 and CSR5-2, Documents as filed Nov. 9, 2021, document(s) dated Nov. 9, 2021, including English translation, 9 pages.
CSR6-1 and CSR6-2, Attorney's opinion, Post-Hearing Observation, dated Nov. 30, 2021, document(s) dated Nov. 30, 2021, including English translation, 21 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: 2021 01 29 BCI Supplemental ID of Initial Invalidity References w Appendix A, dated Jan. 29, 2021, 8 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: Jun. 25, 2021 Expert Report of J. Paul Robinson, dated Jun. 25, 2021, 608 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: Jun. 25, 2021 Rebuttal Expert Report of Vijay Madisetti, dated Jun. 25, 2021, 35 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: May 7, 2021 BCI Final Invalidity Contentions—List of prior art references, dated May 7, 2021, 5 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: May 7, 2021 BCI Final Invalidity Contentions, dated May 7, 2021, 191 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: 510(k) No. K061150, dated Jul. 6, 2006, Exhibit DDX-083, dated Jan. 28, 2021, 5 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: Advia 2120-2120i Operator's Guide, Exhibit PDX 180, dated Aug. 5, 2021, 951 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: An Evaluation of the Cell-Dyn3200 for Counting Cells in Cerebrospinal and Body Fluids, (Andrews), date accepted Dec. 13, 2004, D14, 9 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: An Evaluation of the Utility of Performing Body Fluid Counts on the Coulter LH750(Barnes), date accepted Mar. 30, 2004, 5 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: Automated Counting of Cells in Cerebrospinal Fluid CellDyn4000 Haematology Analyser (Hoffmann), dated 2002, 8 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB Automated Counting of White Blood Cells in Synovial Fluid (deJong), dated Oct. 1, 2003, 4 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB Automated Flow Cytometric Analysis of Cerebrospinal Fluid, (Van Acker et al.), dated 2001,5 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB Automated Flow Cytometric of Blood Cells in Cerebrospinal Fluid, Analytic Performance, dated 2004, obtained Mar. 17, 2020, 11 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: Body Fluid Analysis for Cellular Composition, Approved Guideline, dated 2006, 112 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: Body Fluids, 3rd Edition (Kjeldsberg et al.), dated 1992, 23 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB Cholesterol Crystals Causing Falsely Elevated Automated Cell Count (Shen), dated 2006, 6 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: Coulter LH 700 Series System, Oct. 2003, D3, 114 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: Coulter LH Series Workstation Body Fluid Application-Operator's Guide, Sep. 2004, D2, 48 pages.

(56) References Cited

OTHER PUBLICATIONS

Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB Evaluation of the Abbott CELL-DYN 4000 Hematology Analyzer (Grimaldi and Scopacasa), date downloaded Apr. 27, 2018, 9 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB Leukocyte Counts Cerebrospinal Fluid Automated Hematology Analyzer (Ziebig et al.), dated 2000, 6 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB Leukocyte Counts in Cerebrospinal Fluid with Automated Hematology Analyzer, Technicon H3 (Soogarun), dated 2002, 7 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB Measurement of total and differential white blood cell counts in synovial fluid by means of an automated hematology analyzer (Sugiuchi), dated 2005, 7 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB Operator's Manual - Automated Hematology Analyzer-XE-2100 Main Unit, 2005, 273 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB Performance Eval ADVIA2120 Hematology Analyzeran International Multicenter Clinical Trial (Harris), dated 2005, 9 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB Performance Eval of Automated leucocyte Counting in Cerebrospinal Fluid, (Schroeder) dated 2004, 5 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: BB20-Performance Eval of Automated leucocyte Counting in Cerebrospinal Fluid, dated 2005, 9 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB Premarket Notification, 510(k) No. K040073, Mar. 18, 2004, 107 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: Rule based processing of the CD4000, CD3200 and CD Sapphire analyser (Burgess), date accepted for publication May 29, 2008, 12 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: Use of the Advia 120 Hematology Analyzer in the Differential Cytologic—Analysis of Biological Fluids (Aulesa), dated 2003, 11 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: Validation of Body Fluid Analysis on the Coulter LH 750 (Brown), dated 2003, 5 pages.
Document(s) from U.S. District Court for the District of Delaware, *Sysmex Corporation* and *Sysmex America, Inc.* , Plaintiffs, v. *Beckman Coulter, Inc.*, C.A. No.: 19-1642-RGA-CJB: XE-2100, Automated Hematology Analyser, Instructions for Use, 2004, 255 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: BB27-XE-5000, Automated Hematology Analyzer, Instructions for Use, 2006, 265 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: XE-Series Body Fluid Application, 2004, 2 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: Expert Report of John W. Roche, dated Jun. 1, 2021, 122 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: Exhibit A, John Roche, dated 2021, 5 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: Exhibit B, Materials Considered, dated 2021, 5 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: Exhibit G, Comparison, dated 2021, 38 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: Exhibit H, Comparison, dated 2021, 41 dates.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB (BCID001259) Ford, NewQC, parameters, and automation for hematology analyzers, Dec. 2006, 13 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB (BCID001372), Hematology analyzers, Dec. 2009, 13 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB (BCID001643-BCID001749), 510(k) Summary of Safety and Effectiveness, Mar. 18, 2004, 107 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB (BCID235102-BCID235200), Bayer 510(k): Advia 120Hematology System, 2003, 99 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB Department of Health and Human Services, Re: K040073, Mar. 18, 2004, 66 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: Sysmex, Growing Globally: Three Core Strategies Lead the Way, Annual Report 2006, 68 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: 2020 10 14 (131) Amended Joint Claim Construction Chart, dated Oct. 14, 2020, 25 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: Apr. 6, 2021 (230) Report and Recommendation regarding claim construction, dated Apr. 6, 2021, 36 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: Advia-OG (BCID233031-BCID233981), Advia 2120, Advia2120i, 2007, 951 pages.

(56) References Cited

OTHER PUBLICATIONS

Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: Andrews, An Evaluation of the Cell-Dyn 3200 for Counting Cells in Cerebrospinal and Body Fluids (BCID001448), D14, 2005, 9 pages.

Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: Aulesa, Use of the Advia 120 Hematology Analyzer in the Differential Cytologic (BCID001457), 2003, 11 pages.

Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: Aune, M.W., et al., Automated Flow Cytometric Analysis of Blood Cells in Cerebrospinal Fluid, Analytic Performance, 2004, 11 pages.

Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: Barnes, An Evaluation of the Utility of Performing Body Fluid Counts on the Coulter LH750 (BCID001479), 2004, 5 pages.

Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: Brown, Validation of Body Fluid Analysis on the Coulter LH 750 (BCID001484), 2003, 5 pages.

Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: de Jonge, Automated Counting of white blood cells in synovial fluid, Rheumatology, 2004, 4 pages.

Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: Harris, Performance Eval ADVIA 2120 Hematology Analyzer an International Multicenter Clinical Trial (BCID001626), 2005, 9 pages.

Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB Hoffmann, Automated Counting of Cells in Cerebrospinal Fluid CellDyn4000 Haematology Analyser (BCID001635), 2002, 8 pages.

Document(s) from U.S. District Court for the District of Delaware, *Sysmex Corporation* and *Sysmex America, Inc.* , Plaintiffs, v. *Beckman Coulter, Inc.*, Plaintiffs, v. Beckman Coulter, Inc., Defendant., C.A. No.: 19-1642-RGA-CJB: Kresie, Performance Evaluation Application of BF on Sysmex XE-2100 Automated Hematology Analyzer (BCID001773), 2005, 9 pages.

Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: LH-OG (BCID234762-BCID234925), Coulter LH 700 Series System, Operator's Guide, 2003, 164 pages.

Document(s) from U.S. District Court for the District of Delaware, *Sysmex Corporation* and *Sysmex America, Inc.* , Plaintiffs, v. *Beckman Coulter, Inc.*, Defendant., C.A. No. 19-1642-RGA-CJB: LH-OM (BCID234532-BCID234645), Coulter LH 700 Series System, 2003, 114 pages.

Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB Soogarun, Leukocyte Counts in Cerebrospinal Fluid with Automated Hematology Analyzer Technicon H3 (BCID001955), 2002, 7 pages.

Document(s) from U.S. District Court for the District of Delaware, *Sysmex Corporation* and *Sysmex America, Inc.* , Plaintiffs, v. *Beckman Coulter, Inc.*, Defendant., C.A. No. 19-1642-RGA-CJB: Sugiuchi et al., Measurement of total and differential white blood cell counts in synovial fluid by means of an automated hematology analyzer, 2005, 7 pages. (BCID001962).

Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: XE-IPU (SCorp-Del00257516), Operator's Manual, Automated Hematology Analyzer, XE-2100 IPU (Information Processing Unit) (North American Edition), Apr. 2004, 293 pages.

Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: XE-OM (BCID002229-BCID002501), Operator's Manual, Automated Hematology Analyzer, XE-2100 Main Unit, Mar. 2005, 273 pages.

Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: Exhibit A, Instructions for use, UniCel DxH Series with System Manager Software, Aug. 2014, 993 pages.

Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: Exhibit B Beckman Coulter Performing Complete Blood Count with WBC Differential, Nucleated Red Blood Cell, Reticulocyte and Body Fluids cell counting on the UniCel DxH 800 and UniCel DxH 600 Coulter Cellular Analysis Systems, 2015, 40 pages.

Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: Exhibit C Performance Evaluation of Body Fluids, 2009, 9 pages.

Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: Exhibit D, Rou Addendum, Jul. 2015, 47 pages.

Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: Exhibit E, Training Pocket Resources, 2017, 77 pages.

Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: Exhibit F, Technical Testing of a Beckman Coulter DxH 800 (HE 26—Test Report DxH800), 2015, 67 pages.

Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: Exhibit G (K081930 DxH 800 decision summary), Dec. 19, 2008, dated Dec. 19, 2008, 10 pages.

Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: Exhibit H (Class 1 Device Recall Unicell DxH 600), 2019, 4 pages.

Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: Exhibit I (Class 1 Device Recall UniCel DxH 900), 2020, 6 pages.

Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: Exhibit J (Instructions for use DxH 900), 2017, 797 pages.

Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: Exhibit K (Rou Addendum DxH 900), 2017, 29 pages.

Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: Exhibit L (K120771 FDA predicate for v 3.0 identifies three modes), 510(k) Substantial Equivalence Determination Decision Summary, Mar. 22, 2013, Mar. 22, 2013, 20 pages.

Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB:

(56) References Cited

OTHER PUBLICATIONS

Exhibit M (K140911-1 DxH 800 3.0, 510(k) Substantial Equivalence Determination Decision Summary, Sep. 5, 2014, Sep. 5, 2014, 21 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: Exhibit N B26647AG, Instructions for Use UniCel DxH Series with System Manager Software, 2020, 1027 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: Exhibit O C06947AC, Instructions for Use, UniCel DxH 900 Series with System Manager Software, 2019, 819 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: Exhibit P C11340AB, Ruo Addendum, UniCel DxH 900 Series with System Manager Software Coulter Cellular Analysis System, 2019, 29 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: Exhibit 1004—XE2100 Main Unit, 2004, 273 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: Exhibit 1005—XE-Series, Body Fluid Application, 2004, 2 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: Exhibit 1012—U.S. Pat. No. 5,888,752, Mar. 30, 1999, 12 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: Exhibit 1032—Schroeder, Performance Evaluation of Automated Leucocyte Counting in Cerebrospinal Fluid (CSF) by the XE-2100 Compared to Manual Counting, 2004, 5 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: Exhibit 1034—K030606, Section 1 D: 510(k) Summary of Safety and Effectiveness for Coulter LH750 Body Fluids Application, Feb. 24, 2003, 5 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: Exhibit 1041—XE-2100 Flyer, Haematology is Fluorescence Flow Cytometry, 2005, 2 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: DDX-0036, Tadashi Horie 011521, dated Jan. 15, 2021, 293 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: DDX-0093 Takaaki Nagai, vol. II 020321, dated Feb. 3, 2021, 431 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: DDX-0094 Takaaki Nagai, vol. II 020321, dated Feb. 3, 2021, 14 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: DDX-0136 Daigo Fukuma 033021, dated Mar. 30, 2021, 30 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: DDX-0139 Daigo Fukuma 30(b)(6) vol. II 033121, dated Mar. 31, 2021, 1 page.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: Pdx 0001 Eric Grace 120820, U.S. Pat. No. 10,401,350, dated Sep. 3, 2019, exhibit dated Dec. 8, 2020, 33 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: PDX 0002 Eric Grace 120820, U.S. Pat. No. 10,401,351, dated Sep. 3, 2019, exhibit dated Dec. 8, 2020, 34 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: PDX 0033, Exhibit B, Douglas Dunbabin, Dec. 10, 2020, dated Dec. 10, 2020, 40 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: Exhibit A, PDX 0034, dated Dec. 10, 2020, 993 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: PDX 0035, dated Dec. 10, 2020, 76 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: PDX 0118, dated Jan. 29, 2021, 10 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: Pdx 001, U.S. Pat. No. 10,401,350, dated Sep. 3, 2019, 33 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: PDX 002, U.S. Pat. No. 10,401,351, dated Sep. 3, 2019, 34 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: PDX 003, D25, Declaration of Douglas Drew Dunbabin, dated Dec. 8, 2020, 2 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: PDX 004, D2, Operator's G, uide, Coulter LH Series Workstation, Body Fluid Application, dated Dec. 8, 2020, 48 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: PDX 005, D3, Coulter LH 700 Series System, 114 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: PDX 006, D29, Declaration of Eric Grace, dated Dec. 8, 2020, 3 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: PDX 007, D30, dated Dec. 8, 2020, 3 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: PDX 008, D35, Declaration of Eric Grace, dated Dec. 8, 2020, 4 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: PDX 009, Declaration of Douglas Drew Dunbabin, D16, dated Dec. 8, 2020, 22 pages.
Document(s) from U.S. District Court for the District of Delaware, *Sysmex Corporation* and *Sysmex America, Inc.*, Plaintiffs, v.

(56) References Cited

OTHER PUBLICATIONS

*Beckman Coulter, Inc.*, Defendant., C.A. No.: 19-1642-RGA-CJB: PDX 010, Declaration of Eric Grace, dated Dec. 8, 2020, 16 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: PDX 012, Beckman Coulter, Coulter LH750 Body Fluid Application, dated Dec. 8, 2020, 3 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: PDX 013, dated Dec. 8, 2020, 2 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: PDX 014, Operator's Manual Automated Hematology Analyzer, XE-2100 Main Unit, dated 2005, 273 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: PDX 015, XE-Series, Body Fluid Application, dated Dec. 8, 2020, 2 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: PDX 018, Product: Mid Volume Segment, dated Dec. 8, 2020, 3 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: PDX 018, dated Jun. 22, 2017, by Eric Grace, Product: Mid Volume Segment, 1 page.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: PDX 019, K081930, 510(k) Summary, UniCel DxH 800 Coulter Cellular Analysis System, dated Dec. 19, 2008, Exhibit date Dec. 8, 2020, 9 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: PDX 023, K120771, Beckman Coulter, Abbreviated 510(k) Summary for the Beckman Coulter UniCel DxH 800 Coulter Cellular Analysis System, dated Mar. 22, 2013, Exhibit date Dec. 8, 2020, 25 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: PDX 0130, dated Apr. 6, 2021, 13 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: Pdx 0134, Coulter LH 750 Hematology Analyzer, Coulter LH 780 Hematology Analyzer, Coulter LH Slidemaker, Coulter LH Slidestainer, Training Guide, dated Apr. 6, 2021, 167 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: PDX 0135, Exhibit D, dated Apr. 6, 2021, 47 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: PDX 0136, dated Apr. 6, 2021, 11 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: PDX 0139A, Beckman Coulter Beckman Coulter Haematology Analyzer Comparison Tool, dated Apr. 6, 2021, 11 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: PDX 0139A, Eric Grace, dated Apr. 6, 2021, 1 page.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: DDX 0034, Operator's Manual, Automated Hematology Analyzer, XE-2100 Main Unit, dated Jan. 15, 2021, 273 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: DDX 0035, dated Jan. 15, 2021, 40 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: DDX 0036, Operator's Manual, Automated Hematology Analyzer, XE-2100 IPU, dated Jan. 15, 2021, 293 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: DDX 0037, XE-Series, Body Fluid Application, dated Jan. 15, 2021, 2 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: DDX 0040, XT-Series, Body Fluid Application, dated Jan. 15, 2021, 2 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: DDX 0089, U.S. Pat. No. 8,841,117, dated Sep. 23, 2014, exhibit date Feb. 3, 2021, 27 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: DDX 0090, U.S. Pat. No. 9,243,993 B2, dated Jan. 26, 2016, exhibit date Feb. 3, 2021, 29 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: DDX 0091, Operator's Manual, Automated Hematology Analyzer, XE-2100 Main Unit, dated Feb. 3, 2021, 20 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: DDX 0093, Sysmex Automated Hematology Analyzer, XT-2000i/XT-1800i Instructions for Use, date last revised 2006, exhibit date Feb. 3, 2021, 431 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: DDX 0094, dated Jan. 19, 2021, exhibit date Feb. 3, 2021, 14 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: PDX 0001, U.S. Pat. No. 10,401,350, dated Sep. 3, 2019, exhibit date Dec. 8, 2020, 33 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: PDX 0002, U.S. Pat. No. 10,401,351, dated Sep. 3, 2019, exhibit date Dec. 8, 2020, 34 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: Noriyuki Narisada vol. I, dated Mar. 10, 2021, 48 pages.
Document(s) from U.S. District Court for the District of Delaware, *Sysmex Corporation* and *Sysmex America, Inc.* , Plaintiffs, v. *Beckman Coulter, Inc.*, Defendant., C.A. No.: 19-1642-RGA-CJB: Noriyuki Narisada, vol. II, dated Mar. 11, 2021, 62 pages.
Document(s) from U.S. District Court for the District of Delaware, *Sysmex Corporation* and *Sysmex America, Inc.* , Plaintiffs, v.

(56) References Cited

OTHER PUBLICATIONS

*Beckman Coulter, Inc.*, Defendant., C.A. No.: 19-1642-RGA-CJB: DDX 0033, Technical Testing of a Beckman Coulter LH 750, dated Jan. 15, 2021, 13 pages.
Document(s) from U.S. District Court for the District of Delaware, *Sysmex Corporation* and *Sysmex America, Inc.*, Plaintiffs, v. *Beckman Coulter, Inc.*, Defedant., C.A. CA. No.: 19-1642-RGA-CJB: DDX 0036, Operator's Manual, Automated Hematology Analyzer, XE-2100 Main Unit, dated Jan. 15, 2021, 273 pages.
Document(s) from U.S. District Court for the District of Delaware, *Sysmex Corporation* and *Sysmex America, Inc.*, Plaintiffs, v. *Beckman Coulter, Inc.*, Defedant., C.A. CA. No.: 19-1642-RGA-CJB: DDX 0036, Operator's Manual, Automated Hematology Analyzer, XE-2100 IPU, dated Jan. 15, 2021, 293 pages.
Document(s) from U.S. District Court for the District of Delaware, *Sysmex Corporation* and *Sysmex America, Inc.*, Plaintiffs, v. *Beckman Coulter, Inc.*, Defedant., C.A. CA. No.: 19-1642-RGA-CJB: DDX 0037, XW-Series, Body Fluid Application, dated Jan. 15, 2021, 2 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: DDX 0038, Department of Health & Human Services, dated Mar. 18, 2004, exhibit date Jan. 15, 2021, 66 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: DDX 0041, 510(k) Summary of Safety and Effectiveness, dated Jul. 6, 2006, exhibit date Jan. 15, 2021, 5 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: DDX 0093, Sysmex Automated Hematology Analyzer, XT-2000i/XT-1800i Instructions for Use, date of last revision: Jul. 2006, exhibit date Feb. 3, 2021, 431 pages.
Document(s) from U.S. District Court for the District of Delaware, *Sysmex Corporation* and *Sysmex America, Inc.*, Plaintiffs, v. *Beckman Coulter, Inc.*, Defendant., C.A. No.: 19-1642-RGA-CJB: DDX 0131, Inventor Oath/Declaration, date signed: Feb. 27, 2018, exhibit date Mar. 11, 2021, 1 page.
The People's Republic of China the Supreme People's Court Administrative Judgment (2021), Zui Gao Fa Zhi Xing Zhong 680 Appellant (Plaintiff of the original proceeding): Sysmex Corporation; Appellee (Defendant of the original proceeding): National Intellectual Property Administration, PRC; Original Third Party: Beckman Coulter Commercial Enterprise (China) Co., Ltd.; including English translation, dated Apr. 21, 2022, 114 pages.
Document(s) from *Sysmex Corporation* and *Sysmex America, Inc.* v. *Beckman Coulter, Inc.*, Dec. 10, 2021 (423) Redacted Version of 413 Opening Brief in Support by BCI, filed Dec. 10, 2021, 26 pages.
Document(s) from *Sysmex Corporation* and *Sysmex America, Inc.* v. *Beckman Coulter, Inc.*, Dec. 10, 2021 (424) Redacted Version of [411] BCI SJ Invalidity Opening Brief—Defendant Beckman Coulter, Inc.'s Opening Brief in Support of Its Motion for Summary Judgment of Invalidity, filed Dec. 10, 2021, 33 pages.
Document(s) from *Sysmex Corporation* and *Sysmex America, Inc.* v. *Beckman Coulter, Inc.*, Dec. 10, 2021 (425) REDACTED Version of [415] BCI Daubert Haas—Defendant Beckman Coulter, Inc.'s Opening Brief in Support of Its Daubert Motion to Exclude the Opinions of Plaintiffs' Damages Expert David Haas, filed Dec. 10, 2021, 17 pages.
Document(s) from *Sysmex Corporation* and *Sysmex America, Inc.* v. *Beckman Coulter, Inc.*, Dec. 10, 2021 (426) Redacted Version of 407 Opening Brief in Support by Sysmex-Sysmex Corporation and Sysmex America, Inc.'s Combined Opening Brief in Support of Its Motion for Partial Summary Judgment and Motion to Exclude Certain Opinions of John W. Roche and Mitchell B. Rosen, filed Dec. 10, 2021, 61 pages.
Document(s) from *Sysmex Corporation* and *Sysmex America, Inc.* v. *Beckman Coulter, Inc.*, Feb. 2, 2022 (464) Redacted Version of 408 Appendix by Sysmex-Plaintiffs' Compendium to Its Opening Brief in Support of Its Motion for Partial Summary Judgment and Motion to Exclude Certain Opinions of John W. Roche and Mitchell B. Rosen, including Exhibits 1-33, filed Feb. 2, 2022, 847 pages.
Document(s) from *Sysmex Corporation* and *Sysmex America, Inc.* v. *Beckman Coulter, Inc.*, Feb. 2, 2022 (465) Redacted Version of 409 Appendix by Sysmex, Plaintiffs' Compendium to Its Opening Brief in Support of Its Motion for Partial Summary Judgment and Motion to Exclude Certain Opinions of John W. Roche and Mitchell B. Rosen, including Exhibits 34-47, filed Feb. 2, 2022, 266 pages.
Document(s) from *Sysmex Corporation* and *Sysmex America, Inc.* v. *Beckman Coulter, Inc.*, Feb. 2, 2022 (466) Redacted Version of 437 Appendix by Sysmex-Sysmex Corporation and Sysmex America, Inc.'s Compendium in Support of Its Reply Brief in Support of Its Combined Motions for Partial Summary Judgment and Daubert Motion, including Exhibits 73-93, filed Feb. 2, 2022, 329 pages.
Document(s) from *Sysmex Corporation* and *Sysmex America, Inc.* v. *Beckman Coulter, Inc.*, Jan. 25, 2022 (444) Redacted Feng Declaration ISO Opening Briefs SJ and Daubert—Declaration of Wallace H. Feng in Support of Beckman Coulter, Inc.'s Opening Brief Excerpted Exhibits 1-44 (Relevant Excerpts of Exhibits 1-44 Originally filed as D.I. 416-420), filed Jan. 25, 2022, 8 pages.
Document(s) from *Sysmex Corporation* and *Sysmex America, Inc.* v. *Beckman Coulter, Inc.*, Jan. 25, 2022 (445) Redacted Feng Declaration ISO Opening Briefs (Originally Dkt 416-420)-Declaration of Wallace H. Feng in Support of Beckman Coulter, Inc.'s Opening Brief Excerpted Exhibits 1-44 KRelevant Excerpts of Exhibits 1-44 Originally filed as D.I. 416-420), filed Jan. 25, 2022, 93 pages.
Document(s) from *Sysmex Corporation* and *Sysmex America, Inc.* v. *Beckman Coulter, Inc.*, Jan. 25, 2022 (447) Redacted BCI Opp to Motion for Partial Summ. Judgment and Motion Exclude_Daubert—Defendant Beckman Coulter, Inc.'s Brief in Opposition to Plaintiffs Sysmex Corporation and Sysmex America, Inc.'s Motion for Partial Summary Judgment and Motion to Exclude Certain Opinions of John W. Roche and Mitchell B. Rosen, filed Jan. 25, 2022, 66 pages.
Document(s) from *Sysmex Corporation* and *Sysmex America, Inc.* v. *Beckman Coulter, Inc.*, Jan. 25, 2022 (451) Redacted Beckman Reply ISO MSJ Daubert—Defendant Beckman Coulter, Inc.'s Reply Brief in Support of Its Motion for Summary Judgment of Invalidity and Non-Infringement and Its Daubert Motion to Exclude the Opinions of Plaintiffs' Damages Expert David Haas, filed Jan. 25, 2022, 36 pages.
Document(s) from *Sysmex Corporation* and *Sysmex America, Inc.* v. *Beckman Coulter, Inc.*, Jan. 25, 2022 (452) Redacted Declaration of Feng ISO MSJ Daubert—Declaration of Wallace H. Feng in Support of Defendant Beckman Coulter, Inc.'s Reply Brief in Support of Its Motions for Summary Judgment of Invalidity and Non-Infringement and Its Daubert Motion to Exclude the Opinions of Plaintiffs' Damages Expert David Haas, filed Jan. 25, 2022, 89 pages.
Document(s) from *Sysmex Corporation* and *Sysmex America, Inc.* v. *Beckman Coulter, Inc.*, Jan. 25, 2022 (453) Redacted Sysmex Compendium vol. 1—Plaintiffs' Compendium to Its Opening Brief in Support of Its Motion for Partial Summary Judgment and Motion to Exclude Certain Opinions of John W. Roche and Mitchell B. Rosen, filed Jan. 25, 2022, 4 pages.
Document(s) from *Sysmex Corporation* and *Sysmex America, Inc.* v. *Beckman Coulter, Inc.*, Jan. 25, 2022 (454) Redacted Sysmex Compendium vol. 2—Plaintiffs' Compendium to Its Opening Brief in Support of Its Motion for Partial Summary Judgment and Motion to Exclude Certain Opinions of John W. Roche and Mitchell B. Rosen, filed Jan. 25, 2022, 4 pages.
Document(s) from *Sysmex Corporation* and *Sysmex America, Inc.* v. *Beckman Coulter, Inc.*, Jan. 25, 2022 (455) Redacted Sysmex AB in Opposition to SJ_Exclude-Sysmex Corporation and Sysmex America, Inc.'s Answering Brief in Opposition to Defendant's Motions for Summary Judgment and Exclusion of Expert Testimony Under Daubert, filed Jan. 25, 2022, 60 pages.
Document(s) from *Sysmex Corporation* and *Sysmex America, Inc.* v. *Beckman Coulter, Inc.*, Jan. 25, 2022 (456) Redacted Sysmex Compendium Ex 48-72—Sysmex Corporation and Sysmex America, Inc.'s Compendium in Support of Its Answering Brief in Opposition

(56) References Cited

OTHER PUBLICATIONS to Defendants' Motions for Summary Judgment and Exclusion of Expert Testimony Under Daubert, filed Jan. 25, 2022, 3 pages.

Document(s) from *Sysmex Corporation* and *Sysmex America, Inc.* v. *Beckman Coulter, Inc.*, Jan. 25, 2022 (457) Redacted Sysmex RB ISO SJ_Daubert-Sysmex Corporation and Sysmex America, Inc.'s Reply Brief in Support of Its Combined Motions for Partial Summary Judgment and Daubert Motion, filed Jan. 25, 2022, 36 pages.

Document(s) from *Sysmex Corporation* and *Sysmex America, Inc.* v. *Beckman Coulter, Inc.*, Feb. 22 2022 (472) Redacted Version of 416 Declaration of Feng, vols. 1.0, 1.1, 1.2, 1.3, 1.4, 1.5, 1.6—Declaration of Wallace H. Feng in Support of Beckman Coulter, Inc.'s Opening Briefs in Support of Its Motion for Summary Judgment of Non-Infringement and Invalidity and Its Daubert Motion to Exclude the Opinions of Plaintiffs' Expert David Haas, filed Feb. 22, 2022, 1364 pages.

Document(s) from *Sysmex Corporation* and *Sysmex America, Inc.* v. *Beckman Coulter, Inc.*, Feb. 22 2022 (473) Redacted Version of 417 Declaration of Feng, vols. 2.0, 2.1,2.2, 2.3, 2.4, 2.5, 2.6, 2.7, 2.8—Declaration of Wallace H. Feng in Support of Beckman Coulter, Inc.'s Opening Brief in Support of Its Motion for Summary Judgment of Non-lnfringement and Invalidity and Its Daubert Motion to Exclude the Opinions of Plaintiffs' Expert David Haas, filed Feb. 22, 2022, 1751 pages.

Document(s) from *Sysmex Corporation* and *Sysmex America, Inc.* v. *Beckman Coulter, Inc.*, Feb. 22 2022 (474) Redacted Version of 418 Declaration of Feng, vols. 2.0, 2.1,2.2, 2.3, 2.4—Declaration of Wallace H. Feng in Support of Beckman Coulter, Inc.'s Opening Briefs in Support of Its Motion for Summary Judgment of Non-Infringement and Invalidity and Its Daubert Motion to Exclude the Opinions of Plaintiffs' Expert David Haas, filed Feb. 22, 2022, 1307 pages.

Document(s) from *Sysmex Corporation* and *Sysmex America, Inc.* v. *Beckman Coulter, Inc.*, Feb. 22 2022 (475) Redacted Version of 419 Declaration of Feng, vols. 2.0, 2.1—Declaration of Wallace H. Feng in Support of Beckman Coulter, Inc.'s Opening Briefs in Support of Its Motion for Summary Judgment of Non-Infringement and Invalidity and Its Daubert Motion to Exclude the Opinions of Plaintiffs' Expert David Haas, filed Feb. 22, 2022, 1575 pages.

Document(s) from *Sysmex Corporation* and *Sysmex America, Inc.* v. *Beckman Coulter, Inc.*, Feb. 22 2022 (476) Redacted Version of 420 Declaration of Feng, vols. 2.0, 2.1, 2.2, 2.3, 2.4, 2.5, 2.6, 2.7, 2.8—Declaration of Wallace H. Feng in Support of Beckman Coulter, Inc.'s Opening Briefs in Support of Its Motion for Summary Judgment of Non-Infringement and Invalidity and Its Daubert Motion to Exclude the Opinions of Plaintiffs' Expert David Haas, filed Feb. 22, 2022, 781 pages.

| Manual | Next No. 1 | Num |
|---|---|---|
| CDNR | OP No. | OP |
| Measurement not possible | | Xm |

120 — <manual sample number input>

121 — Sample number    1

Mode  1    2    3
      manual capillary closed

Discrete
122 —    1    2    3    4    5    6    7
      CBC CBC CBC CBC CBC CBC CBC
              DIFF DIFF     DIFF DIFF
123 —     NRBC              NRBC NRBC
                    RET RET     RET Sample 1: Normal  2: HPC  3: Body Fluid

Fig.8

| Example 1 | | | Example 2 | | | Example 3 | | |
|---|---|---|---|---|---|---|---|---|
| | Ref | This Method | | Ref | This Method | | Ref | This Method |
| WBC | 4580 | 4364 | WBC | 1370 | 1160 | WBC | 1360 | 1391 |
| Others | 1420 | 1387 | Others | 670 | 535 | Others | 70 | 74 |

SAMPLE ANALYZER AND COMPUTER PROGRAM PRODUCT

This application is a Divisional of U.S. application Ser. No. 15/908,339 filed Feb. 28, 2018, which is a Continuation of U.S. application Ser. No. 14/595,319 filed Jan. 13, 2015, now U.S. Pat. No. 9,933,414, which is a Continuation of U.S. application Ser. No. 13/891,667 filed May 10, 2013, now U.S. Pat. No. 8,968,661, which is a Continuation of U.S. application Ser. No. 12/023,830 filed Jan. 31, 2008, now U.S. Pat. No. 8,440,140, claiming priority to Japanese Application No. 2007-022523 filed on Feb. 1, 2007 and to Japanese Application No. 2007-095226 filed on Mar. 30, 2007, all of which are incorporated herein by reference in their entireties.

FIELD OF THE INVENTION

The present invention relates to a sample analyzer and a computer program product capable of measuring not only blood, but also body fluids other than blood such as cerebrospinal fluid (spinal fluid), fluid of the thoracic cavity (pleural fluid), abdominal fluid and the like.

BACKGROUND

In the field of clinical examinations, blood is routinely collected from a body and used as a sample which is measured by a sample analyzer to aid diagnosis and monitor treatment. Furthermore, body fluids other than blood are also often used as samples which are measured by a sample analyzer. The body fluids are usually transparent and contain very few cells, however, cells such as bacteria, abnormal cells, and hemorrhage (blood cells) and the like may be found in cases of disease, tumors of related organs, and injury.

When cerebrospinal fluid, which is one type of body fluid, is measured, for example, it is possible to make the following estimations from the measurement results.

Increase of red blood cells: subarachnoidal hemorrhage
Increase of neutrophils: meningitis
Increase of eosinophils: infectious disease (parasites and fungus)
Increase of monocytes: tuberculous meningitis, viral meningitis
Other cells: advanced meningeal tumor Japanese Laid-Open Patent Publication No. 2003-344393 discloses a blood cell analyzer which is capable of measuring cells in a body fluid. In Japanese Laid-Open Patent Publication No. 2003-344393, an operator prepares a measurement sample prior to performing the measurements by mixing a fluid sample and reagent (aldehyde, surface active agent, and cyclodextrin) in order to stably store the body fluid for a long period, and this measurement sample is later subjected to fluid analysis by the sample analyzer.

In the art of Japanese Laid-Open Patent Publication No. 2003-344393, however, the measurement sample is not prepared by the sample analyzer when the body fluid is measured, rather the measurement sample must be prepared by the operator of the analyzer. Furthermore, the sample analyzer disclosed in Japanese Laid-Open Patent Publication No. 2003-344393 does not disclose measurement operations suited to the fluid when measuring a body fluid.

SUMMARY OF THE INVENTION

The scope of the present invention is defined solely by the appended claims, and is not affected to any degree by the statements within this summary.

A first aspect of the present invention is a sample analyzer comprising: a measuring part for preparing a measurement sample from a blood sample or a body fluid sample that differs from the blood sample, measuring the prepared measurement sample, and obtaining characteristic information representing characteristics of components within the measurement sample; a mode setting means for setting either a blood measurement mode for measuring the blood sample, or a body fluid measurement mode for measuring the body fluid sample as an operating mode; a first control means for controlling the measuring part so as to execute operations in the blood measurement mode when the blood measurement mode has been set by the mode setting means; and a second control means for controlling the measuring part so as to execute operations in the body fluid measurement mode which differs from the operations in the blood measurement mode when the body fluid measurement mode has been set by the mode setting means.

A second aspect of the present invention is a sample analyzer comprising: a measuring part for preparing a measurement sample from a blood sample or a body fluid sample that differs from the blood sample, measuring the prepared measurement sample, and obtaining characteristic information representing characteristics of components within the measurement sample; a mode setting means for setting either a blood measurement mode for measuring the blood sample, or a body fluid measurement mode for measuring the body fluid sample as an operating mode; a first analyzing means for executing a first analysis process based on the characteristic information obtained by measuring the measurement sample prepared by the measuring part from the blood sample when the blood measurement mode has been set by the mode setting means; and a second analyzing means for executing a second analysis process which differs from the first analysis process baaed on the characteristic information obtained by measuring the measurement sample prepared by the measuring part from the body fluid sample when the body fluid measurement mode has been set by the mode setting means.

A third aspect of the present invention is a sample analyzer comprising: a measuring part for preparing a measurement sample from a blood sample or a body fluid sample that differs from the blood sample, measuring the prepared measurement sample, and obtaining characteristic information representing characteristics of components within the measurement sample; a mode switching means for switching an operating mode from a blood measurement mode for measuring the blood sample to a body fluid measurement mode for measuring the body fluid sample; and a blank measurement controlling means for controlling the measuring part so as to measure a blank sample that contains neither the blood sample nor the body fluid sample when the mode switching means has switched the operating mode from the blood measurement mode to the body fluid measurement mode.

A fourth aspect of the present invention is a computer program product, comprising: a computer readable medium; and instructions, on the computer readable medium, adapted to enable a general purpose computer to perform operations, comprising a step of preparing a measurement sample from a blood sample or a body fluid sample which differs from the blood sample; a step of measuring the prepared measurement sample; a step of obtaining characteristic information representing characteristics of the components in the measurement sample; a step of setting either a blood measurement mode for measuring the blood sample, or a body fluid measurement mode for measuring the body fluid sample as an operating mode; and a step of measuring the measurement sample prepared from the blood sample by executing operations in the blood measurement mode when the blood measurement mode has been set, and measuring the measurement sample prepared from the body fluid sample by executing operations in the body fluid measurement mode that differs from the operations in the blood measurement mode when the body fluid measurement mode has been set.

BRIEF DESCRIPTION OF THE DRAWINGS

FIG. 8 shows the display screen for setting the measurement mode;
FIG. 11 compares measurement results by the blood cell analyzer of the embodiment and measurement results by a reference method;
FIG. 16 is a display screen showing the measurement results in the body fluid measurement mode.

DETAILED DESCRIPTION OF THE PREFERRED EMBODIMENTS

The preferred embodiments of the present invention will be described hereinafter with reference to the drawings.

Figure 1:
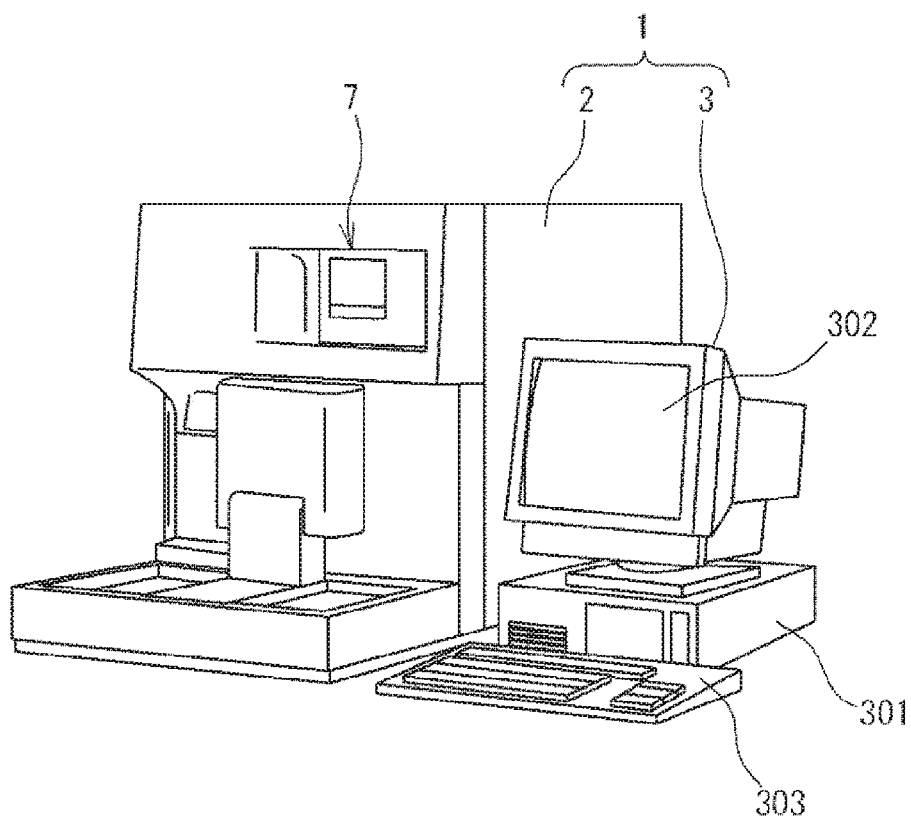
FIG. 1 is art exterior view of a blood cell analyzer of a first embodiment of the present invention.

FIG. 1 shows a sample analyzer 1. The sample analyzer 1 is configured as an automatic multi-item blood cell analyzer which performs blood analysis by measuring blood samples held in sample containers (blood collection tubes), obtaining characteristics information representing the characteristics of the blood cells contained in the sample, and analyzing the characteristic information. The sample analyzer 1 is also capable of analyzing body fluids. In the blood cell analyzer of the present embodiment, the body fluids used as analysis objects include, fluid within the body cavity other than blood. Specifically, cerebrospinal fluid (spinal fluid, CSF: fluid filling the ventricle or sublemmal cavity), fluid of the thoracic cavity (pleural fluid, PE: fluid collected in pleural cavity), abdominal fluid (fluid collected in the abdominal cavity), fluid of the cardiac sac (fluid collected in the cardiac sac), synovial fluid (fluid present in joints, synovial sac, peritenon) and the like. Among types of body fluid which can be analyzed are dialysate of peritoneal dialysis (CAPD), intraperitoneal rinse and the like. Cells are usually not observed in these body fluids, however, the fluids may contain blood cells, abnormal cells, and cells such as bacteria in the case of disease, tumor of related organs, or injury. For example, it is possible to clinically estimate the following from measurement results in the case of cerebrospinal fluid. For example, sub-arachnoidal hemorrhage is indicted when there is an increase of red blood cells, meningitis is indicated when there is an increase of neutrophils, infectious disease (parasitic and fungal) is indicated when there is an increase of eosinophils, tuberculous meningitis and viral meningitis are indicated when there is an increase of monocytes, and advanced meningeal tumor is indicated when there is an increase of other cells. ed In the case of abdominal and thoracic fluids, cancers may be indicated when analysis of finds nucleated cells other than blood cells, that is, the fluid contains nucleated cells of mesothelial cells, macrophages, tumor cells and the like.

The sample analyzer 1 is provided with a measuring unit 2 which has the function of measuring blood and body fluid samples, and a data processing unit 3 which obtains analysis results by processing the measurement results output from the measurement unit 2. The data processing unit 3 is provided with a control unit 301, a display unit 302, and an input unit 303. Although the measuring unit 2 and data processing unit 3 are separate devices in FIG. 1, the both may also be integrated in a single apparatus.

Figure 2:
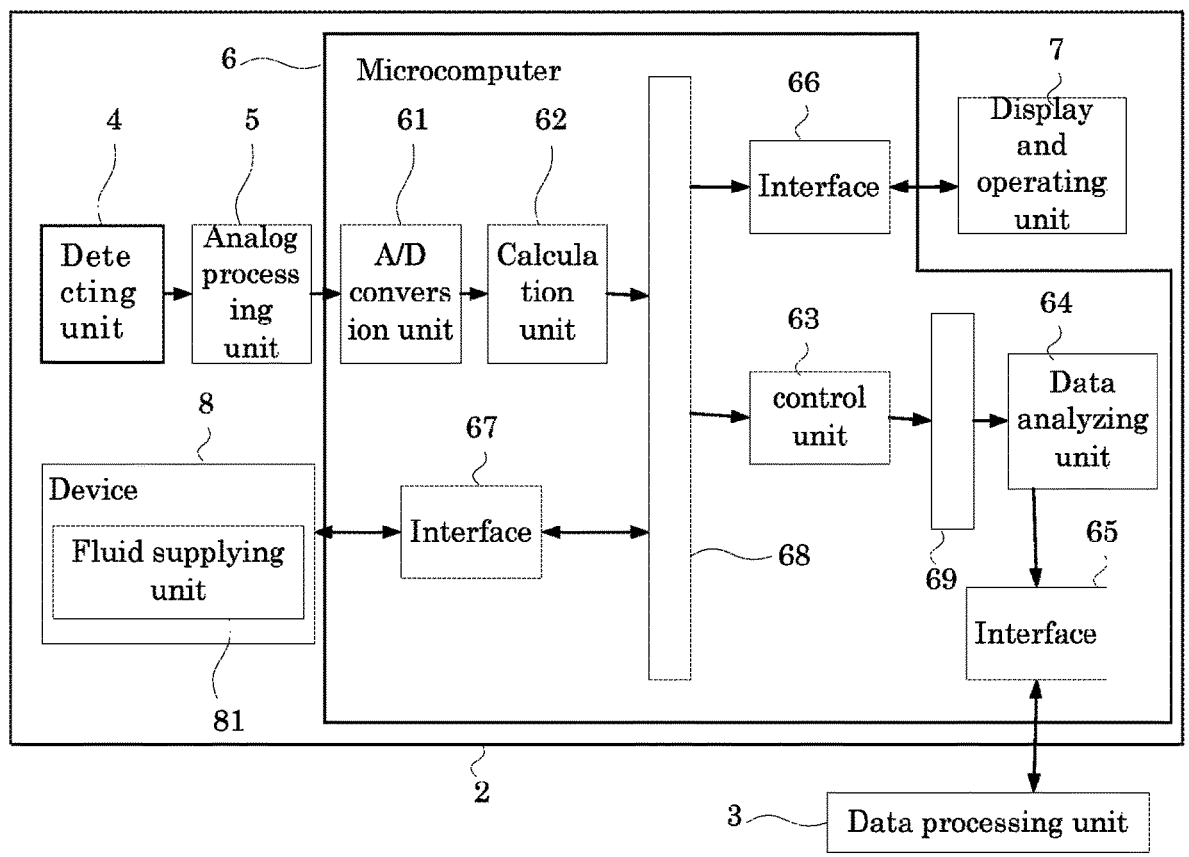
FIG. 2 is a block diagram of the measuring unit of the analyzer.

FIG. 2 is a block diagram of the measuring unit 2 of the analyzer 1. As shown in FIG. 2, the measuring unit 2 is provided with a blood cell detecting unit 4, an analog processing unit 5 which processes the output (analog signals) of the detecting unit 4, microcomputer unit 6, display and operating unit 7, and a device 8 for measuring blood and body fluids. The device 8 includes a fluid supplying unit 81 which is described below.

Figure 3:
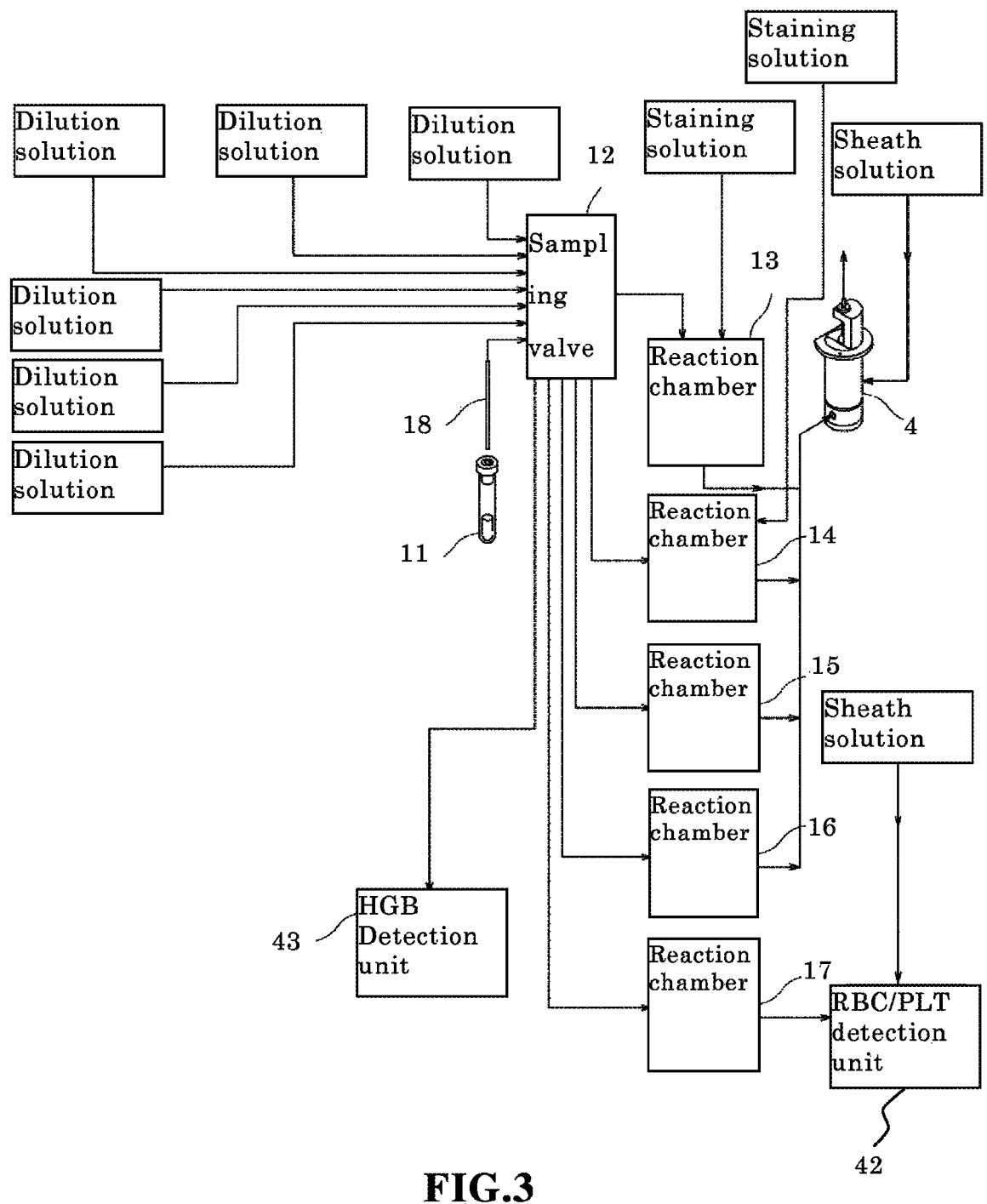
FIG. 3 is a block diagram of the fluid supplying unit.

FIG. 3 is a block diagram showing the structure of the fluid supplying unit 81. As shown in FIG. 3, the fluid supplying unit 81 is provided with a sample aspiration nozzle 18, a plurality of reagent containers, a sampling valve 12, and reactions chambers 13 through 17. The sample aspiration nozzle 18 aspirates sample from a sample container, and delivers the sample to the sampling valve 12. The sampling valve 12 divides the delivered sample into several aliquots of predetermined volume. The number of divisions differs depending on the mode of measurement (discrete mode); in the CBC mode the sample is divided into three aliquots to measure the number of red blood cells, the number of white blood cells, the number of platelets, and the hemoglobin concentration. In addition to the CBC measurement items, the sample is divided into four aliquots in the CBC-DIFF mode so as to also classify five types of white blood cells. Furthermore, in addition to the measurement items of the CBC+DIFF mode, the sample is divided into five aliquots in the CBC+DIFF+RET mode so as to also measure reticulocytes.

Similarly, in addition to the measurement items of the CBC+DIFF mode, the sample is divided into five aliquots in the CBC+DIFF+NRBC mode so as to also measure nucleated red blood cells. In addition to the measurement items of the CBC+DIFF+RET mode, the sample is divided into six aliquots in the CBC+DIFF+RET+NRBC mode so as to also measure nucleated red blood cells. The above mentioned measurement modes are blood measuring modes which measure whole blood. Finally, the sample is divided into two aliquots in the body fluid measuring mode for measuring body fluid.

Reagent (dilution solution) is introduced from a reagent container to the sampling valve, and the aliquots of the divided sample are delivered together with the reagent to the reaction chambers 13 through 17 and an HGB detection unit 43, which is described later, a predetermined amount of sample (aliquot) and a predetermined amount of reagent and a predetermined amount of stain collected by the sampling valve 12 are supplied to the reaction chamber 13 by a dosage pump which is not shown in the drawing, the sample and reagent are mixed to prepare a measurement, sample for four classifications of white blood cells (DIFF).

The reagent "stomatolyzer 4DL" made by Sysmex Corporation may be used as the dilution solution. This reagent contains surface active agent and induces hemolysis of red blood cells. The reagent "stomatolyzer 4DS" made by Sysmex Corporation may be used as the stain. This stain contains ethylene glycol, low molecular alcohol, and polymethane colorant; a 50× dilute sample is ultimately prepared by staining the blood cell component after hemolysis by the dilution agent.

When the body fluid measurement mode has been selected, a measurement sample for the classification of white blood cells is prepared from a fluid sample under the conditions of the amount of the sample and reagent used for the four classifications of white blood cells are identical, the reagents are identical, and the amounts of the reagent are identical. In the white blood cell classification of the body fluid measurement mode, the white blood cells are classified, not in four types, but two types, as shall be described later.

A predetermined amount of sample collected by the sampling valve 12, a predetermined amount of hemolytic dilution agent, and a predetermined amount of stain solution are supplied to the reaction chamber 14 by a dosage pump which is not shown in the drawing, the sample and reagents are then mixed to prepare a measurement sample for measuring nucleated red blood cells (NRBC).

A predetermined amount of sample collected by the sampling valve 12, a predetermined amount of dilution agent, and a predetermined amount of stain solution are supplied to the reaction chamber 15 by a dosage pump which is not shown in the drawing, the sample and reagents are then mixed to prepare a measurement sample for measuring reticulocytes (RET).

A predetermined amount of sample collected by the sampling valve 12, and a predetermined amount of hemolytic dilution agent are supplied to the reaction chamber 16 by a dosage pump which is not shown in the drawing, the sample and reagents are then mixed to prepare a measurement sample for measuring white blood cells and basophils (WBC/BASO).

A predetermined amount of sample collected by the sampling valve 12, and a predetermined amount of dilution solution are supplied to the reaction chamber 17 by a dosage pump which is not shown in the drawing, the sample and reagents are then mixed to prepare a measurement sample for measuring red blood cells and platelets (REC/PLT).

A predetermined amount of sample collected by the sampling valve 12, and a predetermined amount of hemolytic dilution agent are supplied to the HGB detection unit 43 which is described later.

The detection device 4 is provided with a white blood cell detection unit 41 for detecting white blood cells. The white blood cell detection unit 41 is also used to detect nucleated red blood cells and reticulocytes. In addition to the white blood cell detection unit, the detection device 4 is also provided with an RBC/PLT detection unit 42 for measuring the number of red blood cells and the number of platelets, and an HGB detection unit 43 for measuring the amount of pigment in the blood.

Figure 4:
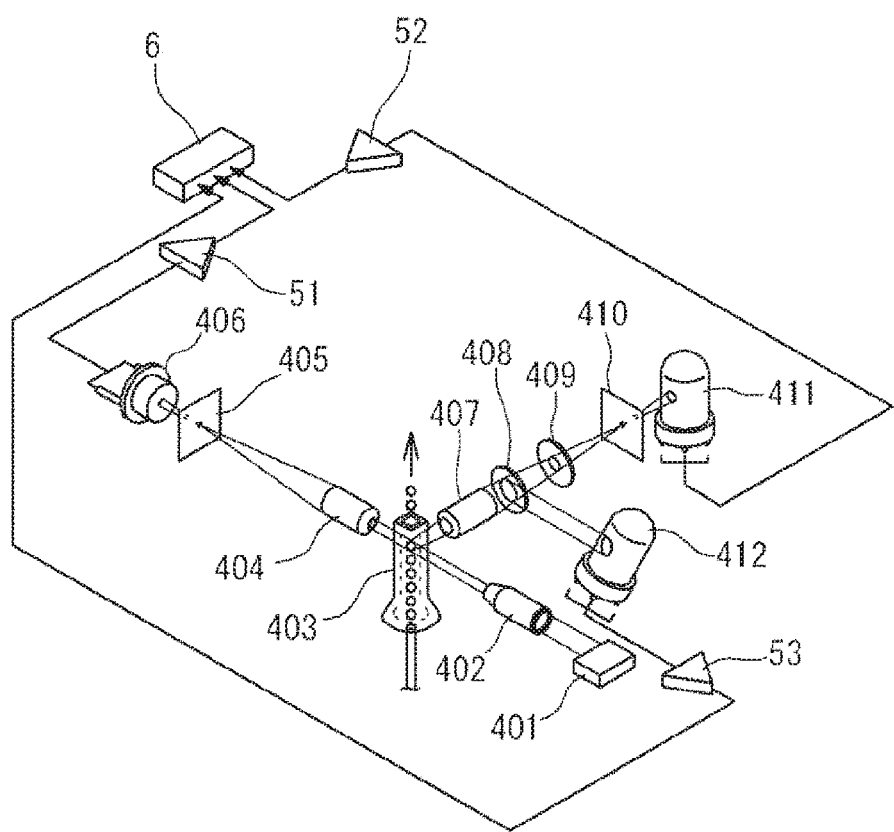
FIG. 4 shows the optical system of the white blood cell detection unit.

The white blood cell detection unit 41 is configured as an optical detection unit, specifically, a detection unit which uses a flow cytometric method. Cytometry measures the optical properties and physical properties of cells and other biological particles, and flow cytometry measures these particles as they pass by in a narrow flow. FIG. 4 shows the optical system of the white blood cell detection unit 41. In the same drawing, the beam emitted from a laser diode 401 irradiates, via a collimator lens 402, the blood cells passing through the interior of a sheath flow cell 403. The intensity of the front scattered light, the intensity of the side scattered light, and the intensity of the side fluorescent light from the blood cells within the sheath flow cell irradiated by the light are detected by the white blood cell detection unit 41.

The scattered light is a phenomenon due to the change in the direction of travel of the light caused by particles such as blood cells and the like which are present as obstructions in the direction of travel of the light. Information on the characteristics of the particles related to the size and composition of the particles can be obtained by detecting this scattered light. The front scattered light emerges from the particles in approximately the same direction as the direction of travel of the irradiating light. Characteristic information related to the size of the particle (blood cell) can be obtained from the front scattered light. The side scattered light emerges from the particle in an approximate perpendicular direction relative to the direction of travel of the irradiating light. Characteristic information related to the interior of the particle can be obtained from the side scattered light. When a particle is irradiated by laser light, the side scattered light intensity is dependent on the complexity (that is, nucleus shape, size, density, and granularity) of the interior of the cell, therefore, the blood cells can be classified (discriminated) and the number of cells can be counted by using the characteristics of the side scattered light intensity. Although the front scattered light and side scattered light are described as the scattered light used in the present embodiment, the present invention is not limited to this configuration inasmuch as scattered light of any angle may also be used relative to the optical axis of the light emitted from a light source that passes through the sheath flow cell insofar as scattered light signals are obtained which represent the characteristics of the particles necessary for analysis.

When fluorescent material such as a stained blood cell is irradiated by light, light is given off by the particle at a wavelength which is longer than the wavelength of the irradiating light. The intensity of the fluorescent light is increased by the stain, and characteristics information can be obtained relating to the degree of staining of the blood cell by measuring the fluorescent light intensity. The classification and other measurements of the white blood cells can then be performed by the difference in the (side) fluorescent light intensity.

As shown in FIG. 4, the front scattered light from the blood cell (white blood cells and nucleated red blood cells) which pass through the sheath flow cell 403 is received by a photodiode (front scattered light receiving unit) 406 through a collective lens 404 and pinhole 405. The side scattered light is received by a photo multiplexer (side scattered light receiving unit) 411 through a collective lens 407, dichroic mirror 408, optical filter 409, and pinhole 410. The side fluorescent light is received by a photo multiplexer (side fluorescent light receiving unit) 412 through the collective lens 407 and dichroic mirror 408. The photoreception signals output from the light receiving units 406, 411, and 412 are subjected to analog processing such us amplification and waveform processing and the like by an analog processing unit 5 which is configured by amps 51, 52, 53 and the like, and the analog-processed photoreception signals are provided to the microcomputer 6.

Figure 5:
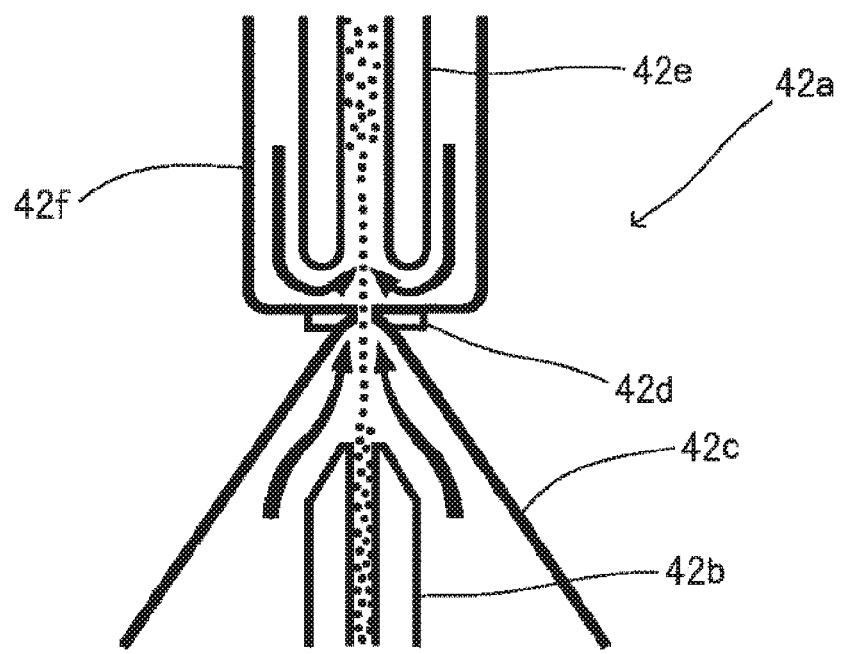
FIG. 5 shows the RBC/PLT detection unit.

The configuration of the RBC/PLT detection unit 42 is described below. FIG. 5 is a schematic view briefly showing the structure of the RBC/PLT detection unit 42. The RBC/PLT detection unit 42 is capable of measuring the numbers of red blood cells and platelets by a sheath flow-DC detection method. The RBC/PLT detection unit 42 has a sheath flow cell 42a as shown in FIG. 5. The sheath flow cell 42a is provided with a sample nozzle 42b which is open toward the top so that sample can be supplied from the reaction chamber 17 to the sample nozzle 42b. The sheath flow cell 42a has a tapered chamber 42c which narrows toward the top, and the sample nozzle 42b is disposed in the center part within the chamber 42c. An aperture 42d is provided at the top end of the chamber 42c, and this aperture 42d is aligned with the center position of the sample nozzle 42b. Measurement sample supplied from the sample supplying unit is sent upward from the tip of the sample nozzle 42b, and front sheath fluid is simultaneously supplied to the chamber 42c and flows upward toward the aperture 42d. The flow of the measurement sample, which is encapsulated in the front sheath fluid, is narrowly constricted by the tapered chamber 42c and the blood cells within the measurement sample pass one by one through the aperture 42d. Electrodes are provided at the aperture 42d, and a direct current is supplied between these electrodes. The change in the resistance of the direct current is detected at the aperture 42d when the measurement sample flows through the aperture 42d, and the electrical signal of the change in resistance is output to the controller 25. Since the resistance of the direct current increases when blood cells pass through the aperture 42d, the electrical signals reflect information of the passage of the blood cells through the aperture 42d so that the numbers of red blood cells and platelets can be counted by subjecting these electrical signals to signal processing.

A recovery tube 42e, which extends vertically, is provided above the aperture 42d. The recovery tube 42e is disposed within a chamber 42f which is connected to the chamber 42c through the aperture 42d. The inner wall of the chamber 42f is separated from the bottom end of the recovery tube 42e. The chamber 42f is configured to supply a back sheath, and this back sheath flows downward through the chamber 42f in a region outside the recovery tube 42e. The back sheath which flows outside the recovery tube 42e arrives at the bottom part of the chamber 42f, and thereafter flows between the inner wall of the chamber 42f and the bottom end of the recovery tube 42e so as to flow into the interior of the recovery tube 42e. The blood cells which has passed through the aperture 42d are therefore prevented from refluxing, thus preventing erroneous detection of the blood cells.

Figure 6:
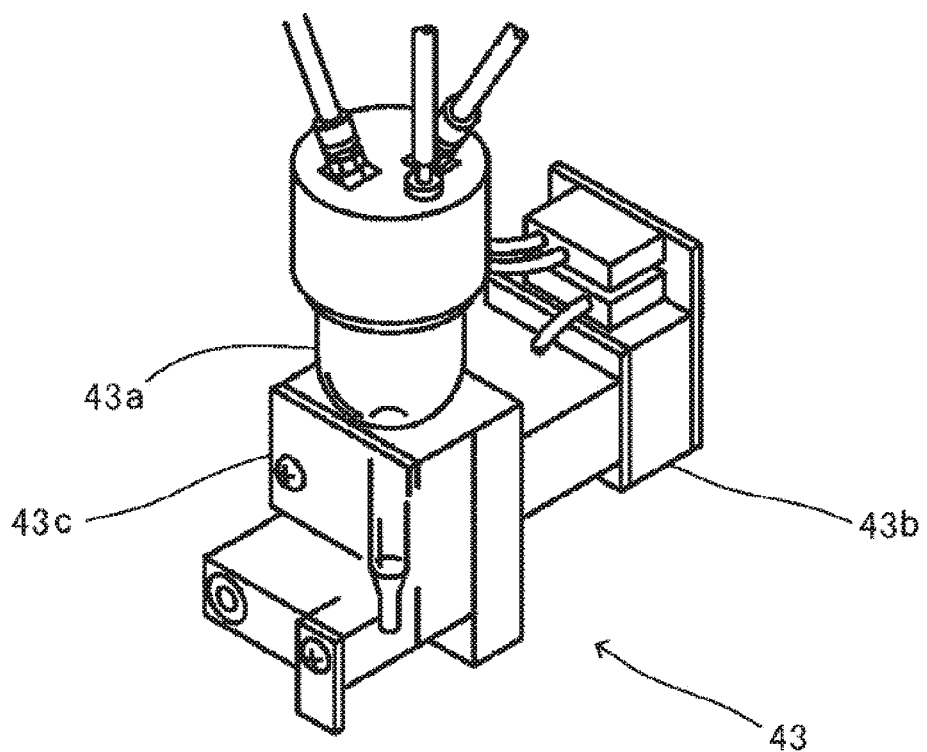
FIG. 6 shows the HGB detection unit.

The configuration of the HGB detection unit 43 is described below. The HGB detection unit 43 is capable of measuring the amount of hemoglobin (HGB) by an SLS hemoglobin method. FIG. 6 is a perspective view of the structure of the HGB detection unit 43. The HGB detection unit 43 has a cell 43a for accommodating a diluted sample, a light-emitting diode 43b for emitting light toward the cell 43a, and a photoreceptor element 43c for receiving the transmission light that has passed through the cell 43a. A fixed amount of blood is diluted with dilution fluid and a predetermined hemolytic agent at a predetermined dilution ratio by the sampling valve 12 to prepare a dilute sample.

The hemolytic agent has properties which transform the hemoglobin in the blood to SLS-hemoglobin. The dilute sample is supplied to the cell 43a and accommodated therein. In this condition, the light-emitting diode 43b emits light that passes through the cell 43a and is received by the photoreceptor element 43c which is disposed opposite the light-emitting diode 43b with the cell 43a interposed therebetween. Since the light-emitting diode 43b emits light having a wavelength that is highly absorbed by the SLS-hemoglobin, and the cell 43a is configured of plastic material which has a high light transmittancy, the photoreceptor element 43c only receives the transmission light absorbed by the dilute sample of the light emitted from the light-emitting diode 43b. The photoreceptor element 43c outputs electrical signals which correspond to the amount of received light (optical density) to the microcomputer 6, and the microcomputer 6 compares the optical density with the optical density of the dilution solution which was measured previously, then calculates the hemoglobing value.

The microcomputer 6 is provided with an A/D converter 61 for converting the analog signals received from the analog processing unit 5 to digital signals. The output of the A/D converter 61 is sent to a calculation unit 62 of the microcomputer 6, and calculations are performed for predetermined processing of the photoreception signals in the calculation unit 62. The calculation unit 62 prepares distribution data (two-dimensional scattergrams (unclassified) and unidimensional histograms) based on the output of the detection device 4.

The microcomputer 6 is provided with a controller 63 configured by a memory for the control processor and the operation of the control processor, and a data analyzing unit 64 configured by a memory for the analysis processor and the operation of the analysis processor. The controller 63 controls the device 8 configured by a sampler (not shown in the drawing) for automatically supplying blood collection tubes, and a fluid system and the like for preparing and measuring samples, as well as performing other controls. The data analyzing unit 64 executes analysis processing such as clustering and the like on the distribution data. The analysis results are sent to an external data processing device 3 through an interface 65, and the data processing device 3 processes the data for screen display, storage and the like.

The microcomputer 6 is further provided with an interface 66 which is interposed between the microcomputer 6 and the display and operating unit 7, and an interface 67 which is interposed between the microcomputer 6 and the device 8. The calculation unit 62, controller 63, and interfaces 66 and 67 are connected through a bus 68, and the controller 63 and the data analyzing unit 64 are connected through a bus 69. The display and operating unit 7 includes a start switch by which the operator specifies to start a measurement, and a touch panel type liquid crystal display for displaying various types of setting values and analysis results, and receiving input from the operator.

Figure 7:
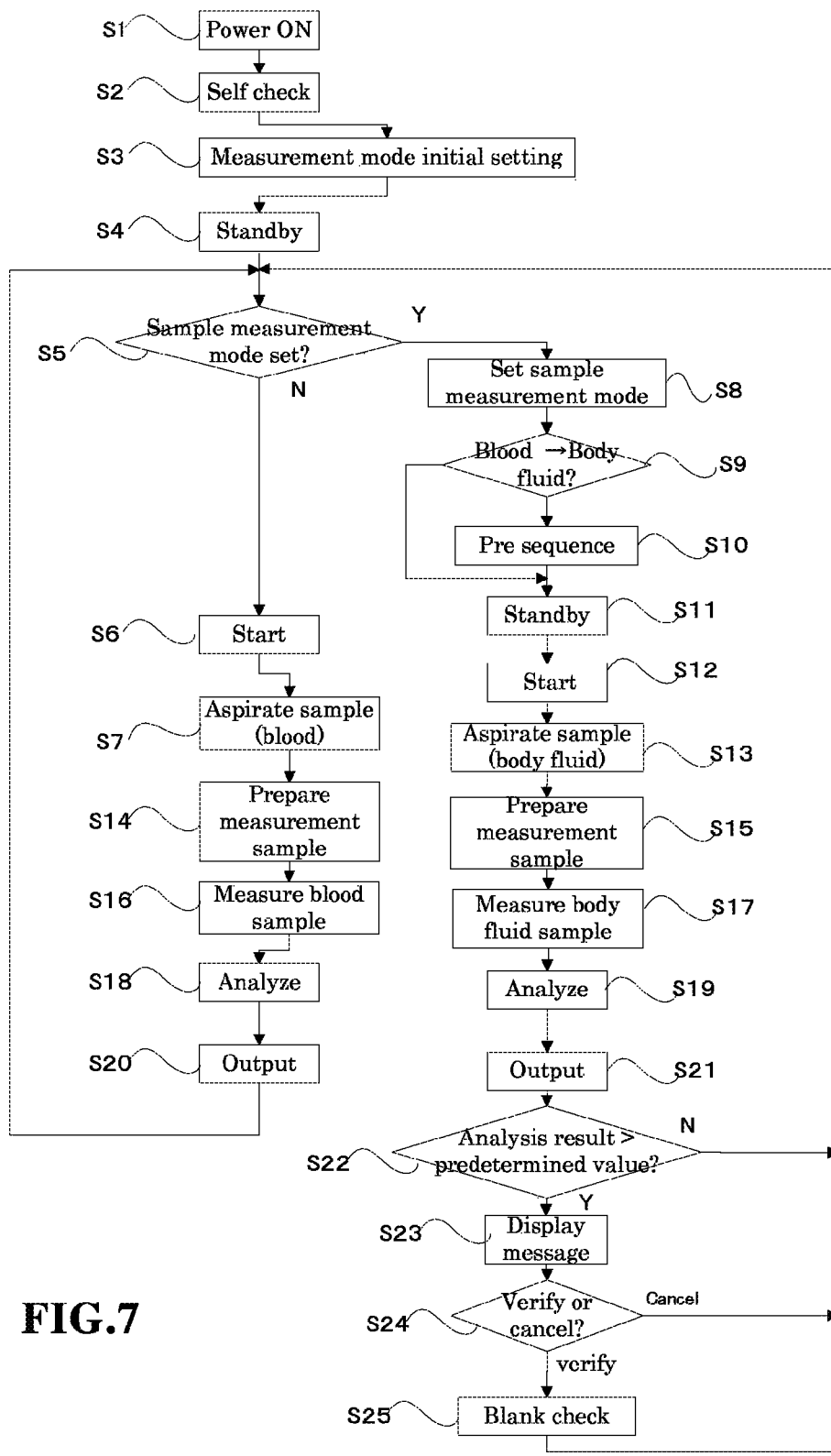
FIG. 7 is a flow chart of the sample measuring process.

The operation of the sample analyzer 1 of the present embodiment is described below. FIG. 7 is a flow chart showing the flow of the operation of the sample analyzer of the present embodiment. The sample analyzer 1 starts when a user turns on the power source of the sample analyzer 1 (step S1). The sample analyzer 1 first executes a self check during startup (step S2). In the self check, the microcomputer 6 tests and checks the operation of all operating device of the sample analyzer 1, and performs a blank check operation which measures a blank sample that does not contain a real sample. Next, the microcomputer 6 sets an initial measurement mode (step S3). The CBC+DIFF mode is the initial setting. Specifically, in the process of step S3, parameters (operating conditions) for performing blood measurements are set, for example, which reaction chamber to use and the set time for the measurement. The blood measurement mode is thus set as the initial operating mode in the sample analyzer 1 of the present embodiment. The sample analyzer 1 therefore remains in a standby state waiting to receive a measurement start instruction. The microcomputer 6 displays a screen on the liquid crystal display which alerts the operator to the standby state (step S4).

In the standby state, the operator can change the measurement mode by operating the display and operation unit 7. FIG. 8 is a schematic view of an input screen for setting the measurement mode. This screen is provided with discrete display regions including the sample number 120, type of sample uptake mode 121, type of discrete test (measurement mode) 122, and type of sample 123. The three sample uptake modes include a manual mode for aspirating a sample after the operator has manually inserted a sample container in the sample aspiration nozzle 18, a capillary mode for aspirating a measurement sample via the sample aspiration nozzle 18 after the operator has previously prepared the measurement sample by mixing a sample and reagent, and a closed mode for supplying a sample by automatically transporting a sample container using a conveyer device. The types of samples include NORMAL, which are normal blood samples; HPC, which are hematopoietic progenitor cell samples; and BODY FLUID, which are other fluids of the body. The operator can specify the sample take-up mode, measurement mode, and type of sample. When the blood measurement mode has been specified, the NORMAL sample type is specified, and an optional sample take-up mode and measurement mode are specified. When specifying the BODY FLUID measurement mode, the operator specifies MANUAL mode as the take-up mode, [CBC+DIFF], [CBC+DIFF+RET], [CBC+DIFF+NRBC], or [CBC+DIFFNRBC+RET] as the DISCRETE test, and [BODY FLUID] as the type of sample. In step S4, the operator specifies the desired mode. The operator presses the start switch to start the measurement when blood measurement is performed without changing the initially set measurement mode (step S5: N). The microcomputer 6 receives the instruction to start the measurement (step S6), and the blood sample is aspirated by the sample aspiration nozzle (step S7).

After the blood sample has been aspirated, the sample is introduced to the previously mentioned sampling valve 18, and the necessary sample preparation is performed for the measurement according to the type discrete test of the measurement mode (step S14). The measurement operation is then executed for this measurement sample (step S16). When [7] is set as the type of discrete test, for example, HGB, WBC/BASO, DIFF, RET, NRBC, and RBC/PLT measurement samples are prepared. Thereafter, the WBC/BASO, DIFF, RET, and NRBC measurement samples are measured by the white blood cell detection unit 41, the RBC/PLT measurement sample is measured by the RBC/PLT detection unit 42, and the HGB measurement sample is measured by the HGB detection unit 43. At this time, the WBC/BASO, DIFF, RET, and NRBC measurement samples are introduced to the white blood cell detection unit 41 in the order NRBC, WBC/BASO, DIFF, RET and sequentially measured since only a single white blood cell detection unit 41 is provided. In this measurement operation, the calculation unit 62 creates particle distribution maps (scattergram, histogram). The scattergram created from the optical information obtained by the DIFF measurement is described below. The calculation unit 62 generates a two-dimensional seattergram (particle distribution map) using, as characteristic parameters, the side scattered light and side fluorescent light among the photoreception signals output from the white blood cell detection unit 41 in the DIFF measurement. This scattergram (referred to as "DIFF scattergram" hereinafter) plots the side scattered light intensity on the X axis and the side fluorescent light on the Y axis; red blood cell ghost clusters, lymphocyte clusters, monocyte clusters, neutrophil+basophil clusters, and eosinophil clusters normally appear. These clusters are recognized by processing performed on the DIFF scattergram by the data analyzing unit 64.

Figure 12:
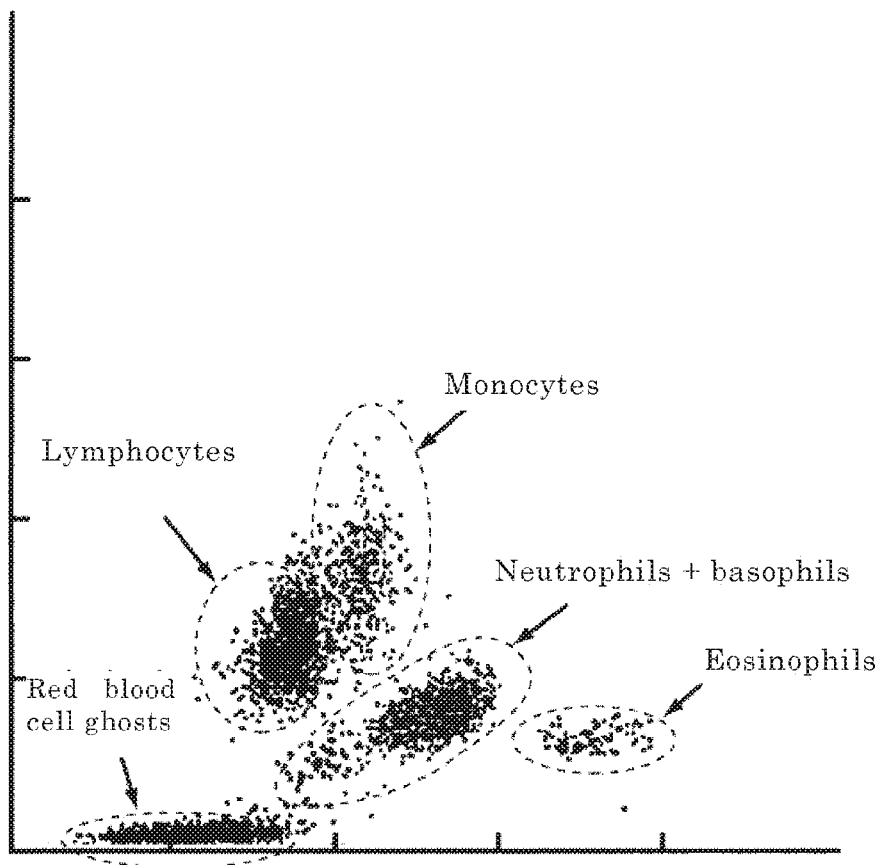
FIG. 12 is a schematic view of a scattergram derived from measurements of a DIFF measurement sample prepared from blood.

Analysis processing is then performed based on the particle distribution maps obtained by the measurement (step S18). In the analysis processing, the data analyzing unit 64 of the microcomputer 6 classifies the four white blood cell clusters (lymphocyte cluster, monocyte cluster, neutrophil+basophil cluster, and eosinophil cluster), and the red blood cell ghost cluster as shown in FIG. 12 from the DIFF scattergram prepared by the calculation unit 62 when the DIFF measurement samples were measured by the white blood cell detection unit 41. In the analysis process of the present embodiment, each particle plotted on the scattergram and the degree of attribution of particles to each cluster at a distance from the center of gravity of each cluster is obtained. Then, each particle is attributed to a cluster according to the degree of attribution. The particle classification method is disclosed in detail in U.S. Pat. No. 5,555,196. The basophil cluster, and white blood cell clusters other than basophils, and the red blood cell ghost cluster are classified on the scattergram obtained by the WBC/BASO measurement. White blood cells are classified in five groups based on the results of the four classifications and numbers of white blood cells (refer to FIG. 12) by the analysis processing of the DIFF scattergram, and the results of the two classification and numbers of white blood cells by the analysis processing of the WBC/BASO scattergram. Specifically, the data analysis unit 64 subtracts the basophil cell count obtained by the analyzing the WBC/BASO scattergram from the neutrophil+basophil cell count obtained by analyzing the DIFF scattergram, to obtain the neutrophil cell count end the basophil cell count. Thus, five classifications of white blood cells are obtained as well as the number of blood cells in each classification. In addition, the trough is detected in the curve in the unidimensional histogram created based on the characteristic information from the detection unit 42, and the particles are classified as red blood cells and platelets in the RBC/PLT measurement. The analysis results thus obtained are output to the display unit 302 of the data processing unit 3 (step S20).

When input specifying the measurement mode is received as described above in step S5, the microcomputer 6 sets the parameters (operating conditions) for the body fluid measurement, for example, the reaction chamber to use and the set time of the measurement and the like (step S8). In the present embodiment, the measurement time is three times the time for blood measurement, as will be described later.

The measuring unit 2 starts the pre sequence (step S10) when the measurement mode has been switched from the previous measurement mode (in this instance, the blood measurement mode) to the body fluid measurement mode (step S9). The pre sequence is a process of preparing for the body fluid measurement. Since samples which have a low concentration of blood cell component are measured in the body fluid measurement, the setting is switched from the blood measurement mode ([1:NORMAL] is displayed in FIG. 8) to the body fluid measurement mode, and the lack of background influence is confirmed in the body fluid measurement results.

The pre sequence includes a blank check operation. The blank check determination standard of the pre sequence is set at a fraction and is more strict than the determination standard of the blank check (for example, the blank check performed after power on and automatic wash) performed in the blood measurement mode. When the setting is changed from the body fluid measurement mode to the blood measurement mode, this pre sequence is not performed since there is no background influence (carry over effect) on the normal blood measurement results. Furthermore, when body fluid samples are measured in a repeated body fluid measurement mode, this pre sequence is not performed since there is normally no background influence. There is concern, however, that the next sample measurement may be affected when the body fluid sample analysis results exceed a predetermined value due to an extremely high number of particles in the body fluid since the measurement results are high, and therefore the operator is alerted of this concern that the analysis results of the next sample may be affected. Then, the blank check measurement is performed. A configuration is desirable in which a message "please press VERIFY" is output to the screen, and the blank check is performed when the operator presses the VERIFY button. In this case, a configuration is possible in which a CANCEL button may be provided on the screen to transition to the standby screen without performing a blank check when the operator presses the CANCEL button. It is also desirable that a flag indicate the low reliability of the measurement results when a blank check is not performed. Wasted reagent and time can thus be avoided by performing an additional blank check only when needed.

Figure 9:
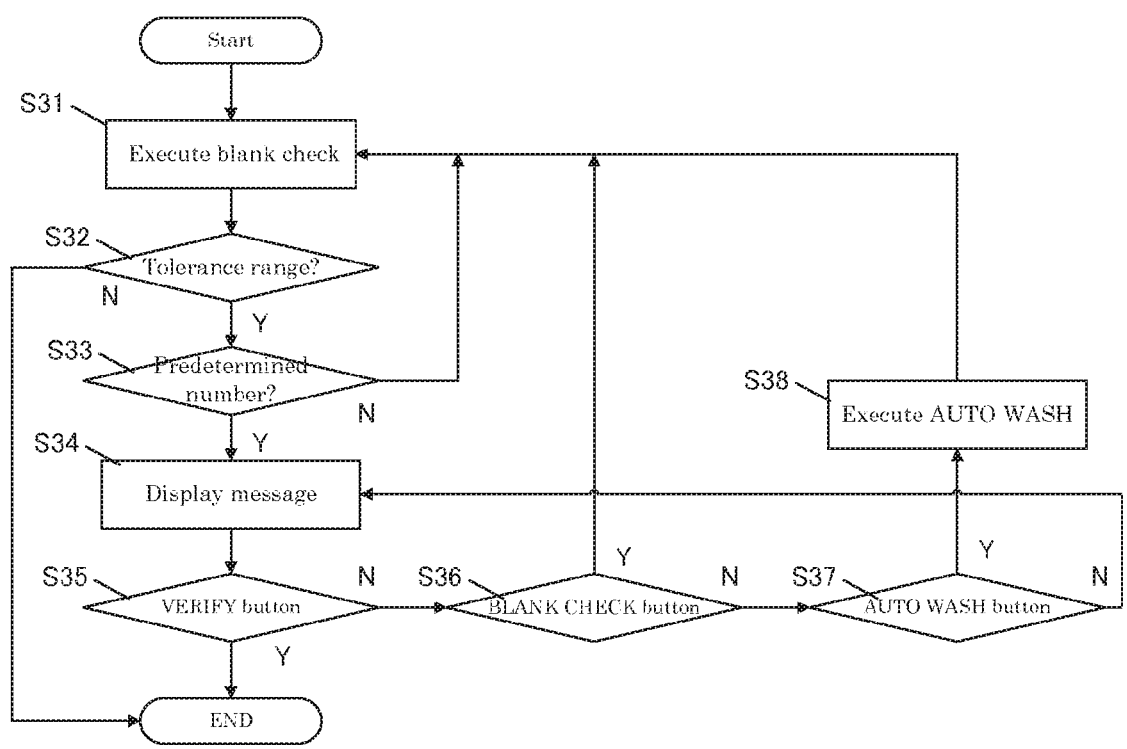
FIG. 9 is a flow chart showing the pre sequence process.

FIG. 9 is a flow chart showing the sequence of the pre sequence process performed when the measurement mode is changed from the blood measurement mode to the body fluid measurement mode. The sample analyzer 1 performs the pre sequence by measuring a blank sample using the measuring unit 2 (step S31), comparing the measurement result with predetermined tolerance values and determining whether or not the measurement results are less than the tolerance values using the microcomputer 6 (step S32). When the measurement results are less than the tolerance values, the microcomputer 6 ends the pre sequence and the process returns. When the measurement results are not less than the tolerance value, the microcomputer 6 determines whether or not the blank check was executed the set number of times (for example, three times) (step S33), and when the number of executions of the blank check is less than a predetermined number, the process returns to step S31 and the blank check is performed again for the predetermined number of times. When the measurement results of the blank check performed a predetermined number of times are not less than the tolerance values, a screen is displayed with includes a VERIFY button, BLANK CHECK button, and AUTOMATIC WASH button and the blank check measurement results are displayed on the display and operation unit 7 (step S34). When the operator has pressed the VERIFY button (step S35), the microcomputer 6 ends the pre sequence and the process returns. When the BLANK CHECK button has been pressed (step S36), the process returns to step S31 and the blank check is performed again; when the AUTOMATIC WASH button has been pressed (step S37), automatic washing is performed using a special washing solution (step S38), and thereafter the process returns to step S31 and the blank check is performed again.

When the pre sequence ends as described above, the sample analyzer 1 enters the standby state (step S11). When the operator presses the start switch and starts the body fluid measurement, the sample aspiration nozzle 18 of the measuring unit 2 is immersed in the sample container in the same manner as for the manual measurement of the blood sample. When the instruction to start measurement is received by the microcomputer 6 (step S12), the body fluid aspiration begins (step S13).

After the body fluid sample has been aspirated, the body fluid sample is introduced to the sampling valve 91 in the same manner as the blood sample. Then, the RBC/PLT measurement sample is prepared by the reaction chamber 13 (step S15). Subsequently, the DIFF measurement sample is measured by the white blood cell detection unit 41, and the RBC/PLT measurement sample is measured by the RBC/PLT detection unit 42 (step S17). Since only the DTFF measurement sample is measured by the white blood cell detection unit 41 in the body fluid measurement mode, the measurement is completed in a shorter time than the blood measurement even though the measurement time is longer than the measurement time in the blood measurement mode, the analysis accuracy of the low particle concentration body fluid sample can therefore be improved by increasing the measurement time of the body fluid measurement to be longer than the measurement time of the blood measurement. Although the measurement accuracy can be improved due to the increased number of particles counted by lengthening the measurement time, a two to six fold increase in the measurement time is suitable because the sample processing ability is reduced when the measurement time is excessively long, and there is a limit to the performance of the syringe pump which delivers the measurement sample to the white blood cell detection unit 41. In the present embodiment, the measurement time in the body fluid measurement mode is set at three times the measurement time of the blood measurement mode.

The RBC/PLT measurement sample is introduced to the electrical resistance detection unit 41 in the same manner for all measurement modes, and measurement is performed under a fixed flow speed condition. The analysis processing is performed thereafter based on the characteristic information obtained by the measurements (step S19), and the analysis results are output to the display unit 302 of the data processing unit 3 (step S21). In the analysis processing of the blood measurement mode, the DIFF scattergram and the like are analyzed, and information is calculated for five types of white blood cell subclasses (NEUT: neutrophil, LYMPH; lymphocyte, MONO: monocyte, EO: eosinophil, and BASO: basophil), whereas in the analysis processing of the body fluid measurement mode, two subclasses (MN: mononuclear cell, PMN: polymorphonuclear cell) are classified in a partially integrated form because there are a lesser number of blood cells and these cells are sometimes damaged. The lymphocytes and monocytes belong to mononuclear cells, and neutrophils, eosinophils, and basophils belong to polymorphonuclear cells. Since the classification algorithm is the same as the algorithm described for the analysis processing in the blood measurement mode, further description is omitted.

Figure 17:
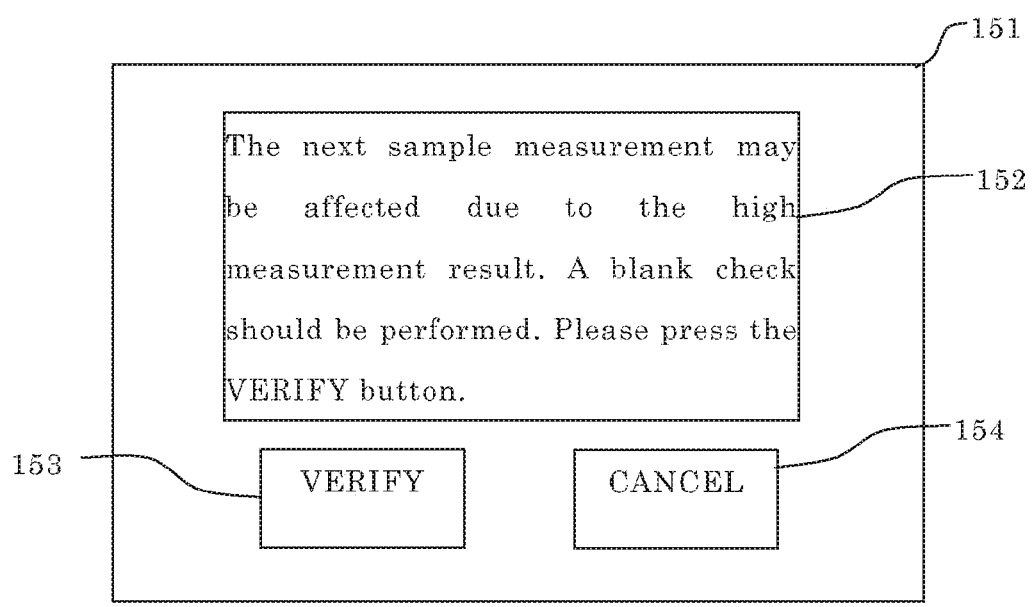
FIG. 17 is a confirmation screen at the start of the blank check which is displayed in the body fluid measurement mode.

Next, the analysis results obtained in step S19 are compared to the tolerance value (predetermined threshold value) (step S22). The tolerance value is the same value as the tolerance value used in the blank check of the pre sequence performed in step S10. When the analysis result is greater than the tolerance value (step S22: Y), the verification screen 151 at the start of the blank check is displayed, as shown in FIG. 17. A message is displayed on the verification screen 151 indicating there is concern that the measurement of the next sample may be influenced due to the high measurement result. Then, the blank check measurement is performed. A message display area 152 for displaying the message "please press the VERIFY button", a VERIFY button 153, and a CANCEL button 154 are displayed. Next, determinations are made as to whether or not the user has pressed the VERIFY button 153 or the CANCEL button 154 (step S24), and the blank check is executed when the VERIFY button has been pressed (VERIFY in step S24) (step: S25). The process returns to step S5 without performing the blank check when the analysis result obtained in step S19 is less than the tolerance value (step S22: N), and the when the CANCEL button has been pressed (CANCEL in step S24).

Anomalous particles (macrophages, mesothelial cells, tumor cells and the like) other than blood cells may be present in the body fluid sample. Although it is rare for such anomalous cells to be present in cerebrospinal fluid, such cells appear comparatively frequently in abdominal and thoracic fluids. The influence of these anomalous particles must be eliminated in order to obtain a high precision classification of blood cells within the body fluid regardless of the type of body fluid. White blood cells in body fluid can be measured with greater precision based on the new knowledge than anomalous particles appear in the top part of the DIFF scattergram produced by this blood cell analyzer of the present invention. This aspect was not considered in the previously mentioned conventional art.

Figure 10:
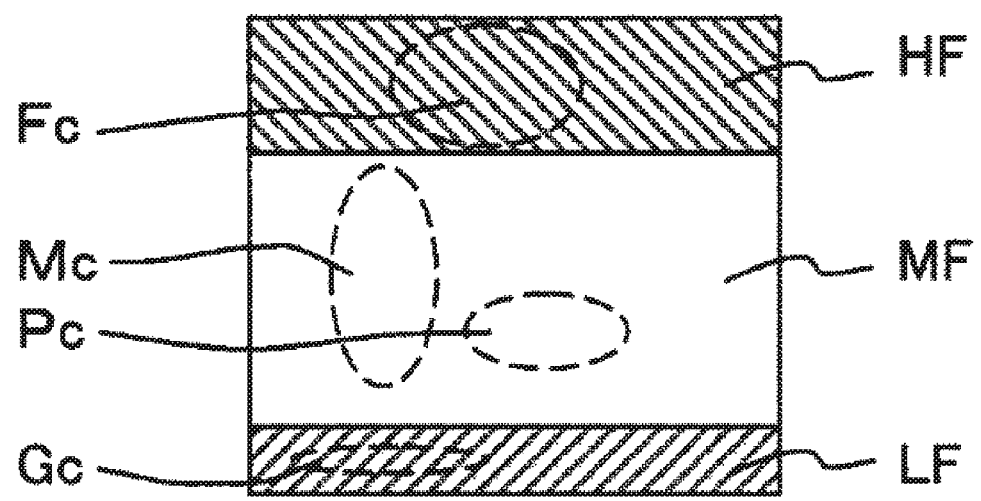
FIG. 10 is a schematic view of a scattergram derived from measurements of a DIFF measurement sample prepared from body fluid.

FIG. 10 is a schematic view of a scattergram obtained by measuring and analyzing a DIFF measurement sample prepared from body fluid and white blood cell measurement reagent in the body fluid measurement mode of the blood cell analyzer 1 of the present embodiment. The vertical axis of the scattergram represents the side fluorescent light intensity (the fluorescent light intensity at the top is greatest), and the horizontal axis represents the side scattered light intensity (the scattered light intensity at the right side is greatest). A red blood cell ghost Gc caused by hemolysis is distributed in the region LF in which the fluorescent light intensity is weakest in the scattergram, anomalous particles such as mesothelial cells and the like is distributed in the region HF in which the fluorescent light intensity is greatest, and mononuclear white blood cells Mc and polynuclear white blood cells Pc are distributed in the intermediate region MF. In the analysis of the scattergram, the particle component distributed in the region MF is analyzed as white blood cells after excluding region LF and region HF, and the particles are classified and counted in two groups. Lymphocytes and monocytes are included in the mononuclear white blood cells Mc, and neutrophils, basophils, and eosinophils are included in the polynuclear white blood cells PC.

Since fewer and damaged blood cells are contained in body fluid, white blood cells are classified and counted as mononuclear white blood cells and polynuclear white blood cells when analyzing white blood cells in body fluid.

Anomalous particles (nucleated cells such as tumor cells, macrophages, mesothelial cells) other than blood cells may also be present in body fluid. Although it is rare for such anomalous cells to be present in cerebrospinal fluid, such cells appear comparatively frequently in abdominal and thoracic fluids. In the scattergram of FIG. 10, such nucleated cells other than white blood cells are distributed in region HF. In the present embodiment, it is possible to determine accurate white blood cells counts even in body fluid which contains such nucleated cells other than white blood cells since nucleated cells other than white blood cells can be identified. The degree of occurrence of anomalous cells can be determined by counting the cells which appear in region HF. In the present embodiment, cells are demarcated in the regions LF, MF, and HF by threshold values for demarcating each region; these threshold values may also be changed manually.

FIG. 11 compares the analysis results of the blood cell analyzer 1 of the present embodiment and the count results of a reference method to show the validity of the scattergram analysis method described above. The sample material is thoracic fluid; in the drawing, "this method" refers to the white blood cell count (WBC) and anomalous particle count (Others) calculated by the blood cell analyzer 1 of the present embodiment, and "Ref" refers to the calculation result by the reference methods (Fuchs Rosenthal calculation method and site-spin method). Examples 1, 2, and 3 are the results of analysis of thoracic fluid in which anomalous particles were plentiful, and the correlation between the reference methods and the analysis results of the blood cell analyzer 1 of the present invention can be readily understood.

Figure 13:
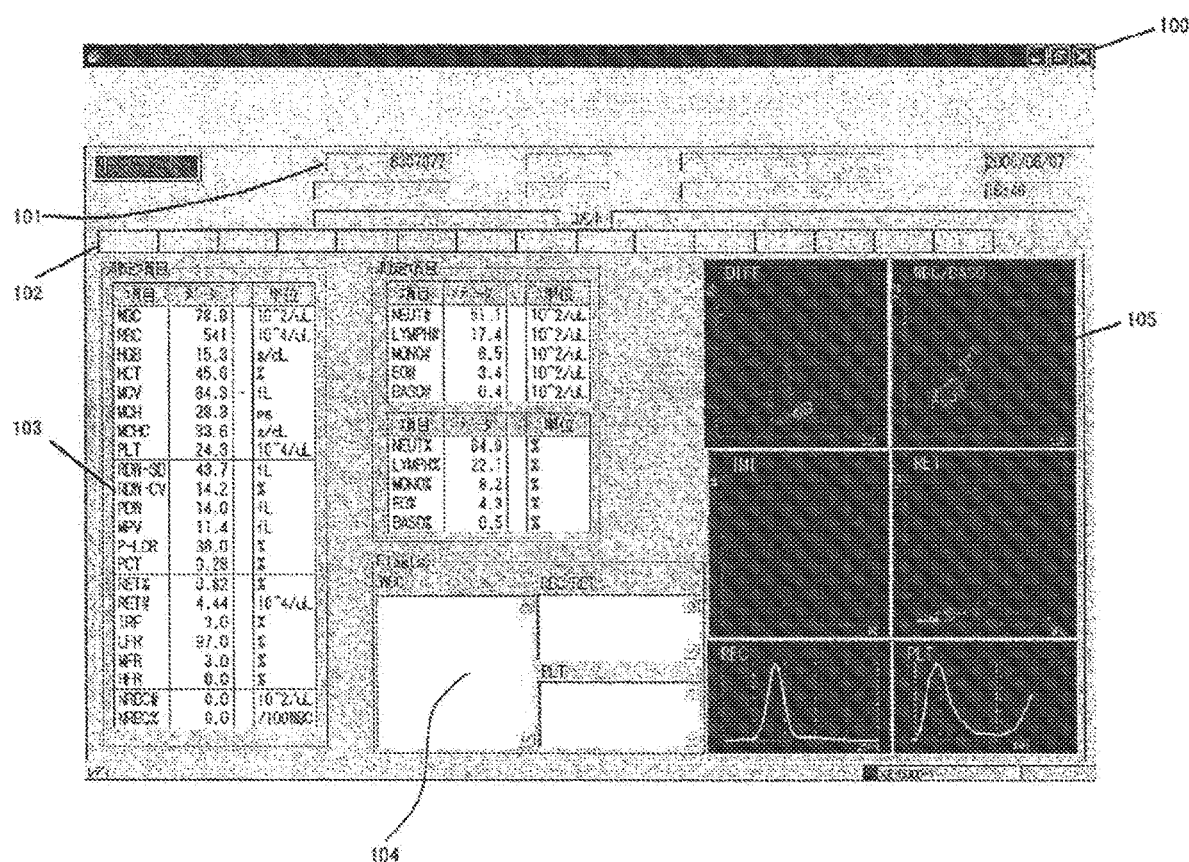
FIG. 13 is a display screen showing the measurement results in the blood measurement mode.

FIG. 13 shows a screen 200 which is displayed on the display unit 302 of the data processing unit 3, showing the analysis results of the DIFF measurement sample prepared from blood. A sample number display region which displays a sample number 101 is provided at the top of the screen 200, and an attribute display region which displays patient attributes is provided adjacently. The attribute display region specifically includes a patient ID, patient name, date of birth, sex, hospital department/ward, attending physician, date of measurement, time of measurement, comments and the like. A measurement result display region which displays the measurement results is provided at the bottom of the attribute display region. The measurement result display region includes several pages, and these pages can be displayed by selecting a plurality of tabs 102. Tabs have a plurality of arrangements matching the main screen, graph screen, and measurement items. FIG. 12 is a screen which is displayed when the graph screen tab has been selected. A graph display region 104 for displaying graphs and a measurement value display region 103 for displaying the measurement result values are provided in the left half of the measurement value display region, and a distribution map display region for displaying the measurement result distribution map 105 is provided in the right half. WBC, RBC, . . . , NEUT #, . . . , BASO #, . . . , NEUT #, . . . , BASO % and the like, data, and units are displayed in the measurement value display region, and flagging results representing sample anomalies and disease suspicions which are clinically useful information relating to WBC, PLT, RBC or RET are displayed in the flag display region 104.

Six distribution maps are displayed in the distribution map display region 105. The scattergram on the upper left side is a DIFF scattergram. The WBC/BASO scattergram is shown at the top right, the immature cell (IMI) scattergram is shown at mid left, and the RET scattergram is shown at mid right. The RBC scattergram is shown at the bottom left, and the PLT scattergram is shown at the bottom right.

Figure 14:
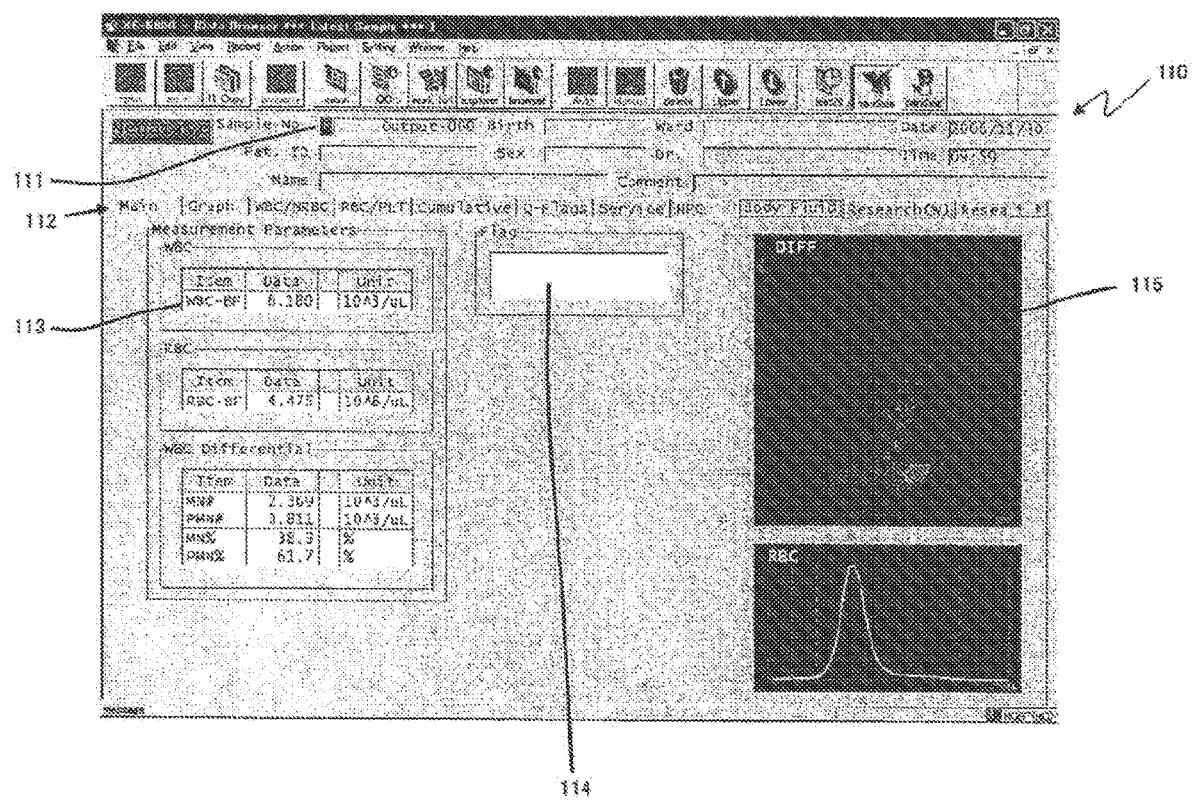
FIG. 14 is a display screen showing the measurement results in the body fluid measurement mode.

FIG. 14 shows a screen 110 displayed in the display area 302 of the data processing unit 3 as the measurement results of the DIFF measurement sample prepared from body fluid. A sample number display region 111 for displaying a sample number is provided at the top of the screen 110, and a patient attribute display region is provided adjacently. An [F], which indicates measurement has been conducted in the body fluid measurement mode, is displayed at the left end of the sample number display region 111. Thus, it can be clearly recognized that the analysis results are for body fluid measurement results. The measurement result display region includes a plurality of pages which are selectable by tab 112. In this example, the tab for body fluid measurement is selected.

The measurement value display region 113 includes the name of the measurement items for body fluid measurement rather than the measurement results of the blood measurement mode; WBC-BF (WBC count), RBC-BF (RBC count), MN # (mononuclear cell count (lymphocytes+monocytes)), PMN # (polymorphonuclear cell count (neutrophils+basophils+eosinophils)), MN % (ratio of mononuclear cells among white blood cells), PMN % (ratio of polymorphonuclear cells among white blood cells), measurement values, and units are associated and displayed. A flag display region 114 is provided in the body fluid measurement similar to the blood measurement. Two distribution maps 115 are displayed in the distribution map display region, and the top scattergram is a DIFF scattergram. The bottom scatter gram is an RBC scattergram.

Figure 15:
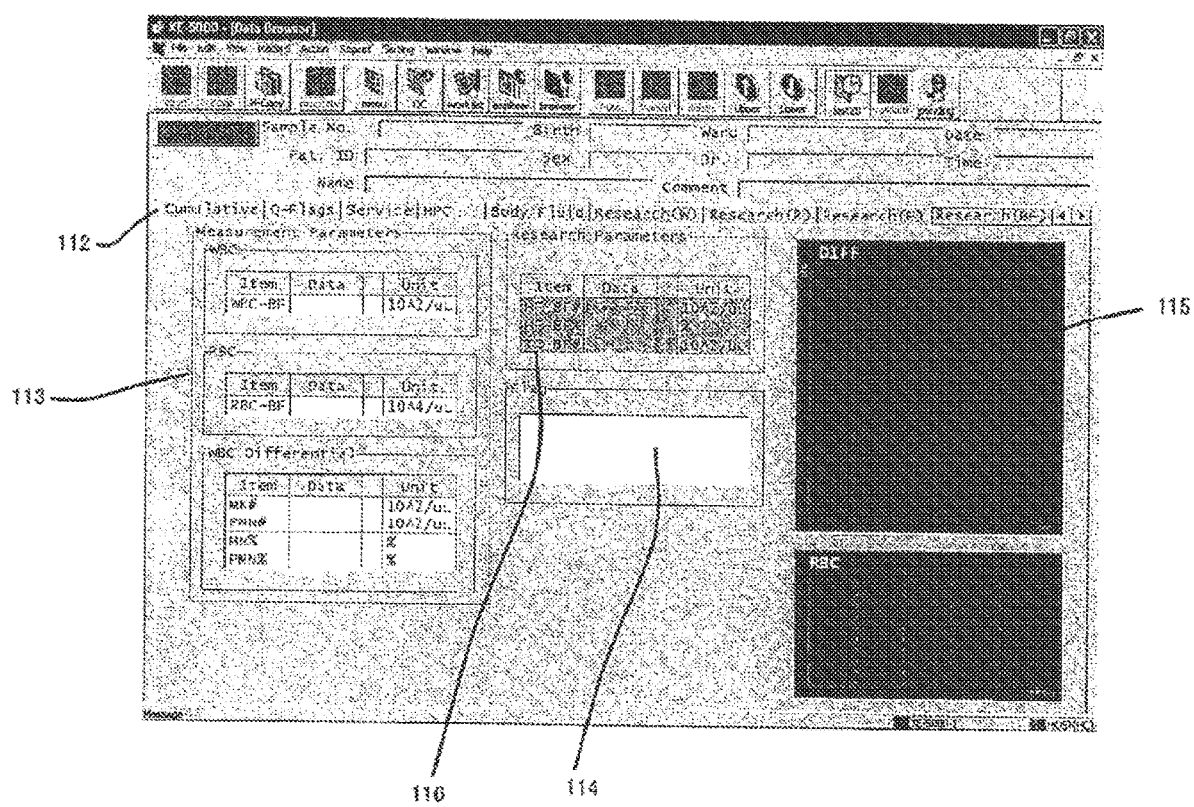
FIG. 15 is a display screen showing the measurement results in the body fluid measurement mode.

FIG. 15 shows an example In which the Research BF tab 112 is selected in the screen 110 of FIG. 14. This screen displays the same items as screen 110 with the exception that a research parameter display region 116 is also displayed. The research parameter display region 116 displays number of particles in region HF [HF-BF #], the ratio of the number of particles in the region HF relative to the number of particles in the region including both region HF and region MF [HF-BF %], and the number of particles in the region including both region HF and region MF [TC-BF #] in FIG. 10. [HF-BF %] is the percentage of HF-BF relative to TC-BF.

Figure 16:
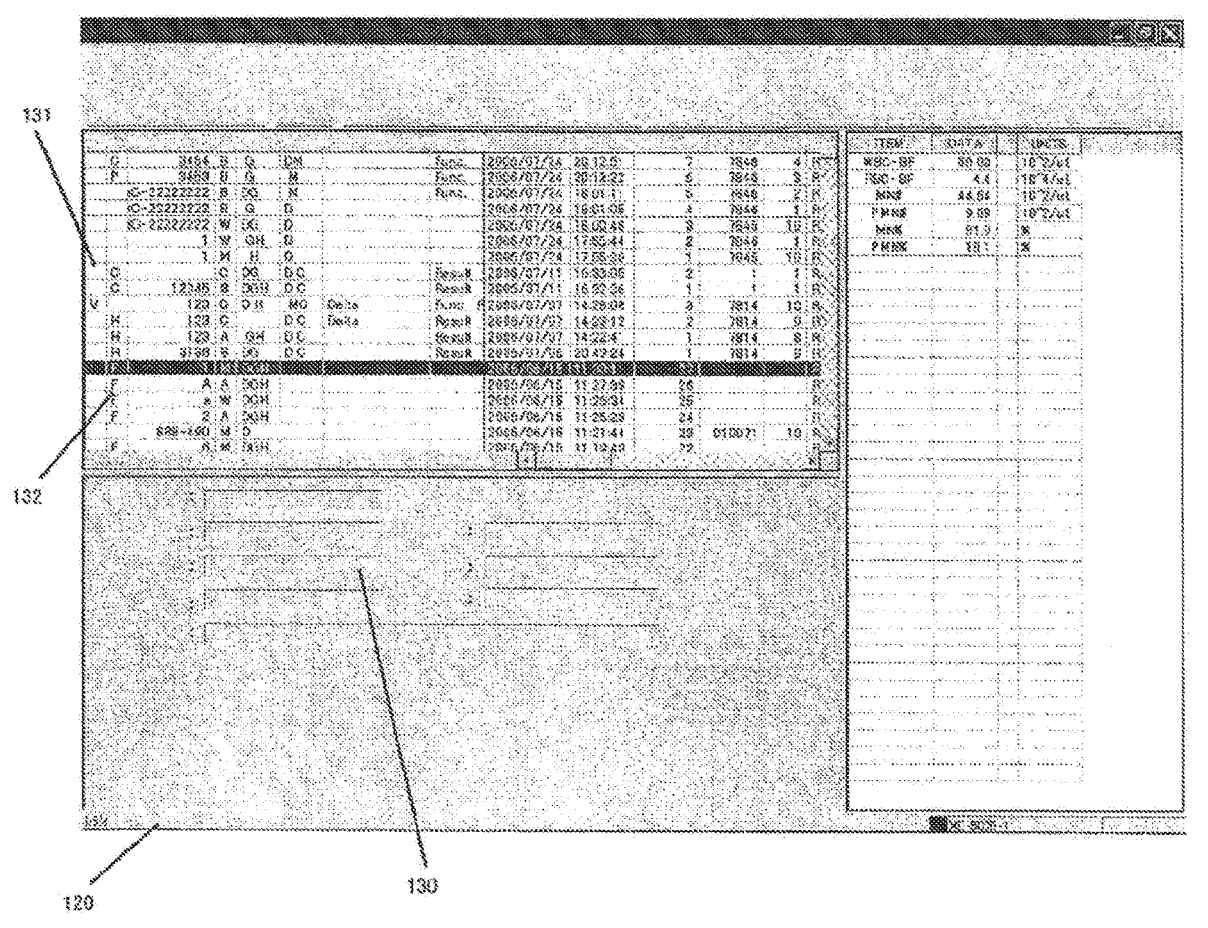

FIG. 16 shows a screen 120 showing a list of stored samples which is displayed on the display unit 302 of the data processing unit 3. Reference number 130 refers to a patient attribute display region. Provided above this region is a measurement result display region which displays the measurement result selected by a tab. A row 131 on the left end of the measurement result display region is used to indicate whether the validation operation has been performed or not for the measurement result. A "V" symbol indicates validation has been performed. A row 132 on the right indicates the measurement mode. An "F" symbol indicates the measurement results are for the body fluid mode. Although there are high value samples that require blank checking in the body fluid mode, and inverted "F" symbol can be displayed to indicate the blank check has not been performed (that is, CANCEL was selected in step S24).

Although the structure and functions of the blood cell analyzer of the present invention have been described as being pre-established in the blood cell analyzer, the same functions may be realized by a computer program so that the functions of the present invention can be realized in a conventional blood cell analyzer by installing the computer program in a conventional blood cell analyzer.

Although the amount of sample, type of reagent, and amount of reagent are the same when preparing measurement samples for the white blood cell classification measurement in the blood measurement mode and the white blood cell classification measurement in the body fluid measurement mode in the present embodiment, the present invention is not limited to this configuration inasmuch as the amount of sample and the amount of reagent used to prepare a measurement sample for white blood cell classification in the body fluid measurement mode may be greater than the amount of sample and the amount of reagent used to prepare a measurement sample for white blood cell classification in the blood measurement mode. Since the measurement time is greater and the amount of measurement sample needed for measurement is greater for white blood cell classification in the body fluid measurement mode than in the blood measurement mode, it is thereby possible to prepare suitable amounts of measurement sample for white blood cell classification in the blood measurement mode and for white blood cell classification in the body fluid measurement mode. Moreover, the type of reagent used for white blood cell classification in the blood measurement mode may differ from the type of reagent used for white blood cell classification in the body fluid measurement mode.

Although white blood cell classification is performed in the body fluid measurement mode using scattered light and fluorescent light in the present embodiment, the present invention is not limited to this configuration inasmuch as white blood cell classification may also be performed in the body fluid measurement mode using, for example, scattered light and absorbed light. The measurement of absorbed light may be accomplished by preparing a measurement sample by mixing a staining reagent to stain the white blood cells, and other reagent together with the sample, supplying this measurement sample to a flow cell to form a sample flow within the flow cell, irradiating this sample flow with light, and receiving the light emitted from the sample flow via a photoreceptor element such as a photodiode or the like. The light is absorbed by the white blood cells when the white blood cells pass through the flow cell, and the degree of that absorption can be grasped as the amount of light received by the photoreceptor element. Such measurement of absorbed light is disclosed in U.S. Pat. Nos. 5,122,453, and 5,138,181, furthermore, electrical resistance may be measured rather than scattered light, in which case white blood cells can be classified by the electrical resistance and absorbed light.

What is claimed is:

1. A method for analyzing a sample by a sample analyzer that comprises a plurality of chambers each configured to receive a sample selectively comprising (i) a blood sample or (ii) a body fluid sample, and a plurality of detectors each configured to interrogate cells in the sample and output measurements of the cells in the sample, the method comprising;

displaying a selection screen arranged to allow a user to select either the blood sample or the body fluid sample for measurement, wherein the body fluid sample contains body fluid other than blood, which comprises one of cerebrospinal fluid, thoracic fluid, abdominal fluid, fluid collecting in the cardiac sac, synovial fluid, dialysate from peritoneal dialysis, or intraperitoneal rinse;

in response to selection of the blood sample for measurement, executing a blood measuring algorithm defining a sequence of operations for sensing cells in the blood sample, wherein executing the blood measuring algorithm comprising reconfiguring the sample analyzer into a blood sample analyzer operable to: introduce the blood sample into one of the plurality of chambers; operate one of the plurality of detectors to sense cells in the introduced blood sample; and derive, from measurements from said one of the plurality detectors, a digitally analyzable form of measurements on the cells in the introduced blood sample; and in response to selection of the body fluid sample for measurement, executing a body fluid measuring algorithm, different from the blood measuring algorithm, which defines a sequence of operations for sensing cells in the body fluid sample, wherein executing the body fluid measuring algorithm comprises reconfiguring the sample analyzer into a body fluid sample analyzer operable to: introduce the body fluid sample into said one or another of the plurality of chambers; operate said one or another of the plurality of detectors to sense cells in the introduced body fluid sample; and derive, from measurements from said one or another of the plurality of detectors, a digitally analyzable form of measurements on the cells in the introduced body fluid sample.

2. The method according to claim 1, wherein
executing the blood measuring algorithm comprises operating the blood sample analyzer to sense the cells in the introduced blood, sample for a first measurement time,
executing the body fluid measuring algorithm comprises operating the body fluid sample analyzer to sense the cells in the introduced body fluid sample for a second measurement time, wherein the second measurement time is longer than the first measurement time.

3. The method according to claim 1, further comprising: washing said one of the plurality of chambers; and introducing the body fluid sample into said one of the plurality of chambers after washing to reduce a carryover effect on the measurement of the cells in the body fluid sample.

4. The method according to claim 1, wherein executing the body fluid measuring algorithm comprises analyzing the digitally analyzable form of measurements of the cells in the introduced body fluid sample and counting a type of cells of interest among the cells in the introduced body fluid sample.

5. The method according to claim 4, wherein counting a type of cells of interest comprises counting at least one of mono-nucleated cells or poly-nucleated cells among the cells in the introduced body fluid sample.

6. The method according to claim 5, wherein executing the body fluid measuring algorithm further comprising calculating a relative amount of the at least one of mono-nucleated cells or poly-nucleated cells.

7. The method according to claim 4, wherein counting a type of cells of interest comprises counting at least one of neutrophil, lymphocyte, monocyte, eosinophil or basophil.

8. The sample analyzer according to claim 1, further comprising:
introducing a cell-free sample into said one of the plurality of chambers for measurement by said one of the plurality of detectors, wherein the cell-free sample having no cells contained in the cell-free sample;
running the cell-free sample through said one of the plurality of chambers and said one of the plurality of detectors; and
analyzing the digitally analyzable form of measurements of the cell-free sample and counting cells carried over into the cell-free sample from a test sample previously measured.

* * * * *

UNITED STATES PATENT AND TRADEMARK OFFICE
CERTIFICATE OF CORRECTION

| | | |
|---|---|---|
| PATENT NO. | : 11,415,575 B2 | Page 1 of 1 |
| APPLICATION NO. | : 16/180590 | |
| DATED | : August 16, 2022 | |
| INVENTOR(S) | : Takaaki Nagai et al. | |

It is certified that error appears in the above-identified patent and that said Letters Patent is hereby corrected as shown below:

In the Claims

In Column 17, Line 17, delete "," between blood and sample.

Signed and Sealed this
Eleventh Day of October, 2022

Katherine Kelly Vidal
*Director of the United States Patent and Trademark Office*